United States Patent
Puthigae et al.

(10) Patent No.: US 8,901,376 B2
(45) Date of Patent: Dec. 2, 2014

(54) METHODS AND COMPOSITIONS FOR THE IMPROVEMENT OF PLANT TOLERANCE TO ENVIRONMENTAL STRESSES

(75) Inventors: Sathish Puthigae, Auckland (NZ); Jonathan Robert Phillips, Chesterfield, MO (US); Claudia Jeannette Smith-Espinoza, Chesterfield, MO (US); Catherine Jane Bryant, Auckland (NZ); Kieran Michael Elborough, Pukekohe (NZ)

(73) Assignee: Vialactia Biosciences (NZ) Limited, Auckland (NZ)

( * ) Notice: Subject to any disclaimer, the term of this patent is extended or adjusted under 35 U.S.C. 154(b) by 205 days.

(21) Appl. No.: 13/132,042

(22) PCT Filed: Dec. 1, 2009

(86) PCT No.: PCT/NZ2009/000269
§ 371 (c)(1),
(2), (4) Date: Aug. 19, 2011

(87) PCT Pub. No.: WO2010/064934
PCT Pub. Date: Jun. 10, 2010

(65) Prior Publication Data
US 2011/0302674 A1 Dec. 8, 2011

Related U.S. Application Data

(60) Provisional application No. 61/118,982, filed on Dec. 1, 2008.

(51) Int. Cl.
C12N 15/82 (2006.01)
C12N 15/63 (2006.01)
C07K 14/415 (2006.01)

(52) U.S. Cl.
CPC .......... *C12N 15/8271* (2013.01); *C07K 14/415* (2013.01)
USPC .......... 800/289; 800/278; 800/283; 800/298; 536/23.6; 435/468; 435/410; 435/320.1; 530/370

(58) Field of Classification Search
None
See application file for complete search history.

(56) References Cited

U.S. PATENT DOCUMENTS

| | | | |
|---|---|---|---|
| 4,795,855 A | 1/1989 | Fillatti et al. |
| 5,004,863 A | 4/1991 | Umbeck |
| 5,159,135 A | 10/1992 | Umbeck |
| 5,177,010 A | 1/1993 | Goldman et al. |
| 5,187,073 A | 2/1993 | Goldman et al. |
| 5,188,958 A | 2/1993 | Moloney et al. |
| 5,352,605 A | 10/1994 | Fraley et al. |
| 5,364,780 A | 11/1994 | Hershey et al. |
| 5,416,011 A | 5/1995 | Hinchee et al. |
| 5,463,174 A | 10/1995 | Moloney et al. |
| 5,510,474 A | 4/1996 | Quail et al. |
| 5,563,055 A | 10/1996 | Townsend et al. |
| 5,569,834 A | 10/1996 | Hinchee et al. |
| 5,591,616 A | 1/1997 | Hiei et al. |
| 5,750,871 A | 5/1998 | Moloney et al. |
| 5,792,935 A | 8/1998 | Arntzen et al. |
| 5,824,877 A | 10/1998 | Hinchee et al. |
| 5,846,797 A | 12/1998 | Strickland |
| 5,952,543 A | 9/1999 | Firoozabady et al. |
| 5,968,830 A | 10/1999 | Dan et al. |
| 5,981,840 A | 11/1999 | Zhao et al. |
| 6,020,539 A | 2/2000 | Goldman et al. |
| 6,037,522 A | 3/2000 | Dong et al. |
| 6,074,877 A | 6/2000 | D'Halluin et al. |
| 7,365,185 B2 | 4/2008 | Boukharov et al. |
| 7,408,052 B2 | 8/2008 | Cheikh et al. |
| 7,491,806 B2 | 2/2009 | Conner et al. |
| 2003/0046732 A1 | 3/2003 | Kinnersley et al. |
| 2004/0031072 A1 | 2/2004 | La Rosa et al. |
| 2004/0034888 A1 | 2/2004 | Liu et al. |
| 2004/0123343 A1 | 6/2004 | La Rosa et al. |
| 2004/0172684 A1 | 9/2004 | Kovalic et al. |
| 2004/0214272 A1 | 10/2004 | La Rosa et al. |
| 2004/0216190 A1 | 10/2004 | Kovalic |
| 2005/0108791 A1 | 5/2005 | Edgerton |
| 2006/0041961 A1 | 2/2006 | Abad |
| 2006/0123505 A1 | 6/2006 | Kikuchi et al. |
| 2006/0179511 A1 | 8/2006 | Chomet et al. |
| 2006/0236419 A1 | 10/2006 | La Rosa et al. |
| 2007/0020621 A1 | 1/2007 | Boukharov et al. |

(Continued)

FOREIGN PATENT DOCUMENTS

WO 01/04285 1/2001
WO 02/00894 3/2002

(Continued)

OTHER PUBLICATIONS

Hohe et al. A tool for understanding homologous recombinations in plants. Plant Cell Rep. 2003. 21: 1135-1142.*
Vaucheret et al. Transgene-induced gene silencing in plants. Plant Journal. 1998. 16(6): 651-659.*
Xu et al. GenBank Accession No. DQ334411. NCBI Direct Submission. Published Sep. 12, 2007. pp. 1-2.*
Xu et al. GenBank Accession No. ABC65857. NCBI Direct Submission. Published Sep. 12, 2007. p. 1.*
Xu et al. Isolation and molecular characterization of the *Triticum aestivum* L. ethylene-responsive factor 1 (TaERF1) that increases multiple stress tolerance. Plant Molecular Biology. 2007. 65: 719-732.*
GenBank Accession No. AB016265.1. *Nicotiana syvlestris* nserf3 gene for ethylene-respsonsive element binding factor. Published Jun. 20, 2000. pp. 1-2.*

(Continued)

*Primary Examiner* — Brent T Page
*Assistant Examiner* — Ashley K Buran
(74) *Attorney, Agent, or Firm* — Lathrop & Gage LLP

(57) ABSTRACT

The invention provides methods, polynucleotides and polypeptides useful for producing or selecting plants with increased tolerance to at least one environmental stress selected from drought, cold, freezing, heat and salinity. The invention also provides constructs, cells, plant cells and plants comprising the polynucleotides of the invention. The invention also provides plants produced by the methods of the invention. The invention also provides groups of plants selected by the methods of the invention.

14 Claims, 6 Drawing Sheets

(56) References Cited

U.S. PATENT DOCUMENTS

| | | | |
|---|---|---|---|
| 2007/0044171 | A1 | 2/2007 | Kovalic et al. |
| 2007/0067865 | A1 | 3/2007 | Kovalic et al. |
| 2007/0294782 | A1 | 12/2007 | Abad et al. |
| 2008/0301839 | A1 | 12/2008 | Ravanello |
| 2010/0242134 | A1 | 9/2010 | Puthigae et al. |
| 2010/0293664 | A1 | 11/2010 | Puthigae et al. |
| 2011/0179517 | A1 | 7/2011 | Puthigae et al. |
| 2011/0185452 | A1 | 7/2011 | Puthigae et al. |
| 2011/0209250 | A1 | 8/2011 | Puthigae et al. |
| 2011/0302670 | A1 | 12/2011 | Puthigae et al. |
| 2012/0005773 | A1* | 1/2012 | Aasen et al. .................. 800/275 |
| 2012/0084880 | A1 | 4/2012 | Puthigae et al. |

FOREIGN PATENT DOCUMENTS

| | | |
|---|---|---|
| WO | 02/50294 | 6/2002 |
| WO | 2004/058963 | 7/2004 |
| WO | 2004/113536 | 12/2004 |
| WO | 2005/123919 | 12/2005 |
| WO | 2007/027866 | 3/2007 |
| WO | 2007/044043 | 4/2007 |
| WO | 2007/049275 | 5/2007 |
| WO | 2007/078286 | 7/2007 |
| WO | 2008/121008 | 10/2008 |

OTHER PUBLICATIONS

GenBank Accession No. BAA33434.1. DREB1A. published Feb. 14, 2004. pp. 1.*

Seki et al. Molecular repsonses to drought, salinty, and frost: common and different paths for plant protection. Current Opinion in Biotechnology. 2002. 14: 194-199.*

Search Report and Written Opinion, dated Mar. 8, 2010, corresponding to International Application No. PCT/NZ2009/000269 (filed Dec. 1, 2009), parent of the present application, 18 pp.

GenBank Accession No. DT709751, Sep. 12, 2005,1 pg.

Abbott et al. (2002) "Simultaneous Suppression of Multiple Genes by Single Transgenes. Down-Regulation of Three Unrelated Lignin Biosynthetic Genes in Tobacco," Plant Physiol. 128(3):844-853.

Alam et al. (1999) "Transgenic Insect-Resistant Maintainer Line (IR68899B) for Improvement of Hybrid Rice," Plant Cell Reports 18:572-575.

Altschul et al. (1997) "Gapped BLAST and PSI-BLAST: a New Generation of Protein Database Search Programs," Nucleic Acids Res 25(17):3389-3402.

Bairoch et al. (1994) "PROSITE: Recent Developments," Nuc. Acids Res. 22(17):3583-3589.

Bajaj et al. (2006) "A High Throughput *Agrobacterium tumefaciens*-Mediated Transformation Method for Functional Genomics of Perennial Ryegrass (*Lolium perenne* L.)," Plant Cell Rep. 25:651-659.

Baxevanis, A.D. (2001) "The Molecular Biology Database Collection: an updated compilation of biological database resources," Nucleic Acids Research 29(1):1-10.

Birch, R.G. (1997) "Plant Transformation: Problems and Strategies for Practical Application," Ann Rev Plant Phys Plant Mol Biol 48:297-326.

Bolton et al. (1962) "A General Method for the Isolation of RNA Complementary to DNA," PNAS 48:1390-1397.

Bowie et al. (1990) "Deciphering the Message in Protein Sequences: Tolerance to Amino Acid Substitutions," Science 247:1306-1310.

De Carvalho Niebel et al. (1995) "Post Transcriptional Cosuppression of β-1,3-Glucanase Genes Does Not Affect Accumulation of Transgene Nuclear mRNA," Plant Cell 7:347-358.

Degenhardt et al. (1994) "Two 10-bp Regions are Critical for Phytochrome Regulation of a *Lemna gibba Lhcb* Gene Promoter," Plant Cell 6(8):1123-1134.

Falquet et al. (2002) "The PROSITE Database, Its Status in 2002," Nucleic Acids Res. 30(1):235-238.

Feng and Doolittle (1987) "Progressive Sequence Alignment as a Prerequisite to Correct Phylogenetic Trees," J. Mol. Evol. 25:351-360.

Frohman, M.A. (1993) "Rapid Amplification of Complementary DNA Ends for Generation of Full-Length Complementary DNAs: Thermal RACE," Methods Enzymol. 218:340-356.

Ghosh D. (2000) "Object-Oriented Transcription Factors Database (ooTFD)," Nucleic Acids Research 28:308-310.

Giesen et al. (1998) "A Formula for Thermal Stability (Tm) Prediction of PNA/DNA Duplexes," Nucleic Acids Res. 26(21):5004-5006.

Hashimoto et al. (2004) "5'-End SAGE for the Analysis of Transcriptional Start Sites," Nature Biotechnology 22(9):1146-1149.

Herrera-Estrella et al. (1983) "Expression of Chimaeric Genes Transferred Into Plant Cells Using a Ti-Plasmid-Derived Vector," Nature 303:209-213.

Hofmann et al. (1999) "The PROSITE Database, Its Status in 1999," Nucleic Acids Res. 27(1):215-219.

Horsch et al. (1985) "A Simple and General Method for Transferring Genes into Plants," Science 227:1229-1231 with correction of authorship.

Huang, X. (1994) "On Global Sequence Alignment. Computer Applications in the Biosciences," 10(3):227-235.

Jefferson et al. (1987) "GUS Fusions: ,B-glucuronidase as a Sensitive and Versatile Gene Fusion Marker in Higher Plants," EMBO 6:3901-3907.

Jones et al. (1998) "The Effect of Chimeric Transgene Architecture on Co-Ordinated Gene Silencing," Planta 204:499-505.

Krens et al. (1997) "Transgenic Caraway, *Carum carvi* L.: a Model Species for Metabolic Engineering," Plant Cell Reports 17:39-43.

Kumar et al. (1996) "Potato Plants Expressing Antisense and Sense S-Adenosylmethionine Decarboxylase (SAMDC) Transgenes Show Altered Levels of Polyamines and Ethylene: Antisense Plants Display Abnormal Phenotypes," The Plant J. 9(2):147-158.

Lee et al. (2010) "Validation of Reference Genes for Quantitative RT-PCR Studies of Gene Expression in Perennial Ryegrass (*Lolium perenne* L.)," BMC Molecular Biology 11:8, 14 pp.

Li et al. (1996) "Genetic Transformation of Cassava (*Manihot esculenta* Crantz)," Nature Biotechnology 14:736-740.

Llave et al. (2002) "Cleavage of *Scarecrow-like* mRNA Targets Directed by a Class of *Arabidopsis* miRNA," Science 297:2053-2056.

McIntyre et al. (1996) "Strategies for the Suppression of Peroxidase Gene Expression in Tobacco. I. Designing efficient ribozymes," Transgenic Research 5:257-262.

Michelmore et al. (1987) "Transformation of Lettuce (*Lactuca sativa*) Mediated by *Agrobacterium tumefaciens*," Plant Cell Reports 6:439-442.

Napoli et al. (1990) "Introduction of a Chimeric Chalcone Synthase Gene into Petunia Results in Reversible Co-Suppression of Homologous Genes in trans," The Plant Cell 2:279-289.

Needleman et al. (1970) "A General Method Applicable to the Search for Similarities in the Amino Acid Sequence of Two Proteins," J. Mol. Biol. 48:443-453.

Nielsen et al. (Dec. 6, 1991) "Sequence-Selective Recognition of DNA by Strand Displacement with a Thymine-Substituted Polyamide," Science 254(5037):1497-1500.

Niu et al. (1998) "Transgenic Peppermint (*Mentha* x *piperita* L.) Plants Obtained by Cocultivation with *Agrobacterium tumefaciens*," Plant Cell Reports 17:165-171.

Notredame et al. (2000) "T-Coffee: A Novel Method for Fast and Accurate Multiple Sequence Alignment," J. Mol. Biol. 302:205-217.

Ortiz et al. (1996) "Hygromycin Resistance as an Efficient Selectable Marker for Wheat Stable Transformation," Plant Cell Reports 15:877-881.

Pena et al. (1995) "High Efficiency *Agrobacterium*-Mediated Transformation and Regeneration of Citrus," Plant Science 104:183-191.

Rice et al. (Jun. 2000) EMBOSS: The European Molecular Biology Open Software Suite, Trends in Genetics 16(6):276-277.

Schrott, M. (1995) "Selectable Marker and Reporter Genes," In: Gene Transfer to Plants (Potrykus, T., Spangenberg. Eds) Springer Verlag. Berline, pp. 325-336.

Tatusova et al. (1999) "BLAST 2 Sequences, a New Tool for Comparing Protein and Nucleotide Sequences", FEMS Microbiol Lett. 174:247-250.

(56) References Cited

OTHER PUBLICATIONS

Thompson et al. (1994) "CLUSTAL W: Improving the Sensitivity of Progressive Multiple Sequence Alignment Through Sequence Weighting, Position-Specific Gap Penalties and Weight Matrix Choice," Nucleic Acids Research 22:4673-4680.

Triglia et al. (1988) "A Procedure for In Vitro Amplification of DNA Segments That Lie Outside the Boundaries of Known Sequences," Nucleic Acids Res. 16(16):8186.

Wheeler et al. (2001) "Database Resources of the National Center for Biotechnology Information," Nucleic Acids Research 29(1):11-16.

Mishra et al., 2009, "Role of ethylene responsive factors (ERFs) in abiotic stress mediated signalling in plants", E Journal of Biological Sciences 1(1) 133-146.

Oh et al., 2009, "Overexpression of the Transcription Factor AP37 in Rice Improves Grain Yield under Drought Conditions," Plant Physiology 150 (3): 1368-1379.

Sakuma Y, Liu Q, Dubouzet JG, Abe H, Shinozaki K, Yamaguchi-Shinozaki K, 2002, "DNA-binding specificity of the ERF/AP2 domain of *Arabidopsis* DREBs, transcription factors involved in dehydration- and cold-inducible gene expression", Biochemical and Biophysical Research Communications 290: 998-1009.

* cited by examiner

SEQUENCE LISTING

<160> NUMBER OF SEQ ID NOS: 57

<210> SEQ ID NO 1
<211> LENGTH: 250
<212> TYPE: PRT
<213> ORGANISM: Lolium perenne

<400> SEQUENCE: 1

Met Ala Pro Arg Thr Ser Glu Lys Ala Ala Ala Ala Ala Pro Ser
1               5                   10                  15

Ala Thr Ala Ala Thr Gly Leu Ala Leu Gly Val Gly Gly Gly Gly
                20                  25                  30

```
Gly Gly Gly Val Gly Thr His Phe Arg Gly Val Arg Lys Arg Pro Trp
            35                  40                  45
Gly Arg Tyr Ala Ala Glu Ile Arg Asp Pro Ala Lys Lys Ser Arg Val
 50                  55                  60
Trp Leu Gly Thr Tyr Asp Thr Ala Glu Glu Ala Ala Arg Ala Tyr Asp
 65                  70                  75                  80
Ala Ala Ala Arg Glu Tyr Arg Gly Ser Lys Ala Lys Thr Asn Phe Pro
                 85                  90                  95
Leu Phe Pro Ser Ala Leu Ala Thr Ala Val Pro Val Gly Ala Gly Gly
                100                 105                 110
Asp Gly Ser Arg Ser Ser Asn Ser Ser Thr Val Glu Ser Phe Gly Gly
                115                 120                 125
Asp Val Gln Ala Pro Met Gln Ala Met Pro Leu Pro Pro Ala Ser Leu
130                 135                 140
Glu Leu Asp Leu Phe His Arg Ala Ala Asn Ala Ala Gly Gly Ala Gly
145                 150                 155                 160
Ala Gly Val Arg Phe Pro Phe Ser Gly Tyr Pro Val Ser His Pro Phe
                165                 170                 175
Tyr Phe Phe Gly Gln Ala Ala Ala Ala Ala Ala Gly Cys His Val
                180                 185                 190
Tyr Gly Ser Ser Met Pro Pro Gln Val Thr Val Ala Ala Val Ser Gln
                195                 200                 205
Ser Asp Ser Gly Ser Ser Ser Val Val Asp Leu Ala Pro Ser Pro Pro
                210                 215                 220
Pro Ala Ala Ala Ser Ala Gln Arg Ala Pro Val Asp Phe Asp Leu Asp
225                 230                 235                 240
Leu Asn Cys Pro Pro Pro Ala Glu Leu Leu
                245                 250

<210> SEQ ID NO 2
<211> LENGTH: 236
<212> TYPE: PRT
<213> ORGANISM: Oryza sativa

<400> SEQUENCE: 2

Met Ala Pro Arg Thr Ser Asp Lys Thr Met Ser Pro Ala Ala Ala Ala
 1               5                  10                  15
Thr Gly Leu Ala Leu Gly Val Gly Val Ala Gly Ala Ala Ala Val
                 20                  25                  30
Gly Thr Gly Gln His Phe Arg Gly Val Arg Lys Arg Pro Trp Gly Arg
            35                  40                  45
Tyr Ala Ala Glu Ile Arg Asp Pro Ala Lys Lys Ser Arg Val Trp Leu
 50                  55                  60
Gly Thr Phe Asp Thr Ala Glu Glu Ala Ala Arg Ala Tyr Asp Ala Ala
 65                  70                  75                  80
Ala Arg Glu Tyr Arg Gly Ala Lys Ala Lys Thr Asn Phe Pro Tyr Pro
                 85                  90                  95
Asn Gly Ala Pro Ala Ala Gly Val Asn Ser Gly Ser Ser Asn Ser Ser
                100                 105                 110
Thr Val Glu Ser Phe Gly Ser Asp Val Gln Ala Pro Met Lys Ala Met
                115                 120                 125
Pro Ile Pro Pro Ser Leu Glu Leu Asp Leu Phe His Arg Ala Ala Ala
130                 135                 140
Ala Ala Ala Gly Ala Gly Gly Met Arg Phe Pro Phe Glu Gly Tyr
145                 150                 155                 160
```

```
Pro Val Ser His Pro Tyr Tyr Phe Phe Gly Gln Ala Ala Ala Ala
            165                 170                 175

Ala Ala Ser Gly Cys Arg Met Leu Lys Ile Ala Pro Ala Pro Val Thr
            180                 185                 190

Val Ala Ala Leu Ala Gln Ser Asp Ser Asp Ser Ser Ile Val Asp
        195                 200                 205

Leu Ala Pro Ser Pro Pro Ala Ala Leu Ala Lys Lys Ala Ile Ala Phe
210                 215                 220

Asp Leu Asp Leu Asn Cys Pro Pro Met Glu Val
225                 230                 235

<210> SEQ ID NO 3
<211> LENGTH: 235
<212> TYPE: PRT
<213> ORGANISM: Oryza sativa

<400> SEQUENCE: 3

Met Ala Pro Arg Ala Ala Thr Val Glu Lys Val Ala Val Ala Pro Pro
1               5                   10                  15

Thr Gly Leu Gly Leu Gly Val Gly Gly Val Gly Ala Gly Gly Pro
            20                  25                  30

His Tyr Arg Gly Val Arg Lys Arg Pro Trp Gly Arg Tyr Ala Ala Glu
            35                  40                  45

Ile Arg Asp Pro Ala Lys Lys Ser Arg Val Trp Leu Gly Thr Tyr Asp
        50                  55                  60

Thr Ala Glu Glu Ala Ala Arg Ala Tyr Asp Ala Ala Arg Glu Phe
65                  70                  75                  80

Arg Gly Ala Lys Ala Lys Thr Asn Phe Pro Phe Ala Ser Gln Ser Met
                85                  90                  95

Val Gly Cys Gly Gly Ser Pro Ser Ser Asn Ser Thr Val Asp Thr Gly
            100                 105                 110

Gly Gly Gly Val Gln Thr Pro Met Arg Ala Met Pro Leu Pro Pro Thr
            115                 120                 125

Leu Asp Leu Asp Leu Phe His Arg Ala Ala Ala Val Thr Ala Val Ala
130                 135                 140

Gly Thr Gly Val Arg Phe Pro Phe Arg Gly Tyr Pro Val Ala Arg Pro
145                 150                 155                 160

Ala Thr His Pro Tyr Phe Phe Tyr Glu Gln Ala Ala Ala Ala Ala
            165                 170                 175

Ala Glu Ala Gly Tyr Arg Met Met Lys Leu Ala Pro Val Thr Val
            180                 185                 190

Ala Ala Val Ala Gln Ser Asp Ser Asp Ser Ser Val Val Asp Leu
        195                 200                 205

Ala Pro Ser Pro Pro Ala Val Thr Ala Asn Lys Ala Ala Phe Asp
210                 215                 220

Leu Asp Leu Asn Arg Pro Pro Val Glu Asn
225                 230                 235

<210> SEQ ID NO 4
<211> LENGTH: 239
<212> TYPE: PRT
<213> ORGANISM: Stylosanthes hamata

<400> SEQUENCE: 4

Met Ala Pro Arg Glu Lys Thr Pro Ala Val Lys Val Asn Ala Gly Val
1               5                   10                  15
```

```
Lys Glu Val His Phe Arg Gly Val Arg Lys Arg Pro Trp Gly Arg Tyr
             20                  25                  30

Ala Ala Glu Ile Arg Asp Pro Gly Lys Lys Ser Arg Val Trp Leu Gly
         35                  40                  45

Thr Phe Asp Thr Ala Glu Asp Ala Ala Arg Ala Tyr Asp Ala Ala Ala
 50                  55                  60

Arg Glu Phe Arg Gly Pro Lys Ala Lys Thr Asn Phe Pro Phe Pro Asp
 65                  70                  75                  80

Ser Asp Asp Ile Asn Ser Asn Asn Asn Ile Val Val Lys Asn
                 85                  90                  95

Asn Asn Arg Ser Pro Ser Gln Ser Ser Thr Val Glu Ser Ser Arg
             100                 105                 110

Asp Arg Asp Ser Tyr Ser Ala Ala Ala Ala Thr Ala Val Ala Asp
             115                 120                 125

Ser Ser Pro Leu Asp Leu Asn Leu Ala Pro Ala Gly Ala Gly Phe Ala
 130                 135                 140

Gly Ser Ile Arg Phe Pro Phe Gln Gln Pro Phe Ala Val Phe Pro Gly
145                 150                 155                 160

Gly Met Pro Ala Ala Lys Gln Ala Leu Tyr Leu Asp Ala Val Leu Arg
                 165                 170                 175

Ala Ser Met Ala Ser His Gly Gln Phe Gly Phe Gly Tyr Asn Arg Pro
             180                 185                 190

Ala Ala Ala Ala Gly Ala Gln Ser Asp Ser Asp Ser Ser Ser Val
             195                 200                 205

Ile Asp Leu Asn Gln Asn Gly Asp Val Ala Lys Asn Asn Gly Arg
 210                 215                 220

Gly Leu Val Leu Asp Leu Asn Glu Pro Pro Gln Glu Met Ala
225                 230                 235

<210> SEQ ID NO 5
<211> LENGTH: 220
<212> TYPE: PRT
<213> ORGANISM: Vitis aestivalis

<400> SEQUENCE: 5

Met Ala Pro Arg Asp Lys Pro Thr Gly Val Thr Ala Gly Ala Thr Gly
1               5                   10                  15

Asn Lys Glu Ile Arg Tyr Arg Gly Val Arg Lys Arg Pro Trp Gly Arg
             20                  25                  30

Tyr Ala Ala Glu Ile Arg Asp Pro Gly Lys Lys Ser Arg Val Trp Leu
         35                  40                  45

Gly Thr Phe Asp Thr Ala Glu Glu Ala Ala Arg Ala Tyr Asp Ala Ala
 50                  55                  60

Ala Arg Glu Phe Arg Gly Ala Lys Ala Lys Thr Asn Phe Pro Ser Pro
 65                  70                  75                  80

Thr Asp Leu Ala Ala Ala Ala Thr Thr Ala Asn Arg Ser Pro Ser
                 85                  90                  95

Gln Ser Ser Thr Val Glu Ser Ser Arg Glu Ala Leu Ser Pro Gly
             100                 105                 110

Ala Ile Ala Gly Pro Pro Ala Leu Asp Leu Asn Leu Ser His Pro Ala
             115                 120                 125

Ala Ala Gly Gln Phe Ser Ala Val Arg Tyr Pro Ala Val Gly Val Phe
 130                 135                 140

Pro Ile Ala Gln Pro Leu Phe Phe Phe Glu Pro Phe Ser Arg Pro Glu
```

-continued

```
              145                 150                 155                 160

Lys Pro Lys Thr His Arg Asp Met Phe Asp Leu Asp Arg Ala Val Ala
                165                 170                 175

Asp Phe His Pro Ala Ile Ala Gly Ser Val His Ser Asp Ser Asp Ser
            180                 185                 190

Ser Ser Val Val Asp Phe Asn Tyr His Asp Arg Ser Thr Arg Leu Leu
            195                 200                 205

Asn Leu Asp Leu Asn His Pro Pro Ala Glu Val Ala
        210                 215                 220

<210> SEQ ID NO 6
<211> LENGTH: 238
<212> TYPE: PRT
<213> ORGANISM: Stylosanthes hamata

<400> SEQUENCE: 6

Met Ala Pro Arg Glu Lys Thr Pro Ala Val Lys Val Asn Gly Lys Ser
1               5                   10                  15

Asn Ala Gly Val Lys Glu Val His Phe Arg Gly Val Arg Lys Arg Pro
            20                  25                  30

Trp Gly Arg Tyr Ala Ala Glu Ile Arg Asp Pro Gly Lys Lys Ser Arg
        35                  40                  45

Val Trp Leu Gly Thr Phe Asp Thr Ala Glu Asp Ala Ala Arg Ala Tyr
    50                  55                  60

Asp Ala Ala Ala Arg Glu Phe Arg Gly Pro Lys Ala Lys Thr Asn Phe
65                  70                  75                  80

Pro Phe Pro Asp Ser Asp Ile Asn Asn Asn Ile Val Val
                85                  90                  95

Lys Asn Asn Asn Arg Ser Pro Ser Gln Ser Ser Thr Val Glu Ser Ser
                100                 105                 110

Ser Arg Asp Arg Asp Ser Tyr Ser Ala Ala Ala Thr Ala Val Ala
            115                 120                 125

Asp Ser Ser Pro Leu Asp Leu Asn Leu Ala Pro Gln Glu Leu Asp Ser
    130                 135                 140

Pro Asp Pro Phe Gly Ser His Ser Thr Gln Pro Phe Ala Val Phe Pro
145                 150                 155                 160

Gly Gly Met Pro Ala Ala Lys Gln Ala Leu Tyr Leu Asp Ala Val Leu
                165                 170                 175

Arg Ala Ser Met Ala Ser His Gly Gln Phe Gly Phe Gly Tyr Asn Arg
            180                 185                 190

Pro Ala Ala Ala Gly Ala Gln Ser Asp Ser Asp Ser Ser Val Ile
        195                 200                 205

Asp Leu Asn Gln Asn Glu Gly Asp Val Ala Lys Asn Asn Gly Arg Gly
    210                 215                 220

Leu Val Leu Asp Leu Asn Glu Pro Pro Gln Glu Met Ala
225                 230                 235

<210> SEQ ID NO 7
<211> LENGTH: 195
<212> TYPE: PRT
<213> ORGANISM: Thellungiella halophila

<400> SEQUENCE: 7

Met Thr Lys Met Gly Phe Lys Pro Asp Ser Asn Pro Ser Pro Asn Pro
1               5                   10                  15

Asn Glu Ser Asn Ala Lys Glu Ile Arg Tyr Arg Gly Val Arg Lys Arg
```

```
            20                  25                  30
Pro Trp Gly Arg Tyr Ala Ala Glu Ile Arg Asp Pro Gly Lys Lys Thr
        35                  40                  45

Arg Val Trp Leu Gly Thr Phe Asp Thr Ala Gln Gln Ala Ala Arg Ala
    50                  55                  60

Tyr Asp Ala Ala Ala Arg Glu Phe Arg Gly Ala Lys Ala Lys Thr Asn
65                  70                  75                  80

Phe Pro Thr Phe Leu Glu Leu Asn Ala Ala Lys Asp Gly Gly Phe Ala
                85                  90                  95

Arg Ser Pro Ser Gln Ser Ser Thr Val Asp Ser Val Ser Pro Thr Ser
            100                 105                 110

Ala Arg Leu Val Thr Pro Pro Gln Leu Glu Leu Ser Leu Gly Gly Gly
        115                 120                 125

Gly Gly Gly Ala Cys Tyr Gln Ile Pro Val Ala Arg Arg Pro Val Tyr
    130                 135                 140

Phe Tyr Asn Met Thr Thr Phe Pro Ala Ala Ala Ala Thr Cys Gly
145                 150                 155                 160

Val Gln Ser Glu Ser Asp Ser Ser Val Val Asp Phe Glu Cys Gly
                165                 170                 175

Ala Glu Lys Lys Tyr Arg Pro Leu Asp Leu Asp Leu Asn Leu Ala Pro
            180                 185                 190

Pro Ala Glu
        195

<210> SEQ ID NO 8
<211> LENGTH: 249
<212> TYPE: PRT
<213> ORGANISM: Vitis aestivalis

<400> SEQUENCE: 8

Met Ala Pro Lys Glu Lys Val Ala Gly Val Lys Pro Ser Ala Asn Ala
1               5                   10                  15

Lys Glu Val His Phe Arg Gly Val Arg Lys Arg Pro Trp Gly Arg Tyr
            20                  25                  30

Ala Ala Glu Ile Arg Asp Pro Gly Lys Lys Ser Arg Val Trp Leu Gly
        35                  40                  45

Thr Phe Asp Thr Ala Glu Glu Ala Ala Lys Ala Tyr Asp Ser Ala Ala
    50                  55                  60

Arg Glu Phe Arg Gly Ala Lys Ala Lys Thr Asn Phe Pro Leu Val Ser
65                  70                  75                  80

Glu Asn Leu Asn Asn Asn Gln Ser Pro Ser Gln Ser Ser Thr Val
                85                  90                  95

Glu Ser Ser Arg Glu Gly Phe Ser Pro Ala Leu Met Val Asp Ser
            100                 105                 110

Ser Pro Leu Asp Leu Asn Leu Leu His Gly Gly Val Gly Val Gly
        115                 120                 125

Val Gly Val Gly Val Gly Ala Ala Gly Tyr Ala Thr Ala Met Arg
    130                 135                 140

Phe Pro Phe Gln His His Gln Phe Gln Val Ser Ser Pro Ser Pro Ala
145                 150                 155                 160

Ala Gly Ile Val Pro Thr Gly Leu Pro Ala Ala Asn His Leu Phe
                165                 170                 175

Tyr Phe Asp Ala Met Leu Arg Thr Gly Arg Val Asn Gln Asp Phe Gln
            180                 185                 190
```

```
Arg Leu Arg Phe Asp Arg Ala Ala Ser Asp Phe Arg Ala Ala Leu Thr
            195                 200                 205

Gly Gly Val Gln Ser Asp Ser Asp Ser Ser Val Val Asp Leu Asn
210                 215                 220

His Asn Asp Leu Lys Pro Arg Ala Arg Val Leu Ile Asp Leu Asp Leu
225                 230                 235                 240

Asn Arg Pro Pro Pro Glu Ile Ala
                245

<210> SEQ ID NO 9
<211> LENGTH: 222
<212> TYPE: PRT
<213> ORGANISM: Arabidopsis thaliana

<400> SEQUENCE: 9

Met Ala Lys Met Gly Leu Lys Pro Asp Pro Ala Thr Thr Asn Gln Thr
1               5                   10                  15

His Asn Asn Ala Lys Glu Ile Arg Tyr Arg Gly Val Arg Lys Arg Pro
            20                  25                  30

Trp Gly Arg Tyr Ala Ala Glu Ile Arg Asp Pro Gly Lys Lys Thr Arg
        35                  40                  45

Val Trp Leu Gly Thr Phe Asp Thr Ala Glu Glu Ala Ala Arg Ala Tyr
50                  55                  60

Asp Thr Ala Ala Arg Asp Phe Arg Gly Ala Lys Ala Lys Thr Asn Phe
65                  70                  75                  80

Pro Thr Phe Leu Glu Leu Ser Asp Gln Lys Val Pro Thr Gly Phe Ala
                85                  90                  95

Arg Ser Pro Ser Gln Ser Ser Thr Leu Asp Cys Ala Ser Pro Pro Thr
            100                 105                 110

Leu Val Val Pro Ser Ala Thr Ala Gly Asn Val Pro Pro Gln Leu Glu
        115                 120                 125

Leu Ser Leu Gly Gly Gly Gly Gly Ser Cys Tyr Gln Ile Pro Met
    130                 135                 140

Ser Arg Pro Val Tyr Phe Leu Asp Leu Met Gly Ile Gly Asn Val Gly
145                 150                 155                 160

Arg Gly Gln Pro Pro Pro Val Thr Ser Ala Phe Arg Ser Pro Val Val
                165                 170                 175

His Val Ala Thr Lys Met Ala Cys Gly Ala Gln Ser Asp Ser Asp Ser
            180                 185                 190

Ser Ser Val Val Asp Phe Glu Gly Gly Met Glu Lys Arg Ser Gln Leu
        195                 200                 205

Leu Asp Leu Asp Leu Asn Leu Pro Pro Pro Ser Glu Gln Ala
    210                 215                 220

<210> SEQ ID NO 10
<211> LENGTH: 246
<212> TYPE: PRT
<213> ORGANISM: Cucumis sativus

<400> SEQUENCE: 10

Met Ala Pro Arg Glu Lys Ala Val Ala Val Lys Pro Ser Val Gly Asn
1               5                   10                  15

Val Lys Glu Val His Phe Arg Gly Val Arg Lys Arg Pro Trp Gly Arg
            20                  25                  30

Tyr Ala Ala Glu Ile Arg Asp Pro Ser Lys Lys Ser Arg Val Trp Leu
        35                  40                  45
```

```
Gly Thr Phe Asp Thr Ala Glu Glu Ala Ala Arg Ala Tyr Asp Ser Ala
    50                  55                  60

Ala Arg Asp Phe Arg Gly Val Lys Ala Lys Thr Asn Phe Pro Leu Pro
 65                  70                  75                  80

Ser Asp Asp Gln Leu Leu Asn Leu Asn Asn Lys Ile Asn Asn Ile Asn
                 85                  90                  95

Asn Asn Gln Ser Pro Ser Gln Ser Ser Thr Val Glu Ser Ser Ser Arg
            100                 105                 110

Glu Gln Ala Leu Met Val Asp Ser Ser Pro Leu Asn Leu Asn Leu Gly
            115                 120                 125

His Gly Ile Gly Gly Leu Thr Asn Ala Gly Pro Ile Ser Phe Pro Phe
        130                 135                 140

Gln Arg Tyr Gln Ile Pro Met Ile Gly Glu Val Phe Thr Arg Gly Ile
145                 150                 155                 160

Pro Pro Ser Asn His Val Leu Tyr Phe Asp Ala Ala Leu Arg Ala Gly
                165                 170                 175

Met Ile Asn Ser His Pro Asn Gln Arg Leu His Phe Asp Arg Ile Arg
            180                 185                 190

Glu Ala Val Ser Asp Phe Arg Arg Glu Phe Ala Gly Ser Gly Val Gln
        195                 200                 205

Ser Asp Ser Asp Ser Ser Val Val Asp Met Asn Gly Gln Asp Leu
210                 215                 220

Lys Pro Arg Gly Gly Ser Gly Gly Arg Leu Asp Leu Asp Leu Asn Phe
225                 230                 235                 240

Pro Pro Pro Glu Ser Ala
            245

<210> SEQ ID NO 11
<211> LENGTH: 222
<212> TYPE: PRT
<213> ORGANISM: Oryza sativa

<400> SEQUENCE: 11

Met Ala Pro Arg Asn Ala Ala Glu Ala Val Ala Val Ala Val Ala Glu
  1               5                  10                  15

Gly Gly Gly Ala Gly Met Glu Pro Arg Phe Arg Gly Val Arg Lys Arg
             20                  25                  30

Pro Trp Gly Arg Tyr Ala Ala Glu Ile Arg Asp Pro Ala Arg Lys Ala
         35                  40                  45

Arg Val Trp Leu Gly Thr Phe Asp Thr Ala Glu Ala Ala Ala Arg Ala
 50                  55                  60

Tyr Asp Ser Ala Ala Leu His Phe Arg Gly Pro Lys Ala Lys Thr Asn
 65                  70                  75                  80

Phe Pro Val Ala Phe Ala His Ala His His Ala Pro Pro Pro Pro
                 85                  90                  95

Leu Pro Lys Ala Ala Ala Leu Ala Val Val Ser Pro Thr Ser Ser Thr
            100                 105                 110

Val Glu Ser Ser Ser Arg Asp Thr Pro Ala Ala Ala Pro Val Ala Ala
            115                 120                 125

Ala Ala Lys Ala Gln Val Pro Ala Ser Pro Ser Leu Asp Leu Ser Leu
            130                 135                 140

Gly Met Ser Ala Met Val Ala Ala Gln Pro Phe Leu Phe Leu Asp Pro
145                 150                 155                 160

Arg Val Ala Val Thr Val Ala Val Ala Ala Pro Val Pro Arg Arg Pro
                165                 170                 175
```

```
Ala Val Val Ser Val Lys Lys Glu Val Ala Arg Leu Asp Glu Gln Ser
            180                 185                 190

Asp Thr Gly Ser Ser Ser Val Asp Ala Ser Pro Ala Val Gly
        195                 200                 205

Val Gly Leu Asp Leu Asn Leu Pro Pro Ile Glu Glu Ala
    210                 215                 220

<210> SEQ ID NO 12
<211> LENGTH: 227
<212> TYPE: PRT
<213> ORGANISM: Nicotiana sylvestris

<400> SEQUENCE: 12

Met Ala Val Lys Asn Lys Val Ser Asn Gly Asp Leu Lys Gly Gly Asn
1               5                   10                  15

Val Lys Thr Asn Gly Val Lys Glu Val His Tyr Arg Gly Val Arg Lys
            20                  25                  30

Arg Pro Trp Gly Arg Tyr Ala Ala Glu Ile Arg Asp Pro Gly Lys Lys
        35                  40                  45

Ser Arg Val Trp Leu Gly Thr Phe Asp Thr Ala Glu Glu Ala Ala Lys
    50                  55                  60

Ala Tyr Asp Thr Ala Ala Arg Glu Phe Arg Gly Pro Lys Ala Lys Thr
65                  70                  75                  80

Asn Phe Pro Leu Pro Ser Glu Asn Gln Ser Thr Ser His Ser Ser Thr
                85                  90                  95

Met Glu Ser Ser Ser Gly Glu Thr Gly Ile His Ala Pro Pro His Ala
            100                 105                 110

Pro Leu Glu Leu Asp Leu Thr Arg Arg Leu Gly Ser Val Ala Ala Asp
        115                 120                 125

Gly Gly Asp Asn Cys Arg Arg Ser Gly Glu Val Gly Tyr Pro Ile Phe
    130                 135                 140

His Gln Gln Pro Thr Val Ala Val Leu Pro Asn Gly Gln Pro Val Leu
145                 150                 155                 160

Leu Phe Asp Ser Leu Trp Arg Pro Gly Val Val Asn Arg Pro Gln Pro
                165                 170                 175

Tyr His Val Met Pro Met Ala Met Gly Phe Asn Gly Val Asn Ala Gly
            180                 185                 190

Val Asp Pro Thr Val Ser Asp Ser Ser Val Val Glu Glu Asn Gln
        195                 200                 205

Tyr Asp Gly Lys Arg Gly Ile Asp Leu Asp Leu Asn Leu Ala Pro Pro
    210                 215                 220

Thr Glu Phe
225

<210> SEQ ID NO 13
<211> LENGTH: 225
<212> TYPE: PRT
<213> ORGANISM: Nicotiana tabacum

<400> SEQUENCE: 13

Met Ala Val Lys Asn Lys Val Ser Asn Gly Asn Leu Lys Gly Gly Asn
1               5                   10                  15

Val Lys Thr Asp Gly Val Lys Glu Val His Tyr Arg Gly Val Arg Lys
            20                  25                  30

Arg Pro Trp Gly Arg Tyr Ala Ala Glu Ile Arg Asp Pro Gly Lys Lys
        35                  40                  45
```

```
Ser Arg Val Trp Leu Gly Thr Phe Asp Thr Ala Glu Glu Ala Ala Lys
    50                  55                  60

Ala Tyr Asp Thr Ala Ala Arg Glu Phe Arg Gly Pro Lys Ala Lys Thr
 65                  70                  75                  80

Asn Phe Pro Ser Pro Thr Glu Asn Gln Ser Pro Ser His Ser Ser Thr
                 85                  90                  95

Val Glu Ser Ser Ser Gly Glu Asn Gly Val His Ala Pro Pro His Ala
            100                 105                 110

Pro Leu Glu Leu Asp Leu Thr Arg Arg Leu Gly Ser Val Ala Ala Asp
        115                 120                 125

Gly Gly Asp Asn Cys Arg Arg Ser Gly Glu Val Gly Tyr Pro Ile Phe
    130                 135                 140

His Gln Gln Pro Thr Val Ala Val Leu Pro Asn Gly Gln Pro Val Leu
145                 150                 155                 160

Leu Phe Asp Ser Leu Trp Arg Ala Gly Val Val Asn Arg Pro Gln Pro
                165                 170                 175

Tyr His Val Thr Pro Met Gly Phe Asn Gly Val Asn Ala Gly Val Gly
            180                 185                 190

Pro Thr Val Ser Asp Ser Ser Ala Val Glu Glu Asn Gln Tyr Asp
        195                 200                 205

Gly Lys Arg Gly Ile Asp Leu Asp Leu Asn Leu Ala Pro Pro Met Glu
    210                 215                 220

Phe
225

<210> SEQ ID NO 14
<211> LENGTH: 213
<212> TYPE: PRT
<213> ORGANISM: Arabidopsis thaliana

<400> SEQUENCE: 14

Met Ala Lys Met Gly Leu Lys Pro Asp Pro Ala Thr Thr Asn Gln Thr
  1               5                  10                  15

His Asn Asn Ala Lys Glu Ile Arg Tyr Arg Gly Val Arg Lys Arg Pro
             20                  25                  30

Trp Gly Arg Tyr Ala Ala Glu Ile Arg Asp Pro Gly Lys Lys Thr Arg
         35                  40                  45

Val Trp Leu Gly Thr Phe Asp Thr Ala Glu Glu Ala Ala Arg Ala Tyr
     50                  55                  60

Asp Thr Ala Ala Arg Asp Phe Arg Gly Ala Lys Ala Lys Thr Asn Phe
 65                  70                  75                  80

Pro Thr Phe Leu Glu Leu Ser Asp Gln Lys Val Pro Thr Gly Phe Ala
                 85                  90                  95

Arg Ser Pro Ser Gln Ser Ser Thr Leu Asp Cys Ala Ser Pro Pro Thr
            100                 105                 110

Leu Val Val Pro Ser Ala Thr Ala Gly Asn Val Pro Pro Gln Leu Glu
        115                 120                 125

Leu Ser Leu Gly Gly Gly Gly Gly Ser Cys Tyr Gln Ile Pro Met
    130                 135                 140

Ser Arg Pro Val Tyr Phe Leu Asp Leu Met Gly Ile Gly Asn Val Gly
145                 150                 155                 160

Arg Gly Gln Pro Pro Val Thr Ser Ala Phe Arg Ser Pro Val Val
                165                 170                 175

His Val Ala Thr Lys Met Ala Cys Gly Ala Gln Ser Asp Ser Asp Ser
```

```
                    180                 185                 190
Ser Ser Val Val Asp Phe Glu Gly Gly Met Glu Lys Arg Ser Gln Thr
            195                 200                 205

Val Arg Ser Arg Ser
            210

<210> SEQ ID NO 15
<211> LENGTH: 185
<212> TYPE: PRT
<213> ORGANISM: Arabidopsis thaliana

<400> SEQUENCE: 15

Met Pro Asn Ile Thr Met Gly Leu Lys Pro Asp Pro Val Ala Pro Thr
1               5                   10                  15

Asn Pro Thr His His Glu Ser Asn Ala Ala Lys Glu Ile Arg Tyr Arg
            20                  25                  30

Gly Val Arg Lys Arg Pro Trp Gly Arg Tyr Ala Ala Glu Ile Arg Asp
        35                  40                  45

Pro Val Lys Lys Thr Arg Val Trp Leu Gly Thr Phe Asp Thr Ala Gln
    50                  55                  60

Gln Ala Ala Arg Ala Tyr Asp Ala Ala Ala Arg Asp Phe Arg Gly Val
65                  70                  75                  80

Lys Ala Lys Thr Asn Phe Gly Val Ile Val Gly Ser Ser Pro Thr Gln
                85                  90                  95

Ser Ser Thr Val Val Asp Ser Pro Thr Ala Ala Arg Phe Ile Thr Pro
            100                 105                 110

Pro His Leu Glu Leu Ser Leu Gly Gly Gly Gly Ala Cys Arg Arg Lys
        115                 120                 125

Ile Pro Leu Val His Pro Val Tyr Tyr Tyr Asn Met Ala Thr Tyr Pro
    130                 135                 140

Lys Met Thr Thr Cys Gly Val Gln Ser Glu Ser Glu Thr Ser Ser Val
145                 150                 155                 160

Val Asp Phe Glu Gly Gly Ala Gly Lys Ile Ser Pro Pro Leu Asp Leu
                165                 170                 175

Asp Leu Asn Leu Ala Pro Pro Ala Glu
            180                 185

<210> SEQ ID NO 16
<211> LENGTH: 210
<212> TYPE: PRT
<213> ORGANISM: Lycopersicon esculentum

<400> SEQUENCE: 16

Met Ala Met Val Asn Leu Asn Gly Ile Ser Lys Glu Val His Tyr Arg
1               5                   10                  15

Gly Val Arg Lys Arg Pro Trp Gly Arg Tyr Ala Ala Glu Ile Arg Asp
            20                  25                  30

Pro Gly Lys Lys Ser Arg Val Trp Leu Gly Thr Phe Asp Thr Ala Glu
        35                  40                  45

Glu Ala Ala Arg Ala Tyr Asp Asn Ala Ala Arg Glu Phe Arg Gly Ala
    50                  55                  60

Lys Ala Lys Thr Asn Phe Pro Lys Leu Glu Met Glu Lys Glu Glu Asp
65                  70                  75                  80

Leu Lys Phe Ala Val Lys Asn Glu Ile Asn Arg Ser Pro Ser Gln Thr
                85                  90                  95

Ser Thr Val Glu Ser Ser Ser Pro Val Met Val Asp Ser Ser Ser Pro
```

```
                100             105             110
Leu Asp Leu Ser Leu Cys Gly Ser Ile Gly Gly Phe Asn His His Thr
        115                 120                 125

Val Lys Phe Pro Ser Ser Gly Gly Phe Thr Gly Ser Val Gln Ala
        130                 135                 140

Val Asn His Met Tyr Tyr Ile Glu Ala Leu Ala Arg Ala Gly Val Ile
145                 150                 155                 160

Lys Leu Glu Thr Asn Arg Lys Lys Thr Val Asp Tyr Leu Gly Gly
                165                 170                 175

Asp Ser Asp Ser Ser Thr Val Ile Asp Phe Met Arg Val Asp Val Lys
                180                 185                 190

Ser Thr Thr Ala Gly Leu Asn Leu Asp Leu Asn Phe Pro Pro Glu
                195                 200                 205

Asn Met
    210

<210> SEQ ID NO 17
<211> LENGTH: 222
<212> TYPE: PRT
<213> ORGANISM: Lycopersicon esculentum

<400> SEQUENCE: 17

Met Ala Pro Lys Glu Lys Ile Gly Ala Val Thr Ala Met Ala Met Val
1               5                   10                  15

Asn Leu Asn Gly Ile Ser Lys Glu Val His Tyr Arg Gly Val Arg Lys
                20                  25                  30

Arg Pro Trp Gly Arg Tyr Ala Ala Glu Ile Arg Asp Pro Gly Lys Lys
            35                  40                  45

Ser Arg Val Trp Leu Gly Thr Phe Asp Thr Ala Glu Glu Ala Ala Arg
    50                  55                  60

Ala Tyr Asp Asn Ala Ala Arg Glu Phe Arg Gly Ala Lys Ala Lys Thr
65                  70                  75                  80

Asn Phe Pro Lys Leu Glu Met Glu Lys Glu Glu Asp Leu Lys Phe Ala
                85                  90                  95

Val Lys Asn Glu Ile Asn Arg Ser Pro Gly Gln Thr Ser Thr Val Glu
                100                 105                 110

Ser Ser Ser Pro Val Met Val Asp Ser Ser Ser Pro Leu Asp Leu Ser
                115                 120                 125

Leu Cys Gly Ser Ile Gly Gly Phe Asn His His Thr Val Lys Phe Pro
        130                 135                 140

Ser Ser Gly Gly Gly Phe Thr Gly Ser Val Gln Ala Val Asn Arg Met
145                 150                 155                 160

Tyr Tyr Ile Glu Ala Leu Ala Arg Ala Gly Val Ile Lys Leu Glu Gln
                165                 170                 175

Ile Gly Arg Lys Arg Leu Asp Tyr Leu Gly Gly Asp Ser Asp Ser
            180                 185                 190

Ser Thr Val Ile Asp Phe Met Arg Val Asp Val Lys Ser Thr Thr Ala
        195                 200                 205

Gly Leu Asn Leu Asp Leu Asn Phe Pro Pro Glu Asn Met
    210                 215                 220

<210> SEQ ID NO 18
<211> LENGTH: 200
<212> TYPE: PRT
<213> ORGANISM: Arabidopsis thaliana
```

```
<400> SEQUENCE: 18

Met Ala Pro Arg Gln Ala Asn Gly Arg Ser Ile Ala Val Ser Glu Gly
1               5                   10                  15

Gly Gly Gly Lys Thr Met Thr Met Thr Thr Met Arg Lys Glu Val His
            20                  25                  30

Phe Arg Gly Val Arg Lys Arg Pro Trp Gly Arg Tyr Ala Ala Glu Ile
        35                  40                  45

Arg Asp Pro Gly Lys Lys Thr Arg Val Trp Leu Gly Thr Phe Asp Thr
50                  55                  60

Ala Glu Glu Ala Ala Arg Ala Tyr Asp Thr Ala Ala Arg Glu Phe Arg
65                  70                  75                  80

Gly Ser Lys Ala Lys Thr Asn Phe Pro Leu Pro Gly Glu Ser Thr Thr
                85                  90                  95

Val Asn Asp Gly Gly Glu Asn Asp Ser Tyr Val Asn Arg Thr Thr Val
            100                 105                 110

Thr Thr Ala Arg Glu Met Thr Arg Gln Arg Phe Pro Phe Ala Cys His
        115                 120                 125

Arg Glu Arg Lys Val Val Gly Gly Tyr Ala Ser Ala Gly Phe Phe Phe
130                 135                 140

Asp Pro Ser Arg Ala Ala Ser Leu Arg Ala Glu Leu Ser Arg Val Cys
145                 150                 155                 160

Pro Val Arg Phe Asp Pro Val Asn Ile Glu Leu Ser Ile Gly Ile Arg
                165                 170                 175

Glu Thr Val Lys Val Glu Pro Arg Arg Glu Leu Asn Leu Asp Leu Asn
            180                 185                 190

Leu Ala Pro Pro Val Val Asp Val
        195                 200

<210> SEQ ID NO 19
<211> LENGTH: 199
<212> TYPE: PRT
<213> ORGANISM: Oryza sativa

<400> SEQUENCE: 19

Met Arg Arg Gly Gly Ala Ala Glu Glu Asp Ala Glu Ala Ala Arg Phe
1               5                   10                  15

Arg Gly Val Arg Lys Arg Pro Trp Gly Arg Tyr Ala Ala Glu Ile Arg
            20                  25                  30

Asp Pro Ala Lys Lys Ala Arg Val Trp Leu Gly Thr Tyr Asp Ser Ala
        35                  40                  45

Glu Asp Ala Ala Arg Ala Tyr Asp Ala Ala Ala Arg Ala Leu Arg Gly
50                  55                  60

Ala Lys Ala Lys Thr Asn Phe Pro Leu Ser Leu Pro His Ala Gln Pro
65                  70                  75                  80

Gln Leu His His His His His His Leu Thr Tyr Pro Ala Ala
                85                  90                  95

Val Val Ala Ala Arg Pro Ala Thr Ser Ser Leu Ser Ser Thr Val Glu
            100                 105                 110

Ser Phe Gly Thr Arg Pro Arg Pro Val Leu Pro Pro Arg Pro Pro Pro
        115                 120                 125

Pro Pro Pro Ile Pro Asp Gly Asp Cys Arg Ser Asp Cys Gly Ser Ser
130                 135                 140

Ala Ser Val Val Asp Asp Asp Cys Ala Asp Ala Ala Ser Pro Ser
145                 150                 155                 160
```

```
Cys Arg Leu Pro Phe Gln Phe Asp Leu Asn Leu Pro Pro Gly Gly Gly
                165                 170                 175

Gly Gly Gly Gly Gly Gly Phe Gly Cys Ala Tyr Asp Asp Glu Glu Leu
            180                 185                 190

Arg Leu Thr Ala Leu Arg Leu
        195

<210> SEQ ID NO 20
<211> LENGTH: 218
<212> TYPE: PRT
<213> ORGANISM: Pisum sativum

<400> SEQUENCE: 20

Met Gly Arg Gly Gly Ala Thr Thr Ala Ala Ala Val Glu Pro Val
1               5                   10                  15

Phe Phe Lys Glu Pro Arg Tyr Arg Gly Val Arg Lys Arg Pro Trp Gly
            20                  25                  30

Arg Phe Ala Ala Glu Ile Arg Asp Pro Leu Lys Lys Ala Arg Val Trp
        35                  40                  45

Leu Gly Thr Phe Asp Thr Ala Glu Glu Ala Ala Arg Ala Tyr Asp Thr
    50                  55                  60

Ala Ala Arg Asn Leu Arg Gly Pro Lys Ala Lys Thr Asn Phe Pro Leu
65                  70                  75                  80

Ala Gln Pro Phe Tyr Gln Asn Pro Glu Ala Gly Asn Pro Phe Gly Glu
                85                  90                  95

Leu Arg Phe Tyr Ala Gly Gly Ala Gly Glu Gly Phe Gln Asp His Arg
            100                 105                 110

Arg Pro Thr Ser Ser Gly Met Ser Ser Thr Val Glu Ser Phe Gly Gly
        115                 120                 125

Pro Arg Pro Val Arg Pro Pro Met Pro Pro Ser Ala Val Thr Gly Arg
    130                 135                 140

Arg Tyr Pro Arg Thr Pro Pro Val Ala Pro Gly Asp Cys Arg Ser Asp
145                 150                 155                 160

Cys Asp Ser Ser Ser Ser Val Val Asp Asp Ala Asp Asn Asp Asn Ala
                165                 170                 175

Ala Ser Ser Thr Met Leu Ser Phe Lys Arg Gln Pro Leu Pro Phe Asp
            180                 185                 190

Leu Asn Ala Pro Pro Leu Glu Glu Gly Asp Val Ala Asn Gly Leu Gly
        195                 200                 205

Glu Asp Leu His Cys Thr Leu Leu Cys Leu
210                 215

<210> SEQ ID NO 21
<211> LENGTH: 204
<212> TYPE: PRT
<213> ORGANISM: Capsicum annuum

<400> SEQUENCE: 21

Met Lys Val Gly Asn Ser Lys Cys Asn Gly Val Asn Asn Asn Lys Asp
1               5                   10                  15

Val His Tyr Arg Gly Val Arg Lys Arg Pro Trp Gly Arg Tyr Ala Ala
            20                  25                  30

Glu Ile Arg Asp Pro Gly Lys Lys Ser Arg Val Trp Leu Gly Thr Phe
        35                  40                  45

Asp Thr Ala Glu Glu Ala Ala Lys Ala Tyr Asp Ala Ala Ala Arg Glu
    50                  55                  60
```

```
Phe Arg Gly Cys Lys Ala Lys Thr Asn Phe Pro Leu Pro Ser Glu Asn
 65                  70                  75                  80

Gln Asn Gly Ser Asp Ser Gly Ser Pro Asp Glu Ser Phe Ser Gly Glu
                 85                  90                  95

Asn Arg Ala His Ala Pro Ser Glu Phe Glu Leu Thr Arg Cys Leu Gly
                100                 105                 110

Ala Gly Gly Glu Gly Val Gly Asn Gly Gly Arg Leu Ala Glu Val Gly
            115                 120                 125

Leu Val Arg Asn Gly Asp Thr Ile Val His Ala Pro Thr Glu Leu Asp
130                 135                 140

Leu Thr Arg Leu Leu Gly Ala Gly Glu Gly Gly Asp Asn Ser Gly
145                 150                 155                 160

Tyr Ser Ala Glu Val Gly Leu Val Arg Asn Gly Phe Pro Ile Phe His
                165                 170                 175

His Gln Pro Pro Ile Glu Ala Pro Met Met Ser Asn Arg Ser Ser Pro
                180                 185                 190

Ala Glu Ser Tyr Ser Gly Glu Thr Ile Ile Asn Thr
            195                 200

<210> SEQ ID NO 22
<211> LENGTH: 176
<212> TYPE: PRT
<213> ORGANISM: Gossypium hirsutum

<400> SEQUENCE: 22

Met Ala Pro Arg Ser Lys Pro Ser Pro Ile Ser Pro Asn Pro Asp Pro
1               5                   10                  15

Asn Ser Lys Glu Ile Arg Tyr Arg Gly Val Arg Lys Arg Pro Trp Gly
                20                  25                  30

Arg Tyr Ala Ala Glu Ile Arg Asp Pro Arg Lys Lys Thr Arg Val Trp
            35                  40                  45

Leu Gly Thr Phe Asp Thr Ala Glu Glu Ala Ala Arg Ala Tyr Asp Ala
 50                  55                 60

Lys Ala Arg Glu Phe Arg Gly Ala Lys Ala Lys Thr Asn Phe Ala Asp
 65                  70                  75                  80

Asn Asn Ala Asn Asp Phe Thr Arg Ser Pro Ser Gln Ser Ser Thr Val
                 85                  90                 95

Glu Ser Ser Pro Pro Leu Asp Leu Thr Leu Ala Ser Pro Cys
                100                 105                 110

Ser Ser Leu Pro Val Thr Ala Gln Arg Pro Val Tyr Phe Asp Ala
            115                 120                 125

Phe Ala Thr Gly Gly Ser Gly Cys Pro Ala Ser Gly Phe Ala Gln Ser
130                 135                 140

Asp Ser Asp Ser Ser Ser Val Val Asp Phe Glu Gly Gly Val Arg
145                 150                 155                 160

Arg Arg Val Phe Asp Leu Asp Leu Asn Gln Leu Pro Ala Glu Met Asp
                165                 170                 175

<210> SEQ ID NO 23
<211> LENGTH: 345
<212> TYPE: PRT
<213> ORGANISM: Oryza sativa

<400> SEQUENCE: 23

Met Gln Ala Gln Gln Ala Met Asp Glu Pro Ala Asn Ala Gln Leu Tyr
1               5                   10                  15
```

```
Gly His Ala His Ala His Ser His His His Arg Ser Lys Arg Pro Ser
            20                  25                  30

Pro Gly Gly Gly Gly Gly Ala Ala Thr Leu Gly Ala Asp Gly Gly
        35                  40                  45

Gly Gly Gly Gly Ser Leu Ser Gly Thr Arg Tyr Arg Gly Val Arg Arg
    50                  55                  60

Arg Pro Trp Gly Arg Phe Ala Ala Glu Ile Arg Asp Pro Ala Ser Lys
65                  70                  75                  80

Glu Arg Arg Trp Leu Gly Thr Phe Asp Thr Ala Glu Gln Ala Ala Cys
                85                  90                  95

Ala Tyr Asp Val Ala Ala Arg Ala Met Arg Gly Thr Arg Ala Arg Thr
            100                 105                 110

Asn Phe Pro Val Pro Ala Ala Gly Phe Pro Gly Gly Gly Gly Gly
        115                 120                 125

Gly Cys Trp Pro Trp Val Asn Ile Pro Pro Gln Gly Ala Ala Ala Ala
    130                 135                 140

Ala Ser His Gln Gln Pro Leu Asn Thr Leu Leu Leu His Asn Leu Leu
145                 150                 155                 160

Met Ser Ser Ser Pro His Gly Cys Leu Leu Leu His His Ala Gly His
                165                 170                 175

Gly His Gly His Ala His Ser His Ser His Ser His Ser Arg Ala His
            180                 185                 190

Asn Pro Ser Thr Arg Pro Pro Thr Ser Ala Pro Pro Pro Pro Pro
        195                 200                 205

Ala Ala Ala Ser Ser Ala Thr Thr Ala Pro Ala Thr Thr Thr Gly Ala
    210                 215                 220

Ala Ala Thr Ser Ala Pro Gly Ala Asp Asp Asp Ala Trp Gly Phe Leu
225                 230                 235                 240

Leu Arg Arg Glu Pro Pro Glu Ala Gly Leu Leu Gln Asp Val Leu His
                245                 250                 255

Gly Phe Tyr Pro Thr Arg Arg Pro His Asp Asp Ala Gly Pro Ala Pro
            260                 265                 270

Lys Leu Glu Arg Pro Tyr Glu Ala Thr Ser Ser Tyr Arg Val Ser Ser
        275                 280                 285

Pro Trp Gly Ala Val Glu Asp Cys Asp Asp Gly Asp Gly Asp Gly Asp
    290                 295                 300

Asp Asp Tyr Arg Gly Phe Pro Met Met Pro Gln Gly Leu Leu Glu Asp
305                 310                 315                 320

Val Ile Gln Cys Pro Pro Tyr Met Glu Val Leu Ala Ala Pro Ser Ala
                325                 330                 335

Ala Val Gly Arg Val Ser Arg Arg Gly
            340                 345

<210> SEQ ID NO 24
<211> LENGTH: 189
<212> TYPE: PRT
<213> ORGANISM: Oryza sativa

<400> SEQUENCE: 24

Met Glu Leu Asp Met Gly Ala Gly Gly Gly Gly Val Gly Gly
1               5                   10                  15

Gly Arg Ala Glu Ala His Tyr Arg Gly Val Arg Lys Arg Pro Trp Gly
            20                  25                  30

Arg Tyr Ala Ala Glu Ile Arg Asp Pro Trp Lys Lys Thr Arg Val Trp
        35                  40                  45
```

```
Leu Gly Thr Tyr Asp Thr Pro Val Glu Ala Ala Leu Ala Tyr Asp Arg
     50                  55                  60

Ala Ala Val Ala Leu Arg Gly Val Lys Ala Arg Thr Asn Phe Gly Ser
 65                  70                  75                  80

Gly Ser Ser Gly Gly Gly Val Gly Gly His Gly His Gly His Ser
                 85                  90                  95

His Ala Gln Leu Pro Gln Leu His His Arg Met His Pro Arg Pro
                100                 105                 110

Pro Gln Gly Pro Gly His Phe Gly Gly Leu Asp Ile Ser His Pro Ser
                115                 120                 125

Pro Trp His Tyr Val Tyr Phe Pro Ala Arg Val Gln Ala Met Ala Pro
        130                 135                 140

Ala Ala Ala Gly His Val Ala Ala His Val Ala Ala Ser Leu Pro Ser
145                 150                 155                 160

Thr Thr Leu Glu Leu Arg Thr Gly Pro Ser Ala Gly Glu Leu Pro Phe
                165                 170                 175

Asp Leu Asn Glu Pro Pro Pro Ala Leu Leu Phe Gly Ser
                180                 185

<210> SEQ ID NO 25
<211> LENGTH: 225
<212> TYPE: PRT
<213> ORGANISM: Nicotiana tabacum

<400> SEQUENCE: 25

Met Arg Arg Gly Arg Ala Ala Ala Pro Ala Pro Val Thr Gly Glu
 1               5                  10                  15

Pro Asn Gly Ser Gly Gly Ser Lys Glu Ile Arg Phe Arg Gly Val Arg
                 20                  25                  30

Lys Arg Pro Trp Gly Arg Phe Ala Ala Glu Ile Arg Asp Pro Trp Lys
            35                  40                  45

Lys Thr Arg Val Trp Leu Gly Thr Phe Asp Ser Ala Glu Asp Ala Ala
 50                  55                  60

Arg Ala Tyr Asp Ala Ala Ala Arg Ala Leu Arg Gly Pro Lys Ala Lys
 65                  70                  75                  80

Thr Asn Phe Pro Leu Pro Tyr Ala His His His Gln Phe Asn Gln Gly
                 85                  90                  95

His Asn Pro Asn Asn Asp Pro Phe Val Asp Ser Arg Phe Tyr Pro Gln
                100                 105                 110

Asp Asn Pro Ile Ile Ser Gln Arg Pro Thr Ser Ser Ser Met Ser Ser
            115                 120                 125

Thr Val Glu Ser Phe Ser Gly Pro Arg Pro Pro Ala Pro Arg Gln
130                 135                 140

Gln Thr Thr Ala Ser Ser Arg Lys Tyr Thr Arg Ser Pro Pro Val Val
145                 150                 155                 160

Pro Asp Asp Cys His Ser Asp Cys Asp Ser Ser Ser Val Val Asp
                165                 170                 175

His Gly Asp Cys Glu Lys Glu Asn Asn Asp Asn Asp Asn Ile Ala
                180                 185                 190

Ser Ser Ser Phe Arg Lys Pro Leu Leu Phe Asp Leu Asn Leu Pro Pro
            195                 200                 205

Pro Met Asp Asp Ala Gly Ala Asp Asp Leu His Cys Thr Ala Leu Cys
210                 215                 220

Leu
```

225

<210> SEQ ID NO 26
<211> LENGTH: 188
<212> TYPE: PRT
<213> ORGANISM: Oryza sativa

<400> SEQUENCE: 26

Met Arg Lys Ser Lys Gln Pro Gln Pro Gln Pro Ser Pro Glu Ile Arg
1               5                   10                  15

Tyr Arg Gly Val Arg Lys Arg Pro Ser Gly Arg Tyr Ala Ala Glu Ile
            20                  25                  30

Arg Asp Pro Ala Lys Lys Thr Pro Ile Trp Leu Gly Thr Phe Asp Ser
        35                  40                  45

Ala Glu Val Ala Ala Arg Ala Tyr Asp Asp Ala Ala Arg Ser Leu Arg
    50                  55                  60

Gly Pro Thr Ala Arg Thr Asn Phe Pro Leu Ala Ala Pro Ser Ala Pro
65                  70                  75                  80

Pro Pro Arg Pro Pro Ala Ala Ala Ala Ala Thr Ser Ser His
                85                  90                  95

Ser Ser Thr Val Glu Ser Trp Ser Gly Gly Ala Pro Ala Ala Ala
            100                 105                 110

Ser Ala Leu Ala Arg Ser Ala Ala Pro Met Glu Ala Thr Gln Glu Glu
        115                 120                 125

Asp Cys His Ser Tyr Cys Gly Ser Ser Ser Val Leu Cys Glu Asp
    130                 135                 140

Gly Ser Asp Asp Ala Ala Ala Ser Arg Thr Pro Leu Pro Phe Asp Leu
145                 150                 155                 160

Asn Met Pro Pro Glu Glu Glu Leu Asp Met Ala Ala Val Ala Asp
                165                 170                 175

Gln Met Gly Ile Arg Tyr Asp Thr Leu Leu Arg Leu
            180                 185

<210> SEQ ID NO 27
<211> LENGTH: 225
<212> TYPE: PRT
<213> ORGANISM: Arabidopsis thaliana

<400> SEQUENCE: 27

Met Arg Arg Gly Arg Gly Ser Ser Ala Val Ala Gly Pro Thr Val Val
1               5                   10                  15

Ala Ala Ile Asn Gly Ser Val Lys Glu Ile Arg Phe Arg Gly Val Arg
            20                  25                  30

Lys Arg Pro Trp Gly Arg Phe Ala Ala Glu Ile Arg Asp Pro Trp Lys
        35                  40                  45

Lys Ala Arg Val Trp Leu Gly Thr Phe Asp Ser Ala Glu Glu Ala Ala
    50                  55                  60

Arg Ala Tyr Asp Ser Ala Ala Arg Asn Leu Arg Gly Pro Lys Ala Lys
65                  70                  75                  80

Thr Asn Phe Pro Ile Asp Ser Ser Pro Pro Pro Asn Leu Arg
                85                  90                  95

Phe Asn Gln Ile Arg Asn Gln Asn Gln Asn Val Asp Pro Phe Met
            100                 105                 110

Asp His Arg Leu Phe Thr Asp His Gln Gln Gln Phe Pro Ile Val Asn
        115                 120                 125

Arg Pro Thr Ser Ser Ser Met Ser Ser Thr Val Glu Ser Phe Ser Gly

```
                130                 135                 140
Pro Arg Pro Thr Thr Met Lys Pro Ala Thr Thr Lys Arg Tyr Pro Arg
145                 150                 155                 160

Thr Pro Pro Val Val Pro Glu Asp Cys His Ser Asp Cys Asp Ser Ser
                165                 170                 175

Ser Ser Val Ile Asp Asp Asp Asp Ile Ala Ser Ser Ser Arg Arg
            180                 185                 190

Arg Asn Pro Pro Phe Gln Phe Asp Leu Asn Phe Pro Pro Leu Asp Cys
            195                 200                 205

Val Asp Leu Phe Asn Gly Ala Asp Asp Leu His Cys Thr Asp Leu Arg
            210                 215                 220

Leu
225

<210> SEQ ID NO 28
<211> LENGTH: 58
<212> TYPE: PRT
<213> ORGANISM: Artificial Sequence
<220> FEATURE:
<223> OTHER INFORMATION: consensus
<220> FEATURE:
<221> NAME/KEY: MISC_FEATURE
<222> LOCATION: (1)..(1)
<223> OTHER INFORMATION: Xaa is His or Arg
<220> FEATURE:
<221> NAME/KEY: MISC_FEATURE
<222> LOCATION: (2)..(2)
<223> OTHER INFORMATION: Xaa is Phe or Tyr
<220> FEATURE:
<221> NAME/KEY: MISC_FEATURE
<222> LOCATION: (7)..(7)
<223> OTHER INFORMATION: Xaa is Lys or Arg
<220> FEATURE:
<221> NAME/KEY: MISC_FEATURE
<222> LOCATION: (10)..(10)
<223> OTHER INFORMATION: Xaa is Ser or Trp
<220> FEATURE:
<221> NAME/KEY: MISC_FEATURE
<222> LOCATION: (13)..(13)
<223> OTHER INFORMATION: Xaa is Phe or Tyr
<220> FEATURE:
<221> NAME/KEY: MISC_FEATURE
<222> LOCATION: (21)..(21)
<223> OTHER INFORMATION: Xaa is any amino acid
<220> FEATURE:
<221> NAME/KEY: MISC_FEATURE
<222> LOCATION: (22)..(22)
<223> OTHER INFORMATION: Xaa is Lys or Arg or Ser
<220> FEATURE:
<221> NAME/KEY: MISC_FEATURE
<222> LOCATION: (24)..(24)
<223> OTHER INFORMATION: Xaa is Ala or Glu or Ser or Thr
<220> FEATURE:
<221> NAME/KEY: MISC_FEATURE
<222> LOCATION: (25)..(25)
<223> OTHER INFORMATION: Xaa is Arg or Pro
<220> FEATURE:
<221> NAME/KEY: MISC_FEATURE
<222> LOCATION: (26)..(26)
<223> OTHER INFORMATION: Xaa is Ile or Arg or Val
<220> FEATURE:
<221> NAME/KEY: MISC_FEATURE
<222> LOCATION: (31)..(31)
<223> OTHER INFORMATION: Xaa is Phe or Tyr
<220> FEATURE:
<221> NAME/KEY: MISC_FEATURE
<222> LOCATION: (33)..(33)
<223> OTHER INFORMATION: Xaa is Ser or Thr
<220> FEATURE:
<221> NAME/KEY: MISC_FEATURE
<222> LOCATION: (34)..(34)
<223> OTHER INFORMATION: Xaa is Ala or Phe
```

```
<220> FEATURE:
<221> NAME/KEY: MISC_FEATURE
<222> LOCATION: (35)..(35)
<223> OTHER INFORMATION: Xaa is Glu or Gln or Val
<220> FEATURE:
<221> NAME/KEY: MISC_FEATURE
<222> LOCATION: (36)..(36)
<223> OTHER INFORMATION: Xaa is Asp or Glu or Gln or Val
<220> FEATURE:
<221> NAME/KEY: MISC_FEATURE
<222> LOCATION: (39)..(39)
<223> OTHER INFORMATION: Xaa is Cys or Leu or Lys or Arg
<220> FEATURE:
<221> NAME/KEY: MISC_FEATURE
<222> LOCATION: (43)..(43)
<223> OTHER INFORMATION: Xaa is any amino acid
<220> FEATURE:
<221> NAME/KEY: MISC_FEATURE
<222> LOCATION: (44)..(44)
<223> OTHER INFORMATION: Xaa is Ala or Lys
<220> FEATURE:
<221> NAME/KEY: MISC_FEATURE
<222> LOCATION: (46)..(46)
<223> OTHER INFORMATION: Xaa is Arg or Val
<220> FEATURE:
<221> NAME/KEY: MISC_FEATURE
<222> LOCATION: (47)..(47)
<223> OTHER INFORMATION: Xaa is Ala or Asp or Glu or His or Asn or Ser
<220> FEATURE:
<221> NAME/KEY: MISC_FEATURE
<222> LOCATION: (48)..(48)
<223> OTHER INFORMATION: Xaa is Phe or Leu or Met or Tyr
<220> FEATURE:
<221> NAME/KEY: MISC_FEATURE
<222> LOCATION: (51)..(51)
<223> OTHER INFORMATION: Xaa is any amino acid
<220> FEATURE:
<221> NAME/KEY: MISC_FEATURE
<222> LOCATION: (52)..(52)
<223> OTHER INFORMATION: Xaa is Lys or Arg or Thr
<220> FEATURE:
<221> NAME/KEY: MISC_FEATURE
<222> LOCATION: (54)..(54)
<223> OTHER INFORMATION: Xaa is Lys or Arg
<220> FEATURE:
<221> NAME/KEY: MISC_FEATURE
<222> LOCATION: (58)..(58)
<223> OTHER INFORMATION: Xaa is Ala or Gly or Pro

<400> SEQUENCE: 28

Xaa Xaa Arg Gly Val Arg Xaa Arg Pro Xaa Gly Arg Xaa Ala Ala Glu
 1               5                  10                  15

Ile Arg Asp Pro Xaa Xaa Lys Xaa Xaa Xaa Trp Leu Gly Thr Xaa Asp
             20                  25                  30

Xaa Xaa Xaa Xaa Ala Ala Xaa Ala Tyr Asp Xaa Xaa Ala Xaa Xaa Xaa
         35                  40                  45

Arg Gly Xaa Xaa Ala Xaa Thr Asn Phe Xaa
     50                  55

<210> SEQ ID NO 29
<211> LENGTH: 1765
<212> TYPE: DNA
<213> ORGANISM: Lolium perenne

<400> SEQUENCE: 29
tcggttggga tggaaaagcg agcagctaat ttctaaggag tttctaatgc cgccacgcaa      60
aagacgagga gagggcggc ggcgcgcgga cagtcaaagc gactgcgccg agttttattc     120
cttgttgccg ctccaccact cgctgccat ttgctttgct gctcctccty ccttttaac     180 cagccgcttc cccctataa taagtccccc tcctccccac ccgatcctac acgcatccat     240
```

```
acgcgctgcg cacaccatcc aacaagagac gaaaagaagg aaaggaaacc atggcgccga        300
ggacgtcgga gaaggcggcg gcggcagcgg caccgtctgc cgctgcggcg accgggcttg        360
cgctcggcgt gggcggtgga ggtggaggtg gtggtgtggg gacgcacttc aggggcgtga        420
ggaagcgtcc gtggggccgg tacgcggcgg agatccgcga cccggcgaaa agagccgcg         480 tgtggctggg cacgtacgac acggccgagg aggcggcccg cgcctacgac gccgccgcgc        540
gcgagtaccg cggctccaag gccaagacca acttcccgct gttcccgtcc cgctggcca         600 cggccgtgcc cgtcggcgcc ggcggagacg gcagccggag cagcaacagc agcaccgtgg        660
agtcgttcgg cggcgacgtg caggcgccca tgcaggccat gccgctccct cccgcgtcgc        720
tggagctcga cctcttccac cgcgccgcca acgccgcggg cggtgcaggc gccggcgtga        780
ggttcccgtt cagcggctac cccgtgtccc acccgttcta cttcttcggc caggccgcgg        840
cggccgccgc cgctgggtgc cacatgtacg gcagcagcat gcctccgcag gtgaccgccg        900
ccccccgccg ccgcgtcggc gcagagggcg cccgtcgatt ttgacctgga cctgactgcc        960
cgccgccggc ggagctcctc tgatcgtttg gcgccggag ttttttagct gatatgatca       1020
tgactcgcta gtagtttcgt tcgtcggttt ttttttttctc tcttgtatgt ttaggcgtcc      1080
ggccctctcg cgtaacggag gagagggta gatctgtaaa tacggtttcc ttttttttcgc      1140 cggaggggag tacagtggtt agcttgagat ggaagaagac ccgagatgta ctgccgccca      1200
aggcaaggca agtcctgccg cgttgttat ggaccgaatt atattgagtt attactactt        1260
ggacagcctg gagaaaagac tcgtactgta tttattggt aataatatac ttattgaatg        1320
ttttcttatt tttgcatcta ctacctccat ctgatctgag atgtcttgtg ctgttgaaat        1380
ggaaacggaa acggaagtga gtgcgttttg ggtggcgttt gcacatccgt cgcctcagct      1440
gggatcttga ttccgaccca tgcaacatga tcataattgg gcggttgaag aagaagaaat       1500
gaaggtcgag tcgtcctgca tggattctct acgtgtcgaa tttactgcga ctgtcagtga        1560
cggtattgcg ctcccgatca atcgccatta acgacgagat gccgttcctc cggggggga      1620 aattgtcgct gtcccccacc tttggagctg ttggcggcac aagtgggcag catatattgc      1680
tgtcgaaaga aaacacacgc gtaacaagat aaatcgctct ctagctagct aggctgccgt      1740
cctctgtgtg ccgacggacg gtatc                                            1765
```

<210> SEQ ID NO 30
<211> LENGTH: 711
<212> TYPE: DNA
<213> ORGANISM: Oryza sativa

<400> SEQUENCE: 30

```
atggcgccga gaacgtcgga caagactatg tcaccggcgg ccgcggccac cggactcgcg         60
cttggcgtgg gcggtgtcgc cggagccgcc gccgtgggca ccgccagca cttccgtggc         120 gtgaggaagc ggccgtgggg ccgttacgcg gcggagatcc gcgacccggc caagaagagc        180
cgcgtgtggc tcggcacgtt cgacacggcc gaggaggccg cgcgcgccta cgacgccgcg        240
gcgcgcgagt accgcggtgc caaggccaag accaacttcc cctaccctaa cggcgcgccc        300
gccgccggtg tgaacagcgg cagcagcaac agcagcaccg tcgagtcgtt cggcagcgac        360
gtgcaggcgc ccatgaaggc catgccgatc ccgccgtcgc tcgagctcga cctgttccac        420
cgcgccgcag cggccgcggc ccgcggcgca ggcggcatgc gtttcccttt cgagggctac        480
cccgtatcgc acccttacta cttctttgga caagcgccg ccgccgccgc cgcctctggt         540
tgccgcatgc tcaagattgc gccggcgccg gtcaccgtgg ccgccttggc acagagcgac        600
```

```
tccgactcct cgtcgatcgt ggatctggca ccatcaccgc cgccgcgtt ggcgaagaaa    660 gccatcgctt ttgatcttga tctgaactgt ccgccgccga tggaggtcta g           711

<210> SEQ ID NO 31
<211> LENGTH: 708
<212> TYPE: DNA
<213> ORGANISM: Oryza sativa

<400> SEQUENCE: 31
atggcgccca gagcagctac ggtggagaag gttgctgtgg cgccacccac cgggcttggt    60
cttggcgtcg gcgaggtgt cggagccggg ggtcctcact acaggggcgt ccgcaagcgc   120
ccgtgggggc gttacgcagc ggagatccgt gaccctgcca agaagagccg ggtgtggctc   180
ggtacctacg acacggcaga ggaggccgcc cgcgcctacg acgccgccgc tcgagagttc   240
cggggtgcca aggcaaaaac aaactttccg tttgcatcac agtcgatggt cggctgtggc   300
ggcagcccca gcagcaatag cacggtagac accggtggcg gcggggttca gacgcctatg   360
cgggccatgc tcctgccgcc gactctggac ttggatttgt tccaccgcgc ggctgctgtg   420
actgcagtcg ccggcaccgg cgttcgcttt cctttcagag gatatcccgt tgcacgtcca   480
gcaacgcatc cttactttt ctatgagcag gctgcagcgg ctgccgcagc tgaggctgga   540
taccgtatga tgaagcttgc accgccggtc accgtggcgg cggttgcaca agtgactcc    600 gactcctcgt cggtggttga tctcgcgccg tcacctccag cggttacggc gaacaaggcg   660
gcagctttcg atctggatct gaaccggccg ccgccggtag agaactag               708

<210> SEQ ID NO 32
<211> LENGTH: 1003
<212> TYPE: DNA
<213> ORGANISM: Stylosanthes hamata

<400> SEQUENCE: 32
ccacactctt cccaaccaaa acaaaaaaca attcagctaa attatttatt attatggctc    60
ccagggagaa gacgcctgcc gttaaagtta acgctggcgt taaagaggtg cattttaggg   120
gtgtaaggaa gaggccatgg ggaaggtacg cagctgaaat cagagatccc ggcaagaaga   180
gccgcgtctg gctcggaacc ttcgacaccg ccgaggatgc agcgcgtgca tacgacgccg   240
ccgcccgaga gttccgcggc cccaaggcta agaccaactt ccccttccct gattccgacg   300
acatcaacag taacaataac aacatcgtcg tcgtaaagaa caataaccgc agccctagcc   360
agagcagcac cgtcgagtct tccagccgtg accgcgactc ctactccgcc gctgccgctg   420
ccaccgccgt cgccgattcc tctccgttag accttaactt ggcccccgca ggagctggat   480
tcgccggatc cattcggttc ccattccaac agccgttcgc cgtgtttccc ggcgggatgc   540
cggcggcgaa gcaagcactg tacctagacg cggtgcttcg cgccagcatg gctagtcacg   600
gccagttcgg tttcggttat aaccgtcccg cggcggcggc ggctgagcg cagagtgact    660 cagactcatc gtcggtgatc gatctgaacc agaacgaagg cgatgttgct aagaataacg   720
gaagagggtt ggttcttgac ctgaacgaac ctcctcctca agagatggct tgaaccttag   780
ggttccgtaa ttttttttaa tgttcccgga ttataagtc ctctatcctt tttttgttta    840
agaaaatcta attaagagga ggaaatagga ggatgaagaa gcagtagttt tgtgaataga   900
atagaatttt tttgcgacgg ggaaactaaa cgatcccgtt tggatctctg ttgttccgaa   960
aattaaagcc caatgttaat taattacgaa actttaatta cta                  1003
```

<210> SEQ ID NO 33
<211> LENGTH: 663
<212> TYPE: DNA
<213> ORGANISM: Vitis aestivalis

<400> SEQUENCE: 33

```
atggcgccga gagacaaacc taccggcgta accgccggcg ctaccggaaa caaggagatc      60
cgctacagag gcgtgcgcaa gaggccgtgg ggcaggtacg ccgctgaaat acgcgatccc     120
ggcaagaaga gccgcgtctg gctaggcacc tttgatacgg ccgaggaggc cgcgcgtgcc     180
tacgatgcag cggctaggga gtttcgtgga gccaaggcaa agactaactt cccttcgcct     240
accgaccttg cggcagctgc cgcgactact gctaaccgga gccctagcca gagcagcacc     300
gtggagtcct ccagccgcga ggcgctgtct ccgggtgcga tcgctggtcc tccggctcta     360
gatctcaatc tgtctcaccc cgccgccgcc ggccaatttt ccgcagttcg ttaccctgcg     420
gttggtgttt ttcctattgc gcagccgttg ttcttcttcg agccatttttc ccgtccagag     480
aagccgaaga cccaccgcga tatgttcgat ttagatcgag cggttgccga ttttcacccct    540
gcgattgccg gtagcgttca cagcgactcc gactcatcct ccgtggttga tttcaattac     600
catgaccgca gtaccaggct gctcaatctc gatctcaacc atcctccagc ggaagtcgct     660
tga                                                                    663
```

<210> SEQ ID NO 34
<211> LENGTH: 1018
<212> TYPE: DNA
<213> ORGANISM: Stylosanthes hamata

<400> SEQUENCE: 34

```
ccacactctt cccaaccaaa acaaaaaaca attcagctag attagtatta ctattaagtt      60
aattatttat tatggctcca agggagaaga cgcctgccgt taaggttaac ggcaaaagta     120
acgccggcgt taaagaggtg cattttaggg gtgtaaggaa gaggccatgg ggaaggtacg     180
cagctgaaat cagagatccc ggcaagaaga gccgcgtctg gctcggcacc ttcgacaccg     240
ccgaggacgc agcgcgtgca tacgacgccg ccgcccgaga gttccgtggc cctaaggcta     300
agaccaactt cccctttcct gattccgacg acatcaacaa taacaacatc gtcgtcgtta     360
agaacaataa ccgcagcccc agccagagca gcaccgtcga gtcttccagc cgagaccgcg     420
actcctactc cgccgccgct gccaccgccg tcgctgattc gtctccgttg gaccttaact     480
tagccccgca ggagctggat tcgccggatc cattcggttc ccattccacg cagccgttcg     540
ccgtgtttcc cggcgggatg ccggcggcga agcaggctct gtacctagac gcggtgctgc     600
gcgccagcat ggctagtcac ggccagttcg gtttcggtta taaccgtcca gcggcggcgg     660
gagcgcagag tgactcggac tcgtcgtcgg tgatcgatct gaaccagaac gagggcgatg     720
ttgctaagaa taacggaaga gggttagttc tagacctgaa cgaacctcct ccacaagaga     780
tggcttgaac cttagggttc cgtaactttt aatgttcccg gattatgagt ctctctatct     840
tttttttttt tttttttgttt ttaagaaaaa aaatctaatt aagaagagga aatagggaag    900
aagaagaagt agtttttgtga atagaataga attttttgcg acgggcgatc ccgtttggat    960
ctctgttgtt ccgaaaattt aaaccccaat gttaattaat tacgaaactt tcactact    1018
```

<210> SEQ ID NO 35
<211> LENGTH: 771
<212> TYPE: DNA
<213> ORGANISM: Thellungiella halophila

<400> SEQUENCE: 35

```
cctcgtgccg aattcggcac gaggatcttc tcgtttcttt cacaattatt agtttttgat      60
catcctcatg acgaaaatgg gtttcaaacc cgactccaac ccgagcccga acccgaacga     120
gagtaatgcc aaagagattc gttacagagg cgtgaggaaa cgtccatggg gaagatacgc     180
ggcggagatc cgagatccgg gtaagaaaac tcgggtctgg ctcggaacgt tcgacacggc     240
tcagcaagcg gcgcgtgctt acgacgctgc agcgcgtgag tttcgcggcg ctaaggctaa     300
gacgaatttc ccgacgtttc tcgagcttaa cgcggctaaa gacggtggtt tcgctcgcag     360
tcctagtcag agcagcaccg tcgactctgt ctctccgacg tcggcgcgat ggtgacacc      420
tccgcagctc gagctcagtt taggcggcgg tggtggcggc gcgtgttacc agattccggt     480
tgcacgtcgt cctgtttact tctataacat gacgacgttt ccggcggcgg cggcggcaac     540
gtgtggggtc cagagcgagt cagattcgtc gtccgtcgtt gatttcgagt gtggagccga     600
gaagaaatat cgtccgttag atctggatct taatttggct cctcctgcgg aataggccgt     660
caggttcttt tcatttgtcc gaacgttgtt tagtctgtga cgcgtcgcgt tttcttatga     720
agagaaaatc gcgttctcct cttagttttt ttttttctta tctaaaaaaa a              771
```

<210> SEQ ID NO 36
<211> LENGTH: 750
<212> TYPE: DNA
<213> ORGANISM: Vitis aestivalis

<400> SEQUENCE: 36

```
atggcgccca aggagaaagt tgccggcgtt aagcctagcg ccaacgccaa ggaggtgcat      60
ttcaggggcg ttaggaagag accgtggggg agatacgccg ccgagatcag ggatccaggg     120
aagaagagcc gtgtatggct tggaactttt gatacggcgg aggaagccgc caaggcgtac     180
gactccgccg cccggggagtt tcgcggcgcc aaggcgaaga ccaactttcc tttggtttct     240
gagaatctga acaacaataa tcagagtccg agccagagca gcaccgtgga gtcttccagc     300
cgggagggat tttcgccggc tctaatggtt gattcctctc cattggatct taatctgctg     360
cacggaggtg gcgtcggcgt tggcgttggc gtcggcgttg gtgctgctgc tggatatgcc     420
accgccatga gatttccgtt tcagcatcat cagtttcaag tttcctcccc ttcgccggct     480
gccggaattg ttccgaccgg aggcttgcct gcggcgaatc accttttcta ctttgacgcg     540
atgttacgga ctgggagagt taatcaagat tttcagagac tgaggttcga ccgtgcggcg     600
tctgatttcc gcgccgcgct taccggtggg gtccagagcg attccgactc atcatctgtg     660
gttgatttga accacaacga tctcaagcct cgcgcacgcg ttctcatcga tctcgatctg     720
aaccgccctc ccccgcctga aatcgcctga                                     750
```

<210> SEQ ID NO 37
<211> LENGTH: 669
<212> TYPE: DNA
<213> ORGANISM: Arabidopsis thaliana

<400> SEQUENCE: 37

```
atggccaaga tgggcttgaa acccgacccg gctactacta accagaccca caataatgcc      60
aaggagattc gttacagagg cgttaggaag cgtccttggg gccgttatgc cgccgagatc     120
cgagatccgg gcaagaaaac ccgcgtctgg cttggcactt tcgatacggc tgaagaggcg     180
gcgcgtgctt acgatacggc ggcgcgtgat tttcgtggtg ctaaggctaa gaccaatttc     240
```

```
ccaactttc tcgagctgag tgaccagaag gtccctaccg gtttcgcgcg tagccctagc    300
cagagcagca cgctcgactg tgcttctcct ccgacgttag ttgtgccttc agcgacggct    360
gggaatgttc ccccgcagct cgagcttagt ctcggcggag gaggcggcgg ctcgtgttat    420
cagatcccga tgtcgcgtcc tgtctacttt ttggacctga tggggatcgg taacgtaggt    480
cgtggtcagc ctcctcctgt gacatcggcg tttagatcgc cggtggtgca tgttgcgacg    540
aagatggctt gtggtgccca aagcgactct gattcgtcat cggtcgttga tttcgaaggt    600
gggatggaga agagatctca gctgttagat ctagatctta atttgcctcc tccatcggaa    660
caggcctga                                                            669

<210> SEQ ID NO 38
<211> LENGTH: 741
<212> TYPE: DNA
<213> ORGANISM: Cucumis sativus

<400> SEQUENCE: 38
atggctccga gggagaaggc agttgccgtc aagcctagcg tcggtaacgt gaaggaagtg     60
cattttagag gagtgaggaa gcggccatgg gggagatatg ccgctgagat cagagatccc    120
agtaagaaaa gccgggtttg gcttggaacc tttgataccg cggaggaggc ggctcgagcc    180
tacgacagcg ccgctagaga tttccgcggc gttaaggcca agaccaattt cccctttgccc   240 tccgatgatc agcttcttaa ccttaacaat aagattaaca acatcaacaa taatcagagc    300
ccgagtcaga gtagcacggt tgagtcctct agccgggagc aagctctgat ggttgattcc    360 tccccttga atctcaatct aggtcacggt attggcggac tcacgaacgc tggacccatc    420
agtttcccat ttcagcgtta ccaaattccc atgatcggag aagtttttac ccgcggcata    480
ccgccttcga atcacgttct ctatttcgat gcggctctac gtgctggaat gatcaacagt    540
catccgaacc aacggctaca cttcgaccgt attcgcgaag cggtgagtga tttccgacgc    600
gagttcgccg gcagcggtgt tcagagcgac tccgattcct cctccgttgt ggacatgaac    660
ggtcaagacc tcaagccccg aggaggaagt ggcggccgcc ttgatttgga tctcaacttt    720 ccccccaccag aatccgcctg a                                             741

<210> SEQ ID NO 39
<211> LENGTH: 669
<212> TYPE: DNA
<213> ORGANISM: Oryza sativa

<400> SEQUENCE: 39
atggctccca ggaacgccgc cgaggccgtc gccgtcgccg tggcggaggg cggaggagcc     60
ggcatggagc ccaggttccg cggcgtgagg aagcgcccgt ggggcaggta cgcggcggag    120
atccgcgacc cggccaggaa ggcgcgggtg tggctcggca ccttcgacac cgccgaggcc    180
gcggcgcgcg cctacgacag cgccgcgctc cacttccgcg ggcccaaggc caagaccaac    240
ttccccgtcg cctcgcgcac cgcccaccac cacgccccgc cgccgccgct gcccaaggcg    300
gcggcgctgg ccgtcgtcag cccgaccagc agcacggtcg agtcgtcctc ccgggacacg    360
cccgccgccg ccccggtggc ggccgcggcc aaggcccagg tgcccgcctc gccttcgctc    420
gatctgagcc tcgggatgtc ggccatggtg gccgccagcc cgttcctgtt cctcgacccc    480
agggtcgcgg tgaccgtggc cgtgcgcggca ccggtgcctc gccggccggc cgtcgtcagc    540
gtcaagaagg aggtagctcg cctggacgag cagagcgaca ccggctcgtc gtcatccgtg    600
gtggacgcct cgccggccgt cggcgtgggg ctcgacctga acctgccgcc gccgatcgag    660
```

```
gaggcgtag                                                              669

<210> SEQ ID NO 40
<211> LENGTH: 3818
<212> TYPE: DNA
<213> ORGANISM: Nicotiana sylvestris

<400> SEQUENCE: 40
agatcttttc ttcttaggta gaggtagaaa atgtctagtg aagtgcaagc ataataacac      60
tcggtcacaa tggcaggcga aaatactaaa atgcatatgc aatagctgtt aaatgaaaaa     120
acatgagttt acttggtcaa gcgcttcaca ggaacaaaat gaaagcacgg ccaaggtggg     180
ccttgatttg ataaaataga cgcgtagagc gcggaaaatg gacgcgtgtc tgctgaagat     240
agtggggttt gcggtgatct gtcggtatta aatctgatgg tataagcga atagatagac      300
tcgtttccga gccaaagacg gctaattttc attaatatag gaaacaataa taaactatta     360
ctactactaa tataatactt tgaaatacaa caagtgtgca gtactctacg gatctcaata     420
tgggtcactc tatcaggaca acaacatagt cggcggctat tggtaagtga aatgtgccgt     480
agccgtattt gttttctact attagacgct ttcttttttga attggtcatc atctattccc     540
aattagaaat ccctttaact cattgctctt tggcgtttgc cacccacgct ccataattc      600
tcccctgatt cattatctga agttcccccc cccaccccccc cttttatgag aaacatatt     660
aaatctcaaa tatagtttag tttatttatt aaaaaaataa gagaagcttc ttgaaaataa     720
gagattacca caagtgtgat tggttactga aatggataaa aagcatgaaa gattagactc     780
taaattttag taattaaaaa ataaaaatat taagttatat tttttatcta cttaagattt     840
catttataaa gctatttaaa atatatattg gtgaaaagta ataagtataa aagaaatata     900
ctcaatatat tcctataggt gggatacgtg aaaaataata agtaatcaaa atattaattg     960
atttgagtat taaacaataa agggcaacac aaattaatca ctccagaaat ataaagattt    1020
gatggacaaa tacactttgt ttaactttga tttgcttatt atctgtaaaa taaaatctaa    1080
aactaacgaa atttagtagt acaaaattgg ttacgtgtcc atgacaagaa taaacaagta    1140
gaagaaacct cattcctaaa caaaacacgg ccgtctaata tcaaaaatcc aaagccaatc    1200
aacatctcta aaccgctttt gtctacgtaa acgcccgcgt gccacgtaac tccctacaca    1260
tttctcaatt attactctct ccacacacct ctcttcttat attgcttggg cggcgctttc    1320
tcacctccag tcaaacccct cgttgaccac gctcccccta ccccacctct ccttttaatc    1380
tctcttcctt cctctattat ataactaact cttacctatc ctttgttcct cactctgttt    1440
ttcacataga atattaagca gtgttgtgta ttttcttttg acaaaatggc tgtcaaaaat    1500
aaggttagta atggtgatct gaaaggagga aatgtgaaaa caaatggagt taaggaggtt    1560
cactacagag gtgtaaggaa gaggccatgg ggtcggtatg cagctgaaat ccgtgacccg    1620
ggtaagaaga gtcgggtctg gttgggtact tttgacacgg cggaagaggc ggctaaggcg    1680
tacgacactg ccgctcgaga gtttcgtgga cccaaagcta aaactaactt ccctttaccg    1740
tcggagaatc agagtaccag tcacagcagc accatggagt cctctagcgg agagactggc    1800
attcacgcgc cgcctcatgc gccgctcgag ctggatctca cgcgccgact ggctccgta     1860
gctgctgatg gcggtgacaa ctgtcgtcgt tctggtgaag ttgggtaccc gattttccac    1920
caacagccga cggtggcggt tctccctaac ggccagccgg ttttgctctt tgattctttg    1980
tggcggccgg gagttgttaa caggcctcag ccttaccatg taatgccgat ggcgatgggg    2040
```

```
tttaacggcg ttaacgccgg agtggatcct actgtgtcag actcgtcctc tgtagtggaa    2100
gagaaccaat atgatgggaa aagaggaatt gatcttgatc ttaaccttgc tccacctacg    2160
gaattttgat gatgacgata ataaatttgg tagagagaag agtgagacag agactaatgg    2220
ttgaattttg tgtatacgtt aaaagaactg ttcgttttt  gcagctgagg ggtttgttat    2280
gatgttctct tgctgtttct actatttgtt aactctaatc cttgtttagg cattctgatt    2340
taatgagaaa attagtgttt ctccttgga  ttgtctaatt ttcagctaat ctaatgttag    2400
tagcatattt tccctatta  tttgggagtt gagtatatta tattgcatta tctatcccag    2460
tactttagat cttgttttaa ttattattaa agaaagggaa acaatgatgg ataatgttcg    2520
actatactgc agttttttca actctccagg cttttcaatg tatatttggg cgaacttcta    2580
gtggtctaac aaaccttaaa tcgtacaagt actcgggcta ttttcctaat ggttttattt    2640
tgtactactt aattattgag agaaatatca taatagttgt cggccaaatc gatcccaaat    2700
ttagaaagca ttaacaatcc tagtctaact ggaaaaaatc atttcaactt cgtaccagat    2760 tcattttcg  gttgcaatgc caaagtagat agtagttatt attatctttt ttttcagtca    2820
aagatactac tgtttaacca aaaatctgaa tcctaaaaga aaaattcggg ttactgataa    2880
tcaggagaca aaaaataaaa tacttttgag aacaatggta gaggataaat agataagtat    2940
ttcagtgtat tctcaatagt atctcgtgtc cttacaaatg atgatacttc tttcttttat    3000
agatcattct aggtaaagga ataaagcatc agttttaatg acataatcat gagcaataaa    3060
tgacattaaa taagtcgtta tacaatcatt cctattaaat accaacttta taacgtatca    3120
gacatttaat aatgaatttg gactcctttc tgtcatctga tccttgcttt caatgccttc    3180
taatccgttg gctgcaaata atttaaattg gtacgagact cgtatctata cgtcgtctcg    3240
tgcttattta aattcttctt cccgtggttg ttttcaccgt gcctcttagt caattgctgt    3300
tctttgacca ttcaactaat ccacgtgtca tgccacatca tttttaatat aaattcagtt    3360
tttttcccaa tacagatagt ccccccactt tccatttttt tatcaattaa ataattggga    3420
agtggatctt catgtaaaaa gaacttttgc cacaattaat gctcatgaca gtactaacgt    3480
ctcagcagtc ttttccattt aatgctctgt ccatgtgtca ttttataatt gattccgcta    3540
ttcattcatt tcttcgagac ttcttcattc tcactgttta cgaagtgata gctgccttta    3600
ttatagactt tcatcatta  tacttaaaaa gttgacggtt cccatttttac acataacttt    3660 gtcttccttt gtcttcttca ctaatcttcg acacatacct tcttcttgac aatgtcttct    3720
tcaaacccta accgtaaaaa agttccaatt ctagatcagt tccccaacgc ccctattaga    3780
cacagaagag gcggaggaag taggcctcga acagggtt                            3818
```

<210> SEQ ID NO 41
<211> LENGTH: 911
<212> TYPE: DNA
<213> ORGANISM: Nicotiana tabacum

<400> SEQUENCE: 41

```
caacatggct gtcaaaaata aggttagtaa tggcaatctg aaaggaggaa atgtgaaaac     60
agatggagtt aaggaggttc actacagagg tgtaaggaag aggccatggg gtcggtatgc    120
agctgaaatc cgtgacccgg gtaagaagag tcgggtctgg ttaggtactt tcgacacggc    180
ggaagaggcg gctaaggcgt acgacaccgc cgctcgagag tttcgtggac ccaaagcaaa    240
aactaacttc ccttcaccga cggagaatca gagcccaagt cacagcagca ccgtggagtc    300
ctctagtgga gagaatggtg ttcacgcgcc gcctcatgcg ccgctcgagc tggatctcac    360
```

```
gcgccgtctt ggctccgttg ctgcagatgg cggtgacaac tgtcgccgtt ctggggaagt      420
tgggtacccg attttccacc agcagccgac tgtggcggtt ctgccaaatg ccagccggt       480 tctgctcttt gattctttgt ggcgggcggg agttgttaac aggcctcagc cttaccatgt      540
aacgccgatg gggtttaacg gcgttaacgc cggagtgggg cctactgtgt cggactcgtc     600
ctctgcagtg gaagagaacc aatatgatgg gaaagagga attgatcttg atcttaacct      660
tgctccacct atggaatttt gatgatgacg ataatgttat ttggcagaga gaagagagag    720
agagagacta atggttgaat tttgtatata cgtaaaagaa actgttcgtt ttttcgcag     780 ctgagggggt tgtaatgttc tcttgctgct tctactattt gttaactcta atccttgttt    840
aggcattctg attaatgaga aaattagtgt tttctccttc caaatatcta tctagcgttc    900
tccttcagca g                                                          911

<210> SEQ ID NO 42
<211> LENGTH: 937
<212> TYPE: DNA
<213> ORGANISM: Arabidopsis thaliana

<400> SEQUENCE: 42
gtcgacccac gcgtccgact ctctctctaa tctatctatc cgagaatggc caagatgggc      60
ttgaaacccg acccggctac tactaaccag acccacaata atgccaagga gattcgttac    120
agaggcgtta ggaagcgtcc ttggggccgt tatgccgccg agatccgaga tccgggcaag    180
aaaacccgcg tctggcttgg cactttcgat acggctgaag aggcggcgcg tgcttacgat    240
acggcggcgc gtgattttcg tggtgctaag gctaagacca atttcccaac ttttctcgag    300
ctgagtgacc agaaggtccc taccggtttc gcgcgtagcc ctagccagag cagcacgctc    360
gactgtgctt ctcctccgac gttagttgtg ccttcagcga cggctgggaa tgttcccccg    420
cagctcgagc ttagtctcgg cggaggaggc ggcggctcgt gttatcagat cccgatgtcg    480
cgtcctgtct acttttggga cctgatgggg atcggtaacg taggtcgtgg tcagcctcct    540
cctgtgacat cggcgtttag atcgccggtg gtgcatgttg cgacgaagat ggcttgtggt    600
gcccaaagcg actctgattc gtcatcggtc gttgatttcg aaggtgggat ggagaagaga    660
tctcagactg ttagatctag atcttaattt gcctcctcca tcggaacagg cctgagcttt     720
taacggtgtc gtttcaattc gaagcgcatg cgtttcttct tcttttgag ctgtgaaaat     780 tcgttttctc atagttttc ctctctctct ctctcagtct aaatttatta ccagttttta    840
gaaagaaaaa acagattaaa tctgagagag aaaaatataa ttttagctga catggatcgt    900
tatgtacata ttattacata accggagatc tgaactg                               937

<210> SEQ ID NO 43
<211> LENGTH: 878
<212> TYPE: DNA
<213> ORGANISM: Arabidopsis thaliana

<400> SEQUENCE: 43
catcgctgtc tggaacagca aaaaccatct ctcaaaatgg ctttgactgt tcacaagaaa      60
gctccccaaa aggagcgttg ctttactctc ctataaaaag aagctcttct acttcttctc    120
gttaccacaa aactcttca ccgatcttct cgttccattc ttcttcctaa ttacaccatg     180
cccaacatca ccatgggttt gaaacccgac ccggttgctc caacgaaccc gactcatcat    240
gagagtaatg ctgccaaaga gattcgttac agaggcgtta ggaaacgtcc atggggaaga    300
```

```
tacgccgctg agatccgaga tccggttaag aaaactcgag tctggctcgg tacgttcgac    360
accgctcagc aggcggcgcg tgcttacgac gcagccgcgc gtgactttcg tggtgttaag    420
gctaagacca atttcggtgt tatcgttggt agtagtccta ctcagagtag caccgtcgtc    480
gactctccca cggcggcacg gtttataaca cctccgcacc tcgagctcag cttaggcggc    540
ggcggcgcgt gtcgtcgtaa gatcccgctt gtgcatccgg tttactacta taacatggcg    600
acgtatccaa agatgacgac gtgtggtgtc cagagcgagt ctgaaacgtc gtcggtcgtt    660
gatttcgaag gtggagctgg gaagatatct ccgccgttag atctggatct taacttagct    720
cctccggcgg aataggccgt gagttttttt tttcttatgt cgtttcttta gacaaaaaaa    780
aaataacgtt tccttttttt ttctgcctaa gaaaaaaata ttatccgttt tttagaagaa    840
agtgtagaaa agctccaata taattttag ctgccgag                             878
```

<210> SEQ ID NO 44
<211> LENGTH: 2898
<212> TYPE: DNA
<213> ORGANISM: Lycopersicon esculentum

<400> SEQUENCE: 44

```
gcggccgcta gcgccgcgca attcgcggcc gctggcgcct aaggaaaaaa ttggtgcagt     60
tacagctatg gcaatggtga atttaaatgg aatttcgaaa gaggtgcatt atagaggtgt    120
aaggaagagg ccatggggga gatacgcggc ggagattaga gatcctggga aaaaagtag    180 ggtttggtta ggtactttcg atactgcgga ggaggcggct agagcttatg ataacgctgc    240
tagagaattt cgtggagcga aagcgaaaac taattttccg aaattagaaa tggaaaaga    300 ggaagatctg aaattcgctg tgaaaaatga atcaatcgg agtccgagtc agactagtac    360 tgtgagtca tcgagtccgg ttatggttga ttcatcatcg ccgttagatc taagtctctg    420
tggatcaatc ggcgggttta atcatcatac ggttaagttc ccgagctccg gtggaggttt    480
taccggttcg gtacaggcgg tgaatcatat gtactatata gaagcacttg cacgcgccgg    540
agttataaag ttagaaacaa atcggaagaa aacggtagat tacctcggtg gtggtgactc    600
tgattcatca acggtaattg atttatgcg tgttgacgtg aaatcaacca ccgccggttt    660
aaatctggat ctcaactttc ctccaccgga aaacatgtga catcaccaga gacgacgatg    720
aagacgatcg gagatatttt gcgagaaaca ttttttaattt agtacaagtt cctttttaat    780 gtttttaat ttaaacagaa aaggaaaaaa aaagtatat agaattagat atatagatga    840
tagaaaactg aagagccatc gccgttgctg ctgccgtcgc cgccggcgac gattaatcac    900
cgccgatgtc aatatcaaga agggctgatc tattttttacc cttttttgca acagaaaaaa    960
aaacaaatct atttgatttt gcaaagctgt tgtttccatt agatcatcct tatcatatag   1020
ttattataat acattgttgc cggtttttt ttttttttt caaaagtatc tcaatgtttg   1080
cattatttac aagacatttt ctggtatact acaagctctt ctaggtggag ctccatact   1140 gaatgaacac tattaagggg acgataaata agtagattga acaaaaaat ctcgtggcgc   1200 aacagccaag gagaagccaa ataactgact ttctatatga tattttcact tgaagatagt   1260
ccttatctta catgccacca gcggaaagct tcctggtcag ggatggagtt aacttctgct   1320
gtacaattta aaggtgcaga cgtttctctg ctatcatcaa tcgatctttc tgaattttcg   1380
ctggtgctgc acatcttttg tgttcaccca cgtgatttgt gttccagatg ttggcggact   1440
gcggccacgt tctgcaggct gtgaccttt cccaggctgg gataatcttt gtataaaatc   1500
actcatatga ttatagatac ttagccggtg tctgttgcag gctgtgaaaa aggcaacaaa   1560
```

```
accatagaga atacttcgaa gagctttgaa aatctgagag aaaaggtcat tccaagaga       1620 acgccatatg gatacggata ctgcactgga tgtcactgta gtctccacct gagaagtgac     1680
tcgaactatg ctactcacga acagccatga atccataatc acttcatata tagaagtaca     1740
taaaaagccc agaaggctgg aaaaaccaaa gaccagccga attggagcat acgttacttc     1800
ccacagaatc cagaagatag gatacaataa ataagtcaca agattccaaa taaacgatgt     1860
ggtataccag agaggtagta ataaaatctc aatggttttt cccaccaagg tataagaaga     1920
ccagactgta aaccatatca cggaaaagaa atcttccata atttgtgcac acatagtcga     1980
gtaaggaagg aagaatccca caaactcaac aagtggacct gccattggct gtgtgagaac     2040
ggagaaaaat gatcgagtag tacgcattgt catgaggaac cacctgaagg ccttctgaaa     2100
attgtgcaga aatagcatgg ttcccaagta ctgaattctt gataccattt cccatgtttc     2160
aatccaatca aaagaggac caaacaaact agatgctgtc gctttgagta caggtacatt       2220
tttgtataaa tcataaaatc caatcagaac agtaaccaca gagattatga catataaaaa     2280
tcttgctaga gggcacatcc atgggcgata atatggcaa atactggat aggactggag        2340 aaatatgacc catgacggaa gcccagcttc cagtagtcta agaagccgta agtccgaaag     2400
aatgatgtct ctcagtttga aagggaaatc acgatgatta aaacgaaaca aaagcaaaat     2460
atctttgtac tgggaggctt caactacttc agaagtactt ctgtcagagg gctcaccatg     2520
tagttgtgag tcaatagatt cagaaaaggg ctcctcagag agcatatcaa cattgaatcg     2580
cttactgata gacttcaaaa gttttcttct cttatgaggt tcatcaagtg aagttggtgt     2640
atgcagagaa atttcaccat ttgctgttgc agggtacata ctgaaacttc tcattgaacc     2700
gcaaggagat tcatcatcgt cacttgaatt ggcagaagaa atatcactgt ccgccacatc     2760
agaagtatcc cggaaaatgt cttgagaatc ataaaatacc tctcctatag tagattccaa     2820
acacactttc aggagatgat gttctgtggg agtcccagaa aaccatgacg acatgcattt     2880
agcagcttga gcggccgc                                                    2898
```

<210> SEQ ID NO 45
<211> LENGTH: 973
<212> TYPE: DNA
<213> ORGANISM: Lycopersicon esculentum

<400> SEQUENCE: 45

```
tttgaattag ctatggcgcc taaggaaaaa attggtgcag ttacagctat ggcaatggtg      60
aatttaaatg gaatttcgaa agaggtgcat tatagaggtg taaggaagag gccatggggg    120
agatacgcgg cggagattag agatcctggg aaaaaagta gggtttggtt aggtactttc     180
gatactgcgg aggaggcggc tagagcttat gataacgctg ctagagaatt tcgtggagcg    240
aaagcgaaaa ctaattttcc gaattagaa atggaaaaag aggaagatct gaaattcgct     300
gtgaaaaatg aaatcaatcg gagtccgggt cagactagta ctgtggagtc atcgagtccg    360
gttatggttg attcatcatc gccgttagat ctaagtctct gtggatcaat cggcgggttt    420
aatcatcata cggttaagtt cccgagctcc ggtggaggtt ttaccggttc ggtgcaggcg    480
gtgaatcgta tgtactatat agaagcactt gcacgcgccg gagttataaa gttagaacaa    540
atcggaagaa aacggctaga ttacctcggt ggtggtgact ctgattcatc aacggtaatt    600 gatttttatgc gtgttgacgt gaatcaacc accgccggtt taaatctgga tctcaacttt    660
cctccaccgg aaaacatgtg acatcaccag agacgacgat gaagacgatc ggagatattt    720
```

| | |
|---|---|
| tgcgagaaac attttaatt tagtacaagt tcctttttaa tgtttttaa tttaaacaga | 780 |
| aaaggaaaaa aaaagtata tagaattaga tatatagatg atagaaaact gaagagccat | 840 |
| cgccgttgct gctgccgtcg ccgccggcga cgattaatca ccgccgatga atatcaagaa | 900 |
| gggctgatct attttaccc ttttttgcaa cagaaaaaaa aacaaatcta tttgattttg | 960 |
| caaaaaaaaa aaa | 973 |

<210> SEQ ID NO 46
<211> LENGTH: 603
<212> TYPE: DNA
<213> ORGANISM: Arabidopsis thaliana

<400> SEQUENCE: 46

| | |
|---|---|
| atggctccaa gacaggcgaa cggtagaagc attgccgtga gtgaaggcgg cggagggaag | 60 |
| acgatgacga tgacgacgat gcggaaggaa gtgcacttta gaggtgtgag gaagcgtcca | 120 |
| tggggtagat acgcggcgga gatccgtgac ccgggaaaga aaacccgggt ttggctcggg | 180 |
| acattcgaca cggcggagga agctgcaaga gcttacgaca ccgccgctag agagtttcgt | 240 |
| ggctccaaag caaagactaa tttccctctt cccggagagt ctactacggt taacgacggt | 300 |
| ggcgagaacg attcttacgt caaccgtacg acggtgacga cggcgcgtga gatgacacgt | 360 |
| cagagatttc cgtttgcatg tcaccggag cgtaaagtcg tcggtggtta tgcttctgct | 420 |
| ggttttttct tcgatccgtc aagagctgct tcgttaagag cagagctttc tcgggtttgt | 480 |
| ccggttcggt ttgatccggt taatatcgag ttgagtattg gtattcgaga accgtaaaa | 540 |
| gttgaaccga gaagagaact aaaacctggat cttaacctag ctccaccggt ggtggacgtt | 600 |
| tag | 603 |

<210> SEQ ID NO 47
<211> LENGTH: 600
<212> TYPE: DNA
<213> ORGANISM: Oryza sativa

<400> SEQUENCE: 47

| | |
|---|---|
| atgcgtcgcg gcggcgcggc ggaggaggac gcggaggcgg cgaggttccg cggggtgcgg | 60 |
| aagcggccgt gggggaggta cgcggcgag atccgcgacc cggcgaagaa ggcgcgggtg | 120 |
| tggctgggga cctacgactc cgccgaggac gccgcgcgcg cctacgacgc ggcggcgcgg | 180 |
| gcgctgcgcg gggccaaggc caagaccaac ttccccctct cccctcccca cgcccaaccc | 240 |
| cagctccacc accaccacca ccaccacctc acctaccccg ccgccgctgt tgtcgccgct | 300 |
| aggccggcca ctagcagcct cagctccacc gtcgagtcgt tcggcacccg gccgcggccg | 360 |
| gtgctcccgc cgcggccgcc ccgccgccgc ccgatcccg acggtgactg ccgcagcgac | 420 |
| tgcgggtcgt cggcgtcggt ggtggacgac gactgcgcgg acgccgccgc ctcgccctcg | 480 |
| tgccggctcc cgttccagtt cgacctcaac ctgcctcctg gtggaggcgg cggcggcggc | 540 |
| ggcggctttg gctgtgccta cgacgacgag gagctgaggc tgacggcgct gcggctctga | 600 |

<210> SEQ ID NO 48
<211> LENGTH: 973
<212> TYPE: DNA
<213> ORGANISM: Pisum sativum

<400> SEQUENCE: 48

| | |
|---|---|
| ggggaaaaag attgaacctg tgaagatggg tcgaggaggc gctacaaccg ctgcggcggc | 60 |
| ggtcgaaccg gttttttca aagaaccgag atacagaggg gttagaaaaa gaccgtgggg | 120 |

```
acggttcgcg gctgagatca gagatccttt gaagaaagca agggtttggc ttggaacctt    180
cgataccgct gaagaggcgg cgcgtgcgta cgacaccgcc gctagaaatc tccgtggacc    240
gaaagccaag acaaattttc ctctcgcaca gccttttat caaatcctg aagccggaaa     300
tccgttcggc gagcttagat tctacgccgg cggtgccgga gaaggttttc aggatcatcg    360
gagacctacc tcaagtggta tgagcagcac ggttgagtcc ttcggcggtc cacgtccggt    420
cagaccaccg atgccgccgt ctgctgtcac cgggaggcgt acccaagga caccgccggt    480
tgctcctgga gactgccgta gcgactgcga ttcttcatca tcggttgtcg acgatgccga    540
caacgacaac gcggcttcat ccactatgct ttcgtttaaa cgccagccgc tgccgtttga    600
tctgaacgcg ccgccgttgg aggaaggtga cgtggcgaac ggactcggtg aggatctgca    660
ctgcactctt ctctgcctct aatgaaaatt gagatatgtg atgtattgga tcgtgaagaa    720
aattatgaat tttttttact tcaattttt tgcttttct ttttttcccc tttttttaat     780
tatgcggaaa aaatgaaaat gaagatgaaa tttatgattg atgatcggtt atgagattat    840
ggttgatata atcttaattt ctgtgagagt ttgtcttctc ttctgctttg atgtatgaaa    900
aaaaggctat atattatgtt atcaatcata attttatttt tccaaaaaaa aaaaaaaaaa    960
aaaaaaaaaa aaa                                                       973

<210> SEQ ID NO 49
<211> LENGTH: 668
<212> TYPE: DNA
<213> ORGANISM: Capsicum annuum

<400> SEQUENCE: 49
ggcacgagct tattttaaa aaaaaatggc aatgaaggaa aaagttaacg gcggtatgaa      60
agttggaaat tcgaaatgta acggagtgaa taacaacaaa gatgttcatt acagaggagt    120
aaggaagagg ccatggggtc gttacgctgc tgaaatccgt gatcccggta agaaaagtag    180
agtttggtta ggcacctttg acacggcaga ggaagcggca aaagcttatg atgctgcagc    240
tagagagttc cgtggatgca aagctaaaac aaacttccct ttaccatcgg aaaatcagaa    300
tggcagtgat agtggtagcc cggatgagtc ttttagtgga gaaaatcgtg ctcacgcgcc    360
gtctgagttt gaactcacgc gctgccttgg tgctggtggt gaaggagttg gcaatggtgg    420
tcgattagct gaagttgggt tggtgagaaa tggggataca attgttcacg cgcctactga    480
actcgatctc acacgcctcc ttggtgctgg tggtgaaggg ggtgacaata gtggctattc    540
agctgaagtt ggtctggtaa gaatgggatt tccgattttt caccaccaac cgcccattga    600
agctccgatg atgagcaacc gcagtagccc tgctgagtct tatagtgggg aaactattat    660
taacacgc                                                             668

<210> SEQ ID NO 50
<211> LENGTH: 855
<212> TYPE: DNA
<213> ORGANISM: Gossypium hirsutum

<400> SEQUENCE: 50
ggcacgaggt tcatctcact actgttcaag aaaagttact taaagaaagg aaaaccatgg     60
ctcctagatc aaaacccagc ccgattagcc cgaatcccga cccgaattct aaggagatcc    120
gctaccgcgg cgttaggaag cgcccatggg gccgttacgc agccgagatc cgagacccga    180
ggaaaaagac tcgagtctgg ctcggcacct tcgacaccgc cgaggaagca gcgcgtgctt    240
```

| | |
|---|---|
| acgatgcgaa ggcgcgagag ttccgcggcg ctaaggcgaa acaaatttc gccgacaaca | 300 |
| acgccaacga cttcacgcgc agccctagcc agagcagcac cgtggagtct tcttctccgc | 360 |
| cgccacttga ccttactctg gccagcccgt gttcttccct ccctgtgacg gcgcagcgtc | 420 |
| cggtttactt cttcgatgcc ttcgctactg gcggttcggg ttgccccgca tccggattcg | 480 |
| ctcaaagcga ctccgattcg tcgtcgtctg ttgtagattt tgaaggagga gtgcggcgga | 540 |
| gagtgtttga tcttgatctt aaccagttgc cagctgaaat ggattgattt gcctcctttt | 600 |
| ttcaatatgt cgttttcagc ttcaattctc agcgttttgg gctttcctct ttttttattt | 660 |
| ttcccttaat ttttgggtta aaatttaaaa ctgacatgta atgtatgttg tgtgtaaaaa | 720 |
| aaaaattgta actcctagag atctatattt ttggcaactt gagaacattt tctcaatgtt | 780 |
| gtttccctt tattataatt aaaaaaatta ataacataaa ttaaatgctt tttcataaaa | 840 |
| aaaaaaaaaa aaaaa | 855 |

```
<210> SEQ ID NO 51
<211> LENGTH: 1038
<212> TYPE: DNA
<213> ORGANISM: Oryza sativa

<400> SEQUENCE: 51
```

| | |
|---|---|
| atgcaggcgc agcaggccat ggacgagccc gccaacgcgc agctgtacgg ccacgctcac | 60 |
| gcgcactcgc accaccaccg gagcaagcgc ccgtcgcccg gtggcggcgg cggcggcgcg | 120 |
| gcgactctgg gcgcggacgg tggcggtggc ggcggctctc tcagcgggac gcggtaccgc | 180 |
| ggcgtgcggc gcaggccgtg gggacggttc gcagcggaga tccgggaccc ggcgtccaag | 240 |
| gagcggcgct ggctcggcac gttcgacacc gccgagcagg ccgcctgcgc ctacgacgtc | 300 |
| gccgcgcgcg ccatgcgcgg caccagggcg cgcaccaact tccccgtccc cgccgccgcc | 360 |
| ggcttcccgg ggggaggcgg cggcgggtgc tggccgtggg ttaacatccc gccgcagggc | 420 |
| gcggcggcgc cggcgtcgca ccagcagccg ctcaacacgc tcctcctcca caacctcctc | 480 |
| atgagctcct cccccacgg ctgcctcctc ctgcaccacg ccggccacgg ccacggccac | 540 |
| gcccattccc attcccactc ccacagccgc gcacacaacc ccagtactcg cccacccacc | 600 |
| tccgcgccgc cgccgcctcc acctgccgcc gcctcatccg ccacgaccgc gccggccacc | 660 |
| acgacaggcg ccgcagcgac gtccgcgccg ggagcggacg acgacgcgtg gggcttcctc | 720 |
| ctgcgacgtg agccgccgga ggcggggctc ctgcaagacg tcctgcacgg gttctacccg | 780 |
| accaggcggc cgcacgacga cgcggggccg gcgccgaagc tggagcggcc gtacgaggcg | 840 |
| acgtcgtcgt accgcgtgtc ctcccctgg ggcgccgtcg aggactgcga cgacggcgac | 900 |
| ggcgacggcg acgacgacta ccgcgggttc ccgatgatgc cgcaggggct cctcgaggac | 960 |
| gtgatccagt gcccgcccta catggaggtc ttggcggcgc cgtcggccgc cgtcggccgc | 1020 |
| gtcagccgca ggggctga | 1038 |

```
<210> SEQ ID NO 52
<211> LENGTH: 570
<212> TYPE: DNA
<213> ORGANISM: Oryza sativa

<400> SEQUENCE: 52
```

| | |
|---|---|
| atggagctgg acatgggagc gggaggaggc ggtggagtag tgggaggtgg gcgagcggag | 60 |
| gcgcactacc gcggggtgag gaagcggccg tgggccggt acgcggcgga gatccggac | 120 |
| ccgtggaaga agacgcgggt gtggctcggc acctacgaca cgcccgtcga ggccgcgctc | 180 |

```
gcctacgacc gcgccgccgt cgcgctccgc ggcgtcaagg cgcggaccaa cttcggcagc    240
ggcagcagcg gtggtggtgg cgtcggcggg cacggccatg ccacagcca cgcccagctg    300 ccgcagcttc accaccgcat gcacccgccg cggccgccgc agggccctgg tcacttcggc    360
gggctcgaca tcagccaccc ttcgccgtgg cactatgtct acttcccggc gagggtgcag    420
gcgatggcgc cggcggcggc tggccatgtc gcggcgcacg tcgccgcgtc gctgccgtcg    480
acgacgctgg agctccggac ggggccgagc ccggcgagc tcccgttcga cctcaacgag    540
ccgccgccgg cgctgctgtt cggctcgtga                                      570

<210> SEQ ID NO 53
<211> LENGTH: 984
<212> TYPE: DNA
<213> ORGANISM: Nicotiana tabacum
<220> FEATURE:
<221> NAME/KEY: misc_feature
<222> LOCATION: (130)..(130)
<223> OTHER INFORMATION: n is any nucleotide
<220> FEATURE:
<221> NAME/KEY: misc_feature
<222> LOCATION: (973)..(973)
<223> OTHER INFORMATION: n is any nucleotide

<400> SEQUENCE: 53
aaagggctct ctctttctct caactttcct tcacccaaac agaccacaaa cagtagagag     60
agaagctgtg tttttagaga gagaaagtta gagcttctga atcctcgtct cttccatggc    120
tgtattctan ccctctcttt atatccctta atatttattt ttcatctcca aaaagaaaaa    180
aaatcttttt tttgaaccag tgggccgacc atgcggagag gtagagcagc ggcggcaccg    240
gcaccggtga ccggagaacc aaatggatct ggaggatcta aagagataag gtttcgtgga    300
gtccgaaaaa gaccatgggg aagatttgcg gcggagatca gagacccttg gaagaaaact    360
agggtttggt taggtacttt cgattctgct gaggatgccg cgcgtgctta tgacgccgca    420
gcgcgtgccc ttcgcggtcc taaagccaaa actaatttcc ctttgcctta tgctcatcat    480
caccagttca atcaagggca taaccctaat aacgatccgt ttgtggattc ccgattttac    540
cctcaggata atccgattat ttcacagaga cctacctcga gctccatgag tagtacggtg    600
gagtccttca gtggacctcg accgccgccg gcgccgcggc agcagacaac ggcgtcttcc    660
agaaagtata cgcggtcgcc gcccgtcgtg ccggacgatt gccatagcga ctgtgactcg    720
tcgtcttccg tcgttgacca cggcgactgt gaaaagaaa atgacaatga caatgacaac    780
atagcttctt cgtctttcag aaagccgttg cttttcgatc taaacttacc tccgccgatg    840
gatgacgccg gcgccgacga tcttcactgc acagcgctat gtctttgatg aaatgatggt    900
ttaatctgcc tgtcatttga accattggct tacctagttt tttttttttt aatttctttt    960
ttttgtggcg aangaaagca tgtg                                            984

<210> SEQ ID NO 54
<211> LENGTH: 567
<212> TYPE: DNA
<213> ORGANISM: Oryza sativa

<400> SEQUENCE: 54
atgcggaagt cgaagcagcc gcagccgcag ccgtcgccgg agatccggta ccggggcgtg     60
cggaagcggc cgtcggggag gtacgccgcc gagatccggg accgcgcgaa gagaccccg    120 atctggctgg gtaccttcga ctccgccgag gtggcggccc gcgcctacga cgacgccgcc    180
```

```
cgatctctcc gcgggccac cgcgcggacc aacttcccct tggccgcgcc gtccgcgccc      240
ccgccccggc cgccggcggc ggcggcggcg gccgccacgt ccagccacag cagcaccgtt      300
gagtcatgga gcggcggcgc cccacgcgcc gccgcatccg ccttagcccg ctccgccgcc      360
cccatggagg cgacccagga ggaggattgc cacagctact cgggctcctc ttcgtccgtc      420
ctctgcgagg acggcagcga cgacgcggcc gcctctcgca ctccgctgcc gttcgatctg      480
aacatgccac ctccggagga ggagctagac atggccgccg tggccgatca gatgggtatc      540
cgctacgaca cgctgctccg cctctag                                        567
```

```
<210> SEQ ID NO 55
<211> LENGTH: 1281
<212> TYPE: DNA
<213> ORGANISM: Arabidopsis thaliana

<400> SEQUENCE: 55
```

```
gctttttgtg ttgaagagag agtttcctat cttctccatt cctcccacca tctccctcat       60
cttcatcttc ctctctcttt ctctctttct caacaatctc tattagatct ttctccatta      120
ccattacctc tggctttctc ttaaatccac catcatgagg agaggaagag gctcttccgc      180
cgtcgccgga cctaccgtcg ttgccgccat caacggatct gtaaaagaaa tcagattcag      240
aggcgtaagg aagagacctt ggggacgatt cgcagctgag atccgtgatc catggaaaaa      300
agctcgtgtt tggttaggta cttccgattc cgccgaagaa gctgctcgcg cttacgactc      360
cgccgctcgt aacctccgtg gtcctaaagc caaaactaat ttccccatcg attcttcttc      420
tcctcctcct cctaatctcc gatttaatca gattcgtaat caaaatcaaa accaagtcga      480
tccgtttatg gaccaccggt tattcaccga ccatcaacaa cagttcccga ttgttaaccg      540
gcctactagt agcagcatga gcagcaccgt tgaatcgttt agcggaccca gacctacgac      600
gatgaaaccg gccacgacga agagatatcc tagaactcca ccggttgttc cggaggattg      660
tcacagcgat tgcgattcgt cgtcgtctgt aatcgacgac gacgacgata tcgcatcgtc      720
ttcacggcga cggaatccgc cgtttcaatt cgatcttaat tttccaccgt tggattgtgt      780
tgacttgttc aatggcgctg atgatcttca ctgtaccgat ctacgtctct aatgaattgg      840
taaaatcaaa ctcaaaatca cagatccgtg atcggtttga ttttaatcga aaacacacaa      900
caaaatcctt ttttttttt ttttaaattt tctgtttcgt tgatctcata taattttttac      960 tatgcgggag aaatagaaag acaaagaaac gaagaagaag aagaagatgg tgatgagctt     1020
gagagagctt gagctggttc tgtgtttctt ctgtgatgat attgtaagag tattattatt     1080
ttactattat tactaaatct tcaaaaccaa gaagaagaag accgaacacg atgatctgtt     1140
gtgtctgttt gttttactgt aagaaaaacg cagatctggg tttcgttttt tcttgagat     1200 agatcaaaca acccccatct ttgtaacata tacatttgga acactcatga ttctaaataa     1260
aaaatctaga atcttttttt c                                              1281
```

```
<210> SEQ ID NO 56
<211> LENGTH: 5327
<212> TYPE: DNA
<213> ORGANISM: Artificial Sequence
<220> FEATURE:
<223> OTHER INFORMATION: vector

<400> SEQUENCE: 56
```

```
gcgcacattt ccccgaaaag tgccacctga tgcggtgtga ataccgcac agatgcgtaa      60 ggagaaaata ccgcatcagg aaattgtaag cgttaatatt ttgttaaaat tcgcgttaaa     120
```

```
tttttgttaa atcagctcat tttttaacca ataggccgaa atcggcaaaa tcccttataa    180
atcaaaagaa tagaccgaga tagggttgag tgttgttcca gtttggaaca agagtccact    240
attaaagaac gtggactcca acgtcaaagg gcgaaaaacc gtctatcagg gcgatggccc    300
actacgtgaa ccatcaccct aatcaagttt tttggggtcg aggtgccgta aagcactaaa    360
tcggaaccct aaagggagcc cccgatttag agcttgacgg ggaaagccgg cgaacgtggc    420
gagaaaggaa gggaagaaag cgaaaggagc gggcgctagg gcgctggcaa gtgtagcggt    480
cacgctgcgc gtaaccacca cacccgccgc gcttaatgcg ccgctacagg gcgcgtccat    540
tcgccattca ggctgcgcaa ctgttgggaa gggcgatcgg tgcgggcctc ttcgctatta    600
cgccagctgg cgaaagggggg atgtgctgca aggcgattaa gttgggtaac gccagggttt    660
tcccagtcac gacgttgtaa aacgacggcc agtgaattgt aatacgactc actatagggc    720
gaattgggcc cgacgtcgca tgctcccggc cgccatggcg gccgcgggaa ttcgattgat    780
tggcgcgcct taattaacgg gctggtaaaa caaatataag tattaatata aatataatac    840
aatagaagga aaataaataa aatttccctc tgtgccgtgc aaaaatgcac ggcaatgggt    900
tggcccgcac ggcaaaggca tcgttgccgt gtccacggca atgggttggc ccgcacggca    960
aaggcatcgt tgccgtgtcc acgtctttgc cgtgcgcctt ggctctatct ttgccgtgaa   1020
gcgttctttg ccgtgtgcct tttatttctt tgccgtggga tgctgccttt gccgagcgct   1080
gagctggcgc tttgccgtgc gcgtattgtt tgccgtgcgt cctcccagag ctgtacggca   1140
aagaattcat tgccgtgcac gaggcacacg ggaaagaagt ttcgcatggc aaagggcgct   1200
gacagcacac ggcaaagagc ccggcacggc attgagcttt ttttcccgta atgatagacg   1260
gcataatata atggacgcac atgctgatgt caggatgtca cccactcatc ctagtatttg   1320
tgggacgtga attctttgtg agatgggcaa tgggatgtga acaaaataag ttttgtacta   1380
gtagataaac attttacccc ataaacaatt gttctgtatt gaatgaaaaa ttatttttgta   1440
ctggatgaaa atcttctgag taactgtgta agattaacat gaatcaagag acaaatccaa   1500
tggctacaaa gtcaactaat acttgttaaa agttccgata cttaaaatta tcaaaactga   1560
tatatagaat attgcccatc tcgccaccgt gctagtttaa cagacgatgg acgaaatatca   1620
gtcttgtatt ggataatcga tgcatgcgag ctatcggtca cctgtccatg cttccagaag   1680
gagccgagac gtggcgactt cgtccgacgc gccgactatc tgcacacgcc cggcttctcg   1740
tcgtgggcga gtcagcagtc acaggctttc cgcctaccaa ctcacacgta gcgccctatc   1800
gtggcgcttg atcgatgcaa cagcgatgcc tatcccagct cctcaagctg cttataagta   1860
tgtcctcggc catcactgct tacacaacaa acacagctac ttatcgcagt gtactaaaca   1920
agacgtacta gctagatttc gtgaggtaaa atcagtgcaa tatcacttgt gcaagccatt   1980
agcgcacacc atccaacaag agacgaaaag aagggaaagg aagccatggc gcccaggacg   2040
tcggagaagg cggcggcggc ggcggcaccg tctgccacag cggcgaccgg gctggccctc   2100
ggcgtgggcg gcggaggtgg aggtggaggt gtcgggacgc acttccgggg cgtgcggaag   2160
cgtccgtggg gccggtacgc ggcggagatc cgcgacccgg cgaagaagag ccgcgtgtgg   2220
ctgggcacgt acgacaccgc cgaggaggcg gcccgcgcct acgacgccgc cgcgcgcgag   2280
taccgcggct ccaaggccaa gaccaacttc ccgctgttcc cgtccgcgct ggccacggcc   2340
gtgcccgtcg gcgccggcgg agacggcagc cggagcagca acagcagcac cgtggagtcg   2400
ttcggcggcg acgtgcaggc gcccatgcag gccatgccgc tccctcccgc gtcgctggag   2460
```

```
ctcgacctct tccaccgcgc cgccaacgcc gcgggcggtg caggcgccgg cgtgaggttt    2520
cctttcagcg gctaccccgt gtcccacccg ttctacttct tcgggcaggc cgcggcggcc    2580
gccgccgccg ggtgccacgt gtacggcagc agcatgccgc cgcaggtgac cgtggcggcc    2640
gtgtcccaga gcgactccgg ctcctcgtcg gtggtggatc tggcgccgtc gccgcccccc    2700
gccgccgcgt cggcgcagag ggcgcccgtc gattttgacc tggacctgaa ctgcccgccg    2760
ccggcggagc tcctctgatc gtttgggcgc cggagttttt tagctgatat gatcatgact    2820
cgctagtagt ttcgttcgtc ggttttttttt tctctcttgt atgtttaggc gtccggcccg    2880
gcctggtttc tccataataa tgtgtgagta gttcccagat aagggaatta gggttcctat    2940
agggtttcgc tcatgtgttg agcatataag aaacccttag tatgtatttg tatttgtaaa    3000
atacttctat caataaaatt tctaattcct aaaaccaaaa tccagtacta aaatccagat    3060
cccccgaatt aattcggcgt taattcagta tcggcgcgcc ttaattaaaa tcgaatttcg    3120
accatatggg agagctccca acgcgttgga tgcatagctt gagtattcta tagtgtcacc    3180
taaatagctt ggcgtaatca tggtcatagc tgtttcctgt gtgaaattgt tatccgctca    3240
caattccaca acacatacga gccggaagca taaagtgtaa agcctggggt gcctaatgag    3300
tgagctaact cacattaatt gcgttgcgct cactgcccgc tttccagtcg ggaaacctgt    3360
cgtgccagct gcattaatga atcggccaac gcgcggggag aggcggtttg cgtattgggc    3420
gctcttccgc ttcctcgctc actgactcgc tgcgctcggt cgttcggctg cggcgagcgg    3480
tatcagctca ctcaaaggcg gtaatacggt tatccacaga atcaggggat aacgcaggaa    3540
agaacatgtg agcaaaaggc cagcaaaagg ccaggaaccg taaaaaggcc gcgttgctgg    3600 cgttttttcca taggctccgc cccctgacg agcatcacaa aaatcgacgc tcaagtcaga    3660
ggtggcgaaa cccgacagga ctataaagat accaggcgtt tcccctgga agctccctcg    3720 tgcgctctcc tgttccgacc ctgccgctta ccggatacct gtccgccttt ctcccttcgg    3780
gaagcgtggc gctttctcat agctcacgct gtaggtatct cagttcggtg taggtcgttc    3840
gctccaagct gggctgtgtg cacgaacccc ccgttcagcc cgaccgctgc gccttatccg    3900
gtaactatcg tcttgagtcc aacccggtaa gacacgactt atcgccactg gcagcagcca    3960
ctggtaacag gattagcaga gcgaggtatg taggcggtgc tacagagttc ttgaagtggt    4020
ggcctaacta cggctacact agaagaacag tatttggtat ctgcgctctg ctgaagccag    4080
ttaccttcgg aaaaagagtt ggtagctctt gatccggcaa acaaaccacc gctggtagcg    4140
gtggtttttt tgtttgcaag cagcagatta cgcgcagaaa aaaaggatct caagaagatc    4200
ctttgatctt ttctacgggg tctgacgctc agtggaacga aaactcacgt taagggattt    4260
tggtcatgag attatcaaaa aggatcttca cctagatcct tttaaattaa aaatgaagtt    4320
ttaaatcaat ctaaagtata tatgagtaaa cttggtctga cagttaccaa tgcttaatca    4380
gtgaggcacc tatctcagcg atctgtctat ttcgttcatc catagttgcc tgactccccg    4440
tcgtgtagat aactacgata cgggagggct taccatctgg ccccagtgct gcaatgatac    4500
cgcgagaccc acgctcaccg gctccagatt tatcagcaat aaaccagcca gccggaaggg    4560
ccgagcgcag aagtggtcct gcaactttat ccgcctccat ccagtctatt aattgttgcc    4620
gggaagctag agtaagtagt tcgccagtta atagtttgcg caacgttgtt gccattgcta    4680
caggcatcgt ggtgtcacgc tcgtcgtttg gtatggcttc attcagctcc ggttcccaac    4740
gatcaaggcg agttacatga tccccatgt tgtgcaaaaa agcggttagc tccttcggtc    4800
ctccgatcgt tgtcagaagt aagttggccg cagtgttatc actcatggtt atggcagcac    4860
```

```
tgcataattc tcttactgtc atgccatccg taagatgctt ttctgtgact ggtgagtact    4920
caaccaagtc attctgagaa tagtgtatgc ggcgaccgag ttgctcttgc ccggcgtcaa    4980
tacgggataa taccgcgcca catagcagaa ctttaaaagt gctcatcatt ggaaaacgtt    5040
cttcggggcg aaaactctca aggatcttac cgctgttgag atccagttcg atgtaaccca    5100
ctcgtgcacc caactgatct tcagcatctt ttactttcac cagcgtttct gggtgagcaa    5160
aaacaggaag gcaaaatgcc gcaaaaaagg gaataagggc gacacggaaa tgttgaatac    5220
tcatactctt cctttttcaa tattattgaa gcatttatca gggttattgt ctcatgagcg    5280
gatacatatt tgaatgtatt tagaaaaata aacaaatagg ggttccc                  5327

<210> SEQ ID NO 57
<211> LENGTH: 4943
<212> TYPE: DNA
<213> ORGANISM: Artificial Sequence
<220> FEATURE:
<223> OTHER INFORMATION: vector

<400> SEQUENCE: 57
gcgcacattt ccccgaaaag tgccacctga tgcggtgtga ataccgcac agatgcgtaa      60 ggagaaaata ccgcatcagg aaattgtaag cgttaatatt ttgttaaaat tcgcgttaaa     120
tttttgttaa atcagctcat tttttaacca ataggccgaa atcggcaaaa tcccttataa     180
atcaaaagaa tagaccgaga tagggttgag tgttgttcca gtttggaaca agagtccact     240
attaaagaac gtggactcca acgtcaaagg gcgaaaaacc gtctatcagg gcgatggccc     300
actacgtgaa ccatcaccct aatcaagttt tttggggtcg aggtgccgta aagcactaaa     360
tcggaaccct aaagggagcc ccgatttag agcttgacgg ggaaagccgg cgaacgtggc     420
gagaaaggaa gggaagaaag cgaaaggagc gggcgctagg gcgctggcaa gtgtagcggt     480
cacgctgcgc gtaaccacca cacccgccgc gcttaatgcg ccgctacagg gcgcgtccat     540
tcgccattca ggctgcgcaa ctgttgggaa gggcgatcgg tgcgggcctc ttcgctatta     600
cgccagctgg cgaaagggg atgtgctgca aggcgattaa gttgggtaac gccagggttt     660
tcccagtcac gacgttgtaa aacgacggcc agtgaattgt aatacgactc actatagggc     720
gaattgggcc cgacgtcgca tgctcccggc cgccatggcg gccgcgggaa ttcgattggc     780
gcgccttaat taataagagc agcttgccaa catggtggag cacgacactc tcgtctactc     840
caagaatatc aaagatacag tctcagaaga ccaagggct attgagactt ttcaacaaag     900
ggtaatatcg ggaaacctcc tcggattcca ttgcccagct atctgtcact tcatcaaaag     960
gacagtagaa aaggaaggtg gcacctacaa atgccatcat tgcgataaag gaaaggctat    1020
cgttcaagat gcctctgccg acagtggtcc caaagatgga cccccaccca cgaggagcat    1080
cgtggaaaaa gaagacgttc caaccacgtc ttcaaagcaa gtggattgat gtgaacatgg    1140
tggagcacga cactctcgtc tactccaaga atatcaaaga tacagtctca gaaggccaaa    1200
gggctattga cttttcaa caagggtaa tatcgggaaa cctcctcgga ttccattgcc    1260
cagctatctg tcacttcatc aaaaggacag tagaaaagga aggtggcacc tacaaatgcc    1320
atcattgcga taaaggaaag gctatcgttc aagatgctct gccgacagtg gtcccaaaga    1380 tggacccca cccacgagga gcatcgtgga aaagaagac gttccaacca cgtcttcaaa    1440
gcaagtggat tgatgtgata tctccactga cgtaagggat gacgcacaat cccactatcc    1500
ttcgcaagac ccttcctcta tataaggaag ttcatttcat ttggagagga cacgctgaaa    1560
```

```
tcaccagtct ctctctacaa atctatctct ctccattagc gcacaccatc caacaagaga    1620
cgaaaagaag ggaaaggaag ccatggcgcc caggacgtcg gagaaggcgg cggcggcggc    1680
ggcaccgtct gccacagcgg cgaccgggct ggccctcggc gtgggcggcg gaggtggagg    1740
tggaggtgtc gggacgcact tccggggcgt gcggaagcgt ccgtggggcc ggtacgcggc    1800
ggagatccgc gacccggcga agaagagccg cgtgtggctg ggcacgtacg acaccgccga    1860
ggaggcggcc cgcgcctacg acgccgccgc gcgcgagtac cgcggctcca aggccaagac    1920
caacttcccg ctgttcccgt ccgcgctggc cacggccgtg cccgtcggcg ccggcggaga    1980
cggcagccgg agcagcaaca gcagcaccgt ggagtcgttc ggcggcgacg tgcaggcgcc    2040
catgcaggcc atgccgctcc ctcccgcgtc gctggagctc gacctcttcc accgcgccgc    2100
caacgccgcg ggcggtgcag gcgcgcggcg tgaggtttcct ttcagcggct accccgtgtc    2160
ccacccgttc tacttcttcg ggcaggccgc ggcggccgcc gccgcgggt gccacgtgta    2220 cggcagcagc atgccgccgc aggtgaccgt ggcggccgtg tcccagagcg actccggctc    2280
ctcgtcggtg gtggatctgg cgccgtcgcc gccccccgcc gccgcgtcgg cgcagagggc    2340
gcccgtcgat tttgacctgg acctgaactg cccgccgccg gcggagctcc tctgatcgtt    2400
tgggcgccgg agttttttag ctgatatgat catgactcgc tagtagtttc gttcgtcggt    2460
ttttttttct ctcttgtatg tttaggcgtc cggcccggcc tggtttctcc ataataatgt    2520
gtgagtagtt cccagataag ggaattaggg ttcctatagg gtttcgctca tgtgttgagc    2580
atataagaaa cccttagtat gtatttgtat ttgtaaaata cttctatcaa taaaatttct    2640
aattcctaaa accaaaatcc agtactaaaa tccagatccc ccgaattaat tcggcgttaa    2700
ttcagtatcg gcgcgcctta attaaaatcg aatttcgacc atatgggaga gctcccaacg    2760
cgttggatgc atagcttgag tattctatag tgtcacctaa atagcttggc gtaatcatgg    2820
tcatagctgt ttcctgtgtg aaattgttat ccgctcacaa ttccacacaa catacgagcc    2880
ggaagcataa agtgtaaagc ctggggtgcc taatgagtga gctaactcac attaattgcg    2940
ttgcgctcac tgcccgcttt ccagtcggga acctgtcgt gccagctgca ttaatgaatc    3000
ggccaacgcg cggggagagg cggtttgcgt attgggcgct cttccgcttc ctcgctcact    3060
gactcgctgc gctcggtcgt tcggctgcgg cgagcggtat cagctcactc aaaggcggta    3120
atacggttat ccacagaatc aggggataac gcaggaaaga acatgtgagc aaaaggccag    3180
caaaaggcca ggaaccgtaa aaaggccgcg ttgctggcgt ttttccatag gctccgcccc    3240
cctgacgagc atcacaaaaa tcgacgctca agtcagaggt ggcgaaaccc gacaggacta    3300
taaagatacc aggcgtttcc ccctggaagc tccctcgtgc gctctcctgt tccgaccctg    3360
ccgcttaccg gatacctgtc cgcctttctc ccttcgggaa gcgtggcgct ttctcatagc    3420
tcacgctgta ggtatctcag ttcggtgtag gtcgttcgct ccaagctggg ctgtgtgcac    3480
gaaccccccg ttcagcccga ccgctgcgcc ttatccggta actatcgtct tgagtccaac    3540
ccggtaagac acgacttatc gccactggca gcagccactg gtaacaggat tagcagagcg    3600
aggtatgtag gcggtgctac agagttcttg aagtggtggc ctaactacgg ctacactaga    3660
agaacagtat ttggtatctg cgctctgctg aagccagtta ccttcggaaa aagagttggt    3720
agctcttgat ccggcaaaca aaccaccgct ggtagcggtg gtttttttgt ttgcaagcag    3780
cagattacgc gcagaaaaaa aggatctcaa gaagatcctt tgatcttttc tacgggtct    3840 gacgctcagt ggaacgaaaa ctcacgttaa gggattttgg tcatgagatt atcaaaaagg    3900
atcttcacct agatcctttt aaattaaaaa tgaagtttta aatcaatcta agtatatat    3960
```

```
gagtaaactt ggtctgacag ttaccaatgc ttaatcagtg aggcacctat ctcagcgatc    4020
tgtctatttc gttcatccat agttgcctga ctccccgtcg tgtagataac tacgatacgg    4080
gagggcttac catctggccc cagtgctgca atgataccgc gagacccacg ctcaccggct    4140
ccagatttat cagcaataaa ccagccagcc ggaagggccg agcgcagaag tggtcctgca    4200
actttatccg cctccatcca gtctattaat tgttgccggg aagctagagt aagtagttcg    4260
ccagttaata gtttgcgcaa cgttgttgcc attgctacag gcatcgtggt gtcacgctcg    4320
tcgtttggta tggcttcatt cagctccggt tcccaacgat caaggcgagt tacatgatcc    4380
cccatgttgt gcaaaaaagc ggttagctcc ttcggtcctc cgatcgttgt cagaagtaag    4440
ttggccgcag tgttatcact catggttatg gcagcactgc ataattctct tactgtcatg    4500
ccatccgtaa gatgcttttc tgtgactggt gagtactcaa ccaagtcatt ctgagaatag    4560
tgtatgcggc gaccgagttg ctcttgcccg gcgtcaatac gggataatac cgcgccacat    4620
agcagaactt taaaagtgct catcattgga aaacgttctt cggggcgaaa actctcaagg    4680
atcttaccgc tgttgagatc cagttcgatg taacccactc gtgcacccaa ctgatcttca    4740 gcatcttta ctttcaccag cgtttctggg tgagcaaaaa caggaaggca aaatgccgca    4800
aaaaagggaa taagggcgac acggaaatgt tgaatactca tactcttcct ttttcaatat    4860
tattgaagca tttatcaggg ttattgtctc atgagcggat acatatttga atgtatttag    4920
aaaaataaac aatagggggt tcc                                           4943
```

METHODS AND COMPOSITIONS FOR THE IMPROVEMENT OF PLANT TOLERANCE TO ENVIRONMENTAL STRESSES

CROSS-REFERENCE TO RELATED APPLICATIONS

This application is the U.S. National Stage of International Application No. PCT/NZ2009/000269, filed Dec. 1, 2009 and published in English on Jun. 10, 2010 as WO 2010/064934 A1, which claims the benefit of U.S. Provisional Application 61/118,982, filed Dec. 1, 2008; all of which are hereby incorporated by reference in their entirety to the extent not inconsistent with the disclosure herein.

TECHNICAL FIELD

The present invention relates to compositions and methods for producing plants with improved stress tolerance.

BACKGROUND ART

Environmental abiotic stresses, including drought stress, cold stress, freezing stress, heat stress and salinity stress are major factors limiting plant growth and productivity. Crop losses and reduction in yield of major crops including maize, wheat and rice caused by such stresses represent significant economic issues and also lead to food shortages in several underdeveloped countries.

The development of stress tolerant plants has the potential to reduce or solve at least some of these problems. The use of traditional plant breeding strategies to produce new lines of plants that exhibit tolerance to these types of stresses has been slow. Lack of sufficient germplasm resources, and incompatibility between distantly related plant species, present significant problems in conventional breeding. Further, the cellular processes leading to tolerance to such stresses are complex and involve multiple mechanisms of cellular adaptation and numerous metabolic pathways. This limits the success of both traditional breeding and that of genetic engineering approaches to development of stress tolerant plants. It would be beneficial to identify genes and proteins involved in controlling the complex processes leading to stress tolerance.

Regulators of gene expression, such as transcription factors, involved in controlling stress tolerance may be particularly useful in genetic engineering of plants, as a single gene may control a whole cascade of genes leading to the tolerance phenotype. Furthermore, there is sometimes commonality in many aspects of the different types of stress tolerant responses referred above. For example, genes that increase tolerance to cold or salt may also improve drought stress tolerance. This has been demonstrated in the case of the transcription factor At CBF/DREB 1 (Kasuga et al., 1999 Nature Biotech 17: 287-91) and the vacuolar pyrophosphatase AVP1 (Gaxiola et al., 2001 PNAS 98:11444-19).

Whilst some potentially useful genes have been identified, the identification and cloning of plant genes that confer tolerance to stress remains fragmented and incomplete. Although it is assumed that stress induced proteins may have a role in stress tolerance, evidence is still lacking and the function of many such stress responsive genes is unknown.

The hot and dry weather conditions in New Zealand and other countries in the summer period can have significant effect upon the yield of ryegrass. This is invariably during the dairy milking season and therefore has real effects on cost of dairy production through either reduced milk yield or the use of supplementary feeds and/or irrigation systems.

It would be beneficial to identify genes which have the capacity to confer stress tolerance in stress susceptible plant species. The development of stress tolerant crops will provide many advantages such as increasing yield and producing plants that may be cultivated in previously unsuitable environmental conditions. Thus, there exists a need for compositions and methods for producing plants with improved stress tolerance relative to cultivated counterparts.

It is an object of the invention to provide improved compositions and methods for developing plant varieties with improved tolerance to at least one of the following stresses; drought, cold, freezing, heat and salinity, or at least to provide the public with a useful choice.

SUMMARY OF THE INVENTION

In a first aspect the invention provides a method for producing a plant with increased tolerance to at least one environmental stress selected from drought, cold, freezing, heat and salinity, the method comprising transformation of a plant with a genetic construct including:
  a) a polynucleotide encoding of a polypeptide with the amino acid sequence of SEQ ID NO:1 or a variant of the polypeptide, wherein the variant is capable of increasing tolerance to at least one environmental stress selected from drought, cold, freezing, heat and salinity;
  b) a polynucleotide comprising a fragment, of at least 15 nucleotides in length, of the polynucleotide of a); or
  c) a polynucleotide comprising a complement, of at least 15 nucleotides in length, of the polynucleotide of a).

In an alternative aspect the invention provides a method for producing a plant with increased tolerance to at least one environmental stress selected from drought, cold, freezing, heat and salinity, the method comprising transformation of a plant with a genetic construct including:
  a) a polynucleotide encoding of a polypeptide with the amino acid sequence of SEQ ID NO:1 or a variant of the polypeptide;
  b) a polynucleotide comprising a fragment, of at least 15 nucleotides in length, of the polynucleotide of a); or
  c) a polynucleotide comprising a complement, of at least 15 nucleotides in length, of the polynucleotide of a).

Preferably the variant in a) encodes a polypeptide capable of increasing tolerance to at least one environmental stress selected from drought, cold, freezing, heat and salinity In one embodiment the environmental stress is drought.
In a further embodiment the environmental stress is cold.
In a further embodiment the environmental stress is freezing.
In a further embodiment the environmental stress is heat.
In a further embodiment the environmental stress is salinity.

In a further embodiment the variant has at least 50% sequence identity to a polypeptide with the amino acid sequence of SEQ ID NO: 1.

In a further embodiment the variant comprises the amino acid sequence:
$X_1X_2RGVRX_3RPX_4GRX_5AAEIRDPX_6X_7KX_8X_9$-$X_{10}WLGTX_{11}DX_{12}X_{13}X_{14}X_{15}AAX_{16}AYDX_{17}X_{18}AX_{19}$-$X_{20}X_{21}RGX_{22}X_{23}AX_{24}TNFX_{25}$ where: $X_1$=H or R, $X_2$=F or Y, $X_3$=K or R, $X_4$=S or W, $X_5$=F or Y, $X_6$=any amino acid, $X_7$=K or R or S, $X_8$=A or E or S or T, $X_9$=R or P, $X_{10}$=I or R or V, $X_{11}$=F or Y, $X_{12}$=S or T, $X_{13}$=A or P, $X_{14}$=E or Q or V, $X_{15}$=D or E or Q or V, $X_{16}$=C or L or K or R, $X_{17}$=any amino acid, $X_{18}$=A or K,
$X_{19}$=R or V, $X_{20}$=A or D or E or H or N or S, $X_{21}$=F or L or M or Y, $X_{22}$=any amino acid, $X_{23}$=K or R or T, and $X_{24}$=K or R, $X_{25}$=A or G or P (SEQ ID NO:28).

In a preferred embodiment the variant comprises an amino acid sequence selected from any one of SEQ ID NO: 2-27.

In a more preferred embodiment the polynucleotide of a) encodes a polypeptide with the amino acid sequence of SEQ ID NO: 1.

In a further aspect the invention provides a method of producing a plant with increased tolerance to at least one environmental stress selected from drought, cold, freezing heat and salinity, the method comprising transformation of a plant cell or plant with a genetic construct including:
  a) a polynucleotide comprising the nucleotide sequence of SEQ ID NO: 29, or a variant thereof, wherein the variant encodes a polypeptide capable of increasing tolerance to at least one environmental stress selected from drought, cold, freezing, heat and salinity;
  b) a polynucleotide comprising a fragment, of at least 15 nucleotides in length, of the polynucleotide of a); or
  c) a polynucleotide comprising a complement, of at least 15 nucleotides in length, of the polynucleotide of a).

In an alternative aspect the invention provides a method of producing a plant with increased tolerance to at least one environmental stress selected from drought, cold, freezing heat and salinity, the method comprising transformation of a plant cell or plant with a genetic construct including:
  a) a polynucleotide comprising the nucleotide sequence of SEQ ID NO: 29, or a variant thereof;
  b) a polynucleotide comprising a fragment, of at least 15 nucleotides in length, of the polynucleotide of a); or
  c) a polynucleotide comprising a complement, of at least 15 nucleotides in length, of the polynucleotide of a).

Preferably the variant in a) encodes a polypeptide capable of increasing tolerance to at least one environmental stress selected from drought, cold, freezing, heat and salinity In one embodiment the environmental stress is drought.

In a further embodiment the environmental stress is cold.

In a further embodiment the environmental stress is freezing.

In a further embodiment the environmental stress is heat.

In a further embodiment the environmental stress is salinity.

In a further embodiment the variant comprises the sequence of any one of SEQ ID NO: 30 to 55.

In a further embodiment the polynucleotide of a) comprises the sequence of SEQ ID NO: 29.

In a further aspect the invention provides a plant cell or plant produced by a method of the invention.

In a further aspect the invention provides an isolated polynucleotide having at least 70% sequence identity to a nucleotide sequence that encodes a polypeptide comprising an amino acid sequence of SEQ ID NO: 1, wherein the polynucleotide encodes a polypeptide capable of modulating in a plant tolerance to at least one environmental stress selected from drought, cold, freezing, heat and salinity.

In an alternative aspect the invention provides an isolated polynucleotide having at least 50% sequence identity to a nucleotide sequence that encodes a polypeptide comprising an amino acid sequence of SEQ ID NO: 1

Preferably the polynucleotide encodes a polypeptide capable of modulating in a plant tolerance to at least one environmental stress selected from drought, cold, freezing, heat and salinity.

In one embodiment the environmental stress is drought.

In a further embodiment the environmental stress is cold.

In a further embodiment the environmental stress is freezing.

In a further embodiment the environmental stress is heat.

In a further embodiment the environmental stress is salinity.

In a further embodiment said nucleotide sequence comprises the sequence from SEQ ID NO: 29.

In a further embodiment said nucleotide sequence comprises the full-length coding sequence of SEQ ID NO:29.

In a further aspect the invention provides an isolated polynucleotide that encodes a polypeptide comprising an amino acid sequence SEQ ID NO: 1.

In a further embodiment the polynucleotide comprises the sequence of SEQ ID NO: 29.

In a further embodiment the polynucleotide comprises the full-length coding sequence of SEQ ID NO: 29.

In a further aspect the invention provides an isolated polynucleotide comprising the sequence of SEQ ID NO: 29 or a variant thereof, wherein the variant is from ryegrass or fescue, and encodes a polypeptide capable of modulating in a plant tolerance to at least one environmental stress selected from drought, cold, freezing, heat and salinity.

In one embodiment the environmental stress is drought.

In a further embodiment the environmental stress is cold.

In a further embodiment the environmental stress is freezing.

In a further embodiment the environmental stress is heat.

In a further embodiment the environmental stress is salinity.

In a further embodiment the isolated polynucleotide comprises the sequence of SEQ ID NO: 29.

In a further aspect the invention provides an isolated polypeptide having at least 72% sequence identity to the amino acid sequence of SEQ ID NO: 1, wherein the polypeptide is capable of modulating in a plant tolerance to at least one environmental stress selected from drought, cold, freezing, heat and salinity.

In one embodiment the isolated polypeptide of comprises the amino acid sequence of SEQ ID NO: 1.

In a further aspect the invention provides an isolated polynucleotide encoding a polypeptide of the invention.

In a further aspect the invention provides an isolated polynucleotide comprising:
  a) a polynucleotide comprising a fragment, of at least 15 nucleotides in length, of a polynucleotide of the invention;
  b) a polynucleotide comprising a complement, of at least 15 nucleotides in length, of the polynucleotide of the invention; or
  c) a polynucleotide comprising a sequence, of at least 15 nucleotides in length, capable of hybridising to the polynucleotide of the invention.

In a further aspect the invention provides a genetic construct which comprises a polynucleotide of the invention.

In one embodiment the genetic construct is an expression construct.

Preferably the construct comprises a promoter operably linked to the polynucleotide.

Preferably the promoter is one that is not normally associated with the polynucleotide in nature.

In a further aspect the invention provides a vector comprising a genetic construct or expression construct of the invention.

In a further aspect the invention provides a host cell genetically modified to express a polynucleotide of the invention, or a polypeptide of the invention.

In a further aspect the invention provides a host cell comprising a genetic construct or expression construct of the invention.

Preferably the host cell does not form part of a living human being.

In a further aspect the invention provides a plant cell genetically modified to express a polynucleotide of the invention, or a polypeptide of the invention.

In a further aspect the invention provides a plant cell which comprises a genetic construct of the invention or the expression construct of the invention.

In a further aspect the invention provides a plant which comprises a plant cell of the invention.

Preferably the plant, comprising a plant cell of the invention is not the same as a plant that already exists in nature.

In a further aspect the invention provides a method for selecting a plant with increased tolerance to at least one environmental stress selected from drought, cold freezing, heat and salinity relative to suitable control plant, the method comprising testing of a plant for altered expression of a polynucleotide of the invention.

In a further aspect the invention provides a method for selecting a plant with increased tolerance to at least one environmental stress selected from drought, cold freezing, heat and salinity relative to a suitable plant, the method comprising testing of a plant for altered expression of a polypeptide of the invention.

In a further aspect the invention provides a plant cell or plant produced by the method of the invention.

Preferably the plant produced is not the same as a plant that already exists in nature.

In a further aspect the invention provides a plant selected by the method of the invention.

In a further aspect the invention provides a group of plants selected by the method of the invention.

In a further aspect the invention provides an antibody raised against a polypeptide of the invention.

The polynucleotides and polynucleotide variants of the invention may be derived from any species and/or may be produced synthetically or recombinantly.

In one embodiment the polynucleotide or variant, is derived from a plant species.

In a further embodiment the polynucleotide or variant, is derived from a gymnosperm plant species.

In a further embodiment the polynucleotide or variant, is derived from an angiosperm plant species.

In a further embodiment the polynucleotide or variant, is derived from a from dicotyledonous plant species.

In a further embodiment the polynucleotide or variant, is derived from a monocotyledonous plant species.

The polypeptide and polypeptide variants, of the invention may be derived from any species and/or may be produced synthetically or recombinantly.

In one embodiment the polypeptide or variant, is derived from a plant species.

In a further embodiment the polypeptide or variant, is derived from a gymnosperm plant species.

In a further embodiment the polypeptide or variant, is derived from an angiosperm plant species.

In a further embodiment the polypeptide or variant, is derived from a from dicotyledonous plant species.

In a further embodiment the polypeptide or variant, is derived from a monocotyledonous plant species.

The plant cells and plants, of the invention may be derived from any species.

In one embodiment the plant cell or plant, is derived from a gymnosperm plant species.

In a further embodiment the plant cell or plant, is derived from an angiosperm plant species.

In a further embodiment the plant cell or plant, is derived from a from dicotyledonous plant species.

In a further embodiment the plant cell or plant, is derived from a monocotyledonous plant species.

Preferred plant species are forage plant species. Preferably the species is selected from those of the following genera: *Lolium*, *Festuca*, *Dactylis*, *Bromus*, *Trifolium*, *Medicago*, *Pheleum*, *Phalaris*, *Holcus*, *Lotus*, *Plantago* and *Cichorium*.

Preferred genera are *Lolium* or *Trifolium*. Particularly preferred are the species *Lolium Perenne* and *Trifolium repens*. Most preferred is the species *Lolium perenne*.

The term "plant" is intended to include a whole plant, any part of a plant, propagules and progeny of a plant.

The term 'propagule' means any part of a plant that may be used in reproduction or propagation, either sexual or asexual, including seeds and cuttings.

The plants of the invention may be grown and either selfed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the invention.

DETAILED DESCRIPTION

Definitions

The term "tolerance or tolerant to drought stress" is intended to describe a plant or plants which perform more favourably in any aspect of their growth and development under sub-optimal hydration conditions than do suitable control plants in the same conditions.

The term "tolerance or tolerant to cold stress" is intended to describe a plant or plants which perform more favourably in any aspect of their growth and development under sub-optimal-reduced reduced temperature conditions than do suitable control plants in the same conditions.

The term "tolerance or tolerant to freezing stress" is intended to describe a plant or plants that perform more favourably in any aspect of their growth and development under temperature conditions of less than or equal to 0° C., than do suitable control plants in the same conditions.

The term "tolerance or tolerant to heat stress" is intended to describe a plant or plants that perform more favourably in any aspect of their growth and development under sub-optimal elevated temperature conditions than do suitable control plants in the same conditions.

The term "tolerance or tolerant to salinity" is intended to describe a plant or plants that perform more favourably in any aspect of their growth and development under sub-optimal elevated salinity conditions than do suitable control plants in the same conditions.

Suitable control plants may include non-transformed plants of the same species and variety, or plants of the same species or variety transformed with a control construct.

With reference to the selection methods of the invention, a plant with increased tolerance to environmental stress refers to a plant, selected from a population of plants, which performs more favourably in any aspect of growth and development under stress conditions than does an average member of the population under the same conditions.

Polynucleotides and Fragments

The term "polynucleotide(s)," as used herein, means a single or double-stranded deoxyribonucleotide or ribonucleotide polymer of any length but preferably at least 15 nucleotides, and include as non-limiting examples, coding and non-coding sequences of a gene, sense and antisense sequences complements, exons, introns, genomic DNA, cDNA, pre-mRNA, mRNA, rRNA, siRNA, miRNA, tRNA, ribozymes, recombinant polypeptides, isolated and purified naturally occurring DNA or RNA sequences, synthetic RNA and DNA sequences, nucleic acid probes, primers and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length but preferably at least 5 amino acids, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides or polypeptides of the invention being derived from a particular genera or species, means that the polynucleotide or polypeptide has the same sequence as a polynucleotide or polypeptide found naturally in that genera or species. The polynucleotide or polypeptide, derived from a particular genera or species, may therefore be produced synthetically or recombinantly.

Variants

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polypeptides possess biological activities that are the same or similar to those of the inventive polypeptides or polypeptides. The term "variant" with reference to polypeptides and polypeptides encompasses all forms of polypeptides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, mores preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, preferably at least 50 nucleotide positions, more preferably at least 100 nucleotide positions, and most preferably over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp<dot>ncbi<dot>nih<dot>gov/blast). The default parameters of bl2seq are utilized except that filtering of low complexity parts should be turned off.

The identity of polynucleotide sequences may be examined using the following unix command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from www<dot>hgmp<dot>mrc<dot>ac<dot>uk/Software/ EMBOSS The European Bioinformatics Institute server also provides the facility to perform EMBOSS-needle global alignments between two sequences on line at www<dot>ebi<dot>ac<dot>uk/emboss/align.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp<dot>ncbi<dot>nih<dot>gov/blast).

The similarity of polynucleotide sequences may be examined using the following unix command line parameters:

bl2seq -i nucleotideseq1 -j nucleotideseq2 -F F -p tblastx

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program.

For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$, more preferably less than $1\times10^{-100}$, more preferably less than $1\times10^{-110}$, and most preferably less than $1\times10^{-120}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing). Tm for polynucleotide molecules greater than about 100 bases can be calculated by the formula Tm=81.5+0.41% (G+C−log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for a polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. 1991 Dec. 6; 254(5037):1497-500) Tm values are higher than those for DNA-DNA or DNA-RNA hybrids, and can be calculated using the formula described in Giesen et al., Nucleic Acids Res. 1998 Nov. 1; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp<dot>ncbi<dot>nih<dot>gov/blast) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least %, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of a polypeptide of the invention.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp<dot>ncbi<dot>ni h<dot>gov/blast). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at www<dot>ebi<dot>ac<dot>uk/emboss/align) and GAP (Huang, X. (1994) On Global Sequence Alignment. Computer Applications in the Biosciences 10, 227-235.) as discussed above are also suitable global sequence alignment programs for calculating polypeptide sequence identity.

Use of BLASTP as described above is preferred for use in the determination of polypeptide variants according to the present invention.

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp<dot>ncbi<dot>nih<dot>gov/blast). The similarity of polypeptide sequences may be examined using the following unix command line parameters:

bl2seq -i peptideseq1 -j peptideseq2 -F F -p blastp.

Variant polypeptide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$, more preferably less than $1\times10^{-100}$, more preferably less than $1\times10^{-110}$, more preferably less than $1\times10^{-120}$ and most preferably less than $1\times10^{-123}$ when compared with any one of the specifically identified sequences.

The parameter -F F turns off filtering of low complexity sections. The parameter -p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term "vector" refers to a polynucleotide molecule, usually double stranded DNA, which is used to transport the genetic construct into a host cell. The vector may be capable of replication in at least one additional host system, such as E. coli.

The term "expression construct" refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed,
b) the polynucleotide to be expressed, and
c) a terminator functional in the host cell into which the construct will be transformed.

The term "coding region" or "open reading frame" (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a "coding sequence" is capable of being expressed when it is operably linked to promoter and terminator sequences.

"Operably-linked" means that the sequenced to be expressed is placed under the control of regulatory elements that include promoters, tissue-specific regulatory elements, temporal regulatory elements, enhancers, repressors and terminators.

The term "noncoding region" refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term "promoter" refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A "transgene" is a polynucleotide that is taken from one organism and introduced into a different organism by transformation. The transgene may be derived from the same species or from a different species as the species of the organism into which the transgene is introduced.

An "inverted repeat" is a sequence that is repeated, where the second half of the repeat is in the complementary strand, e.g.,

```
(5')GATCTA.......TAGATC(3')

(3')CTAGAT.......ATCTAG(5')
```

Read-through transcription will produce a transcript that undergoes complementary base-pairing to form a hairpin structure provided that there is a 3-5 bp spacer between the repeated regions.

A "transgenic plant" refers to a plant which contains new genetic material as a result of genetic manipulation or transformation. The new genetic material may be derived from a plant of the same species as the resulting transgenic plant or from a different species.

The terms "to alter expression of" and "altered expression" of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The "altered expression" can be related to an increase or decrease in the amount of messenger RNA and/or polypeptide produced and may also result in altered activity of a polypeptide due to alterations in the sequence of a polynucleotide and polypeptide produced.

The applicants have identified a polynucleotide from ryegrass that encodes a polypeptide (SEQ ID NO:1) which modulates in plants, tolerance to at least one environmental stress selected from drought, cold, freezing, heat and salinity. The applicants have also identified polynucleotide variants (SEQ ID NOs: 29-55) encoding polypeptide variants of SEQ ID NO:1 (SEQ ID NO:2-27) which modulate in plants, tolerance to at least one environmental stress selected from drought, cold, freezing, heat and salinity.

The invention provides plants altered, relative to suitable control plants, in tolerance to at least one environmental stress selected from drought, cold, freezing, heat and salinity. The invention provides both plants with both increased tolerance to the above and plants with decreased tolerance to above characteristic stresses. The invention also provides methods for the production or selection of such plants.

Methods for Isolating or Producing Polynucleotides

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polypeptides of the invention can be amplified using primers, as defined herein, derived from the polynucleotide sequences of the invention.

Further methods for isolating polynucleotides, of the invention or useful in the methods of the invention, include use of all, or portions of, the polynucleotides set forth herein as hybridization probes. The technique of hybridizing labeled polynucleotide probes to polynucleotides immobilized on solid supports such as nitrocellulose filters or nylon membranes, can be used to screen the genomic or cDNA libraries. Exemplary hybridization and wash conditions are: hybridization for 20 hours at 65° C. in 5.0×SSC, 0.5% sodium dodecyl sulfate, 1×Denhardt's solution; washing (three washes of twenty minutes each at 55° C.) in 1.0×SSC, 1% (w/v) sodium dodecyl sulfate, and optionally one wash (for twenty minutes) in 0.5×SSC, 1% (w/v) sodium dodecyl sulfate, at 60° C. An optional further wash (for twenty minutes) can be conducted under conditions of 0.1×SSC, 1% (w/v) sodium dodecyl sulfate, at 60° C.

The polynucleotide fragments of the invention may be produced by techniques well-known in the art such as restriction endonuclease digestion and oligonucleotide synthesis.

A partial polynucleotide sequence may be used, in methods well-known in the art to identify the corresponding full length polynucleotide sequence. Such methods include PCR-based methods, 5'RACE (Frohman M A, 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Methods for Identifying Variants

Physical Methods

Variant polynucleotides may be identified using PCR-based methods (Mullis et al., Eds. 1994 The Polymerase Chain Reaction, Birkhauser). Typically, the polynucleotide sequence of a primer, useful to amplify variant polynucleotide molecules PCR, may be based on a sequence encoding a conserved region of the corresponding amino acid sequence.

Alternatively library screening methods, well known to those skilled in the art, may be employed (Sambrook et al., Molecular Cloning: A Laboratory Manual, 2nd Ed. Cold Spring Harbor Press, 1987). When identifying variants of the probe sequence, hybridization and/or wash stringency will typically be reduced relatively to when exact sequence matches are sought.

Polypeptide variants may also be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

Polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp<dot>ncbi<dot>nih<dot>gov/blast) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or tBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, www-igbmc<dot>ustrasbg<dot>fr/BioInfo/ClustalW/Top<dot>html or T-COFFEE (Cedric Notredame, Desmond G. Higgins, Jaap Hering a, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms. Preferably the host cell does not from part of a living human being.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Host cells of the invention may also be useful in methods for production of an enzymatic product generated by an expressed polypeptide of the invention. Such methods may involve culturing the host cells of the invention in a medium suitable for expression of a recombinant polypeptide of the invention, optionally in the presence of additional enzymatic substrate for the expressed polypeptide of the invention. The enzymatic product produced may then be separated from the host cells or medium by a variety of art standard methods.

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Production of plants altered in seed yield may be achieved through methods of the invention. Such methods may involve the transformation of plant cells and plants, with a construct designed to alter expression of a polynucleotide or polypeptide capable of modulating seed yield in such plant cells and plants. Such methods also include the transformation of plant cells and plants with a combination of constructs designed to alter expression of one or more polypeptides or polypeptides capable of modulating seed yield in such plant cells and plants.

Methods for transforming plant cells, plants and portions thereof with polynucleotides are described in Draper et al., 1988, Plant Genetic Transformation and Gene Expression. A Laboratory Manual. Blackwell Sci. Pub. Oxford, p. 365; Potrykus and Spangenburg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of strategies for genetically manipulating plants are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zin gene terminator, the *Oryza sativa* ADP-glucose pyrophosphorylase terminator and the *Solanum tuberosum* PI-II terminator.

Selectable markers commonly used in plant transformation include the neomycin phosphotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenbert. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

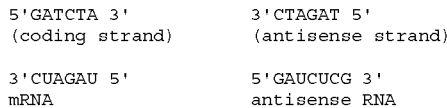

Genetic constructs designed for gene silencing may also include an inverted repeat. An 'inverted repeat' is a sequence that is repeated where the second half of the repeat is in the complementary strand, e.g.,

The transcript formed may undergo complementary base pairing to form a hairpin structure. Usually a spacer of at least 3-5 bp between the repeated region is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polynucleotides useful for effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alain et al., 1999, Plant Cell Rep. 18, 572); maize (U.S. Pat. Nos. 5,177, 010 and 5,981,840); wheat (Ortiz et al., 1996, Plant Cell Rep. 15, 1996, 877); tomato (U.S. Pat. No. 5,159,135); potato (Kumar et al., 1996 Plant J. 9,: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Nos. 5,846,797 and 5,004,863); grasses (U.S. Pat. Nos. 5,187,073 and 6,020, 539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. No. 5,792,935); soybean (U.S. Pat. Nos. 5,416,011; 5,569, 834; 5,824,877; 5,563,04455 and 5,968,830); pineapple (U.S. Pat. No. 5,952,543); poplar (U.S. Pat. No. 4,795,855); monocots in general (U.S. Pat. Nos. 5,591,616 and 6,037, 522); brassica (U.S. Pat. Nos. 5,188,958; 5,463,174 and 5,750,871); and cereals (U.S. Pat. No. 6,074,877). Other species are contemplated and suitable methods and protocols are available to in the scientific literature for use by those skilled in the art.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods for Selecting Plants

Methods are also provided for selecting plants with altered seed yield. Such methods involve testing of plants for altered for the expression of a polynucleotide or polypeptide of the invention. Such methods may be applied at a young age or early developmental stage when the altered seed yield may not necessarily be visible, to accelerate breeding programs directed toward improving seed yield.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered levels of anthocyanin. The polypeptides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate flower size in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered expression are useful in conventional breeding programs designed to produce varieties with altered seed yield.

Plants

The plants of the invention may be grown and either self-ed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The present invention will be better understood with reference to the accompanying drawings in which:

FIG. 2 shows an alignment of the ORF88 polypeptide of the invention (SEQ ID NO:1), and sequences which are variants of ORF88 SEQ ID NO:1 from several species (BAA76734.1=SEQ ID NO:25; ERF3.ARATH=SEQ ID NO:27; AAV85852.1=SEQ ID NO:20; XP_464403.1=SEQ ID NO: 19; BAD45632.1=SEQ ID NO: 26; XP473 848.1=SEQ ID NO: 11; XP_475484.1=SEQ ID NO: 2; NP915797=SEQ ID NO: 3; AAD09248.1=SEQ ID NO: 4; AAD00708.1=SEQ ID NO: 6; AAQ96341.1=SEQ ID NO: 8; AAV66332.1=SEQ ID NO: 10; AAP32202.1=SEQ ID NO: 16; AAO34705.1=SEQ ID NO: 17; AAQ96342.1=SEQ ID NO: 5; AAV51938.1=SEQ ID NO 22; AAQ55276.1=SEQ ID NO: 9; AAC49771.1=SEQ ID NO: 14; AF499716.1=SEQ ID NO: 7; BAC42202.1=SEQ ID NO: 15; BAA97123.1=SEQ ID NO: 12; BAA07322.1=SEQ ID NO: 13; AAR84424.1=SEQ ID NO: 21; AAV43790.1=SEQ ID NO: 18; XP466509.1=SEQ ID NO: 23; XP475482.1=SEQ ID NO: 24) and illustrates a consensus motif (SEQ ID NO:28) identified by the applicants which is present in all of the such sequences.

EXAMPLES

Figure 1:
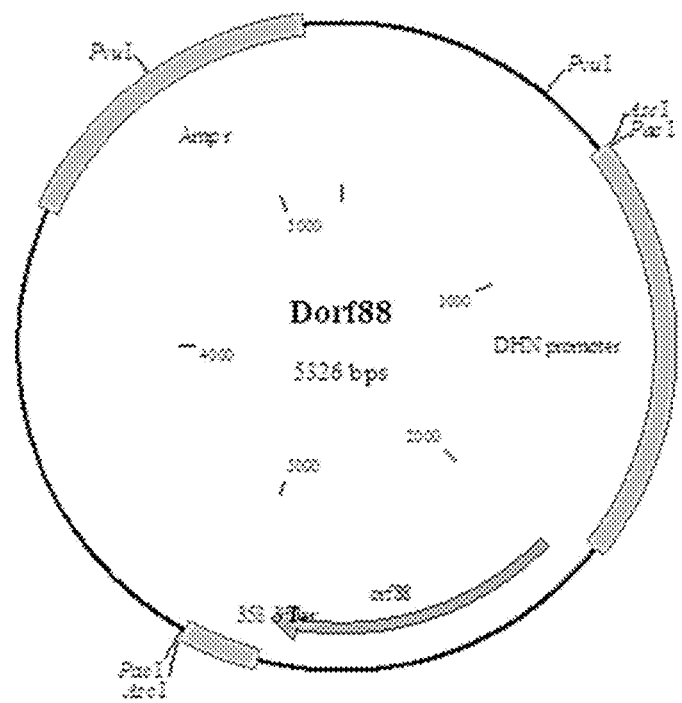
FIG. 1 shows maps of two vectors (Dorf 88 and Corf 88), for plant transformation, comprising ORF88 (SEQ ID NO:29).
Figure 1:
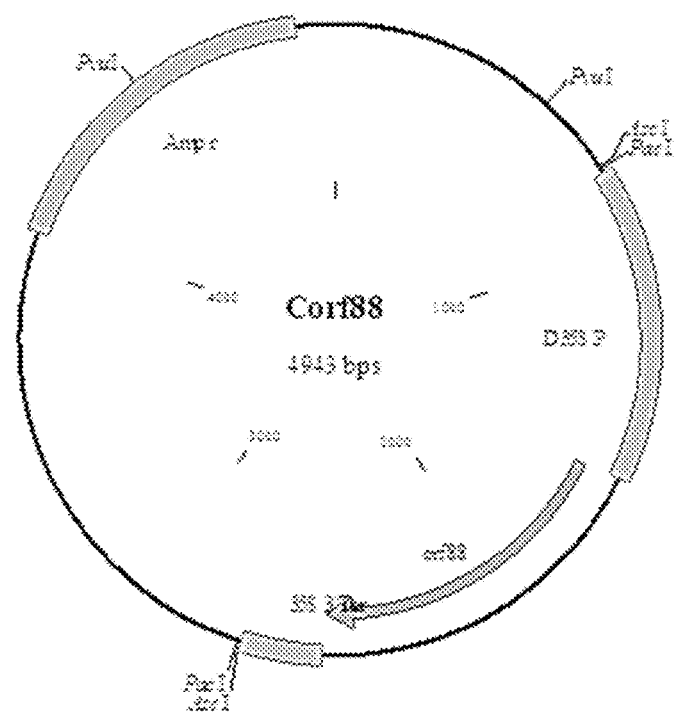

The invention will now be illustrated with reference to the following non-limiting examples.

Example 1

Identification of Polynucleotides which Modulate Tolerance to Environmental Stresses Introduction Perennial ryegrass (*Lolium perenne* L.) is a cool temperate pasture plant from the family Gramineae and the tribe Festucaceae. To generate a profile of relative gene expression patterns in ryegrass, RNA was extracted from samples obtained from ambient temperature growth, cold grown, hydrated, dehydrated and rehydrated or dehydration pre- and post-grazed plants during autumn, summer, spring and winter, and used for constructing a SAGE (serial analysis of gene expression) (Velculescu et al. 1995, *Science* 270: 484-487) library.

Materials and Methods

Perennial ryegrass (*Lolium perenne* L.) cv. Bronsyn was used throughout this study. Field grown samples were collected from active paddocks at Dexcel, Hamilton, New Zealand during the peak of each season. Grass samples were collected from pre-grazed (15 days post grazing) and post-grazed (1 day post grazing) ryegrass swards. Tufts of grass samples were harvested from 3-6 randomly chosen sites and stored in dry-ice after snap-freezing with liquid nitrogen. During spring, immature spike and floral initials were also harvested. For stress-treatment, the following conditions were used on lab-grown ryegrass: Mature lab-grown perennial ryegrass that was grown in growth chamber for 15 months at 85% RH, 20° C./18° C. and 16 h/8 h day/night regime; Hydrated control grown for 55 days at 85% RH, 20° C./18° C. and 16 h/8 h day/night regime; 6 days at 70% RH, 22° C./16° C. and 16 h/8 h day/night regime, seedlings were kept watered throughout their life; Dehydrated sample watered only for 55 days at 85% RH, 20° C./18° C. and 16 h/8 h day/night regime; 3 days at 70% RH, 28° C./20° C. and 16 h/8 h day/night regime; 3 days at 50% RH, 28° C./20° C. and 16 h/8 h day/night regime; Rehydrated samples were from dehydrated plants that was watered for 24 hours and grown at 70% RH, 22° C./16° C. and 16 h/8 h day/night regime; Cold-stressed plants were grown for 55 days at 85% RH, 20° C./18° C. and 16 h/8 h day/night regime; 7 days at 70% RH, 22° C./16° C. and 16 h/8 h day/night regime; 7 days at 70% RH, 6° C./2° C. and 16 h/8 h day/night regime, seedlings were kept watered throughout their life.

Construction of SAGE Libraries

RNA was extracted using TRIZOL® reagent (Invitrogen, CA, USA) and by the protocol described by the manufacturer from tissue that was ground in liquid nitrogen. For each SAGE library 100 μg of total RNA was used and the libraries were created using I-SAGE™ or I-SAGE™ Long kit (Invitrogen, CA, USA) according to manufacturer's protocol. From each library 960-1,920 clones were sequenced (Australian Genome Research Facility, Brisbane, Australia) and the tags extracted using the SAGE2000 software.

SAGE Bioinformatics

The relational database was designed to hold tags, libraries and expression counts of the SAGE experiments. Each tag sequence (including enzyme sequence) was searched against the whole Ryegrass non-overlapping Gene thresher and the EST sets. The search was carried out in both direction and used exact match only. Results were loaded to the relational database using General Feature Format (GFF) approach (www3<dot>ebi<dot>ac<dot>uk/Services/WebFeat)

All Ryegrass Gene thresher and the EST sequences were annotated using homology searches against some or all the following public and propriety databases:

AGI TIGR Gene Indices, *Arabidopsis*, release 11, January 2004
OGI TIGR Gene Indices, Rice, release 14-1, January 2004
GENESEQN Derwent patent DNA sequences 2002-Dec.-7
GENESEQP Derwent patent amino acid sequences 2002-Dec.-7
Os_unigene *Oryza sativa* Unigene unique sequences 2004-Mar.-18
est_others Other EST sequences (mammal, fungi, prokaryote) 2003-Mar.-11
est_plant Viridiplantae subset of Non-redundant Database of GenBank+EMBL+DDBJ EST Divisions 2004-Mar.-15
nr All non-redundant GenBank CDS translations+PDB+SwissProt+PIR 2003-Mar.-11
nr_plant Plant subset of HS subset of BT subset of All non-redundant GenBank CDS translations+PDB+SwissProt+PIR 2003-Aug.-8
nt All Non-redundant GenBank+EMBL+DDBJ+PDB sequences (but no EST, STS, GSS, or TGS sequences) 2003-Mar.-11
nt_monocots Monocot subset of All Non-redundant GenBank+EMBL+DDBJ+PDB sequences (but no EST, STS, GSS, or HTGS sequences) 2003-Mar.-11
swissprot The last major release of the SWISS-PROT protein sequence database (no updates) 2003-Mar.-28

A cutoff of E value less than E-05 was used and maximum of 10 targets per database were stored in the relational database.

Tags Annotation

Tags with hits to the Ryegrass sets were annotated by creating a summary of all the annotations of the involved sequences. The summary was generated using an algorithm to calculate the frequency of the occurrence of each word in the annotations and rank them in descending order based on the number off occurrences. The summary was limited to 10 words and a void word list was used to filter out insignificant information. The resulting summary line was used as an indication of what the tags were likely to be. Actual numbers are displayed; giving additional information that could be used to evaluate the significance of each of the words in the summary. This method of automatic annotation using keyword counts is similar to the Automatic comment that is used by the ProDom database (protein<dot>Toulouse<dot>inra<dot>fr/prodom/current/html/home<dot>php) to annotate the automatically generated protein domain families.

Detailed annotation based on the top hits of the involved sequences was displayed when viewing tags data.

A polynucleotide sequence of particular interest was identified in the above analysis. This was ORF88 (corresponds to SEQ ID NO:29).

ORF88 appears to encode an ethylene responsive element binding factor-like protein (SEQ ID NO:1). A sense and anti-sense SAGE tag has been recorded for this transcript. The anti-sense SAGE tag for the transcript accumulates in dehydrated tissues, while the sense SAGE tag accumulates in autumn pre-grazed tissues, winter roots, and spring tissues. The full transcript profile for the two SAGE tags is shown in table 1.

TABLE 1

| Anti-sense SAGE_TAG | GGTCGGAATC | Sense SAGE_TAG | ACTCGCTAGT |
|---|---|---|---|
| Winter Pre-grazed | 0/27764 | Winter Pre-grazed | 0/27764 |
| Winter Post-grazed | 0/26730 | Winter Post-grazed | 0/26730 |
| Winter roots | 0/16474 | Winter roots | 1/16474 |
| Spring Pre-grazed | 0/18832 | Spring Pre-grazed | 2/18832 |
| Spring Post-grazed | 0/16484 | Spring Post-grazed | 1/16484 |
| Inflorescence | 0/24496 | Inflorescence | 0/24496 |
| Summer Post-grazed | 0/19456 | Summer Post-grazed | 0/19456 |
| Autumn Pre-grazed | 0/28798 | Autumn Pre-grazed | 0/28798 |
| Autumn Post-grazed | 0/27748 | Autumn Post-grazed | 1/27748 |
| Mature | 0/12505 | Mature | 0/12505 |
| Cold-stressed | 0/18375 | Cold-stressed | 0/18375 |
| Hydrated | 0/15746 | Hydrated | 0/15746 |
| Dehydrated | 3/17068 | Dehydrated | 3/17068 |
| Rehydrated | 0/30416 | Rehydrated | 0/30416 |
| Total | 3/300892 | Total | 5/300892 |

Example 2

Identification Variants of ORF 88

The polypeptide sequence encoded by the ORF 88 was used as a seed sequences to perform BLASTP search against NR_PLANT database (release date). Besides BLASTP, a TBLASTN search was also performed against the NT_PLANT database (release date Jan. 1, 2005). To identify the variants, a cut-off e value of greater than 9e-25, was selected based upon the applicants' assessment the associated score values.

Figure 2:
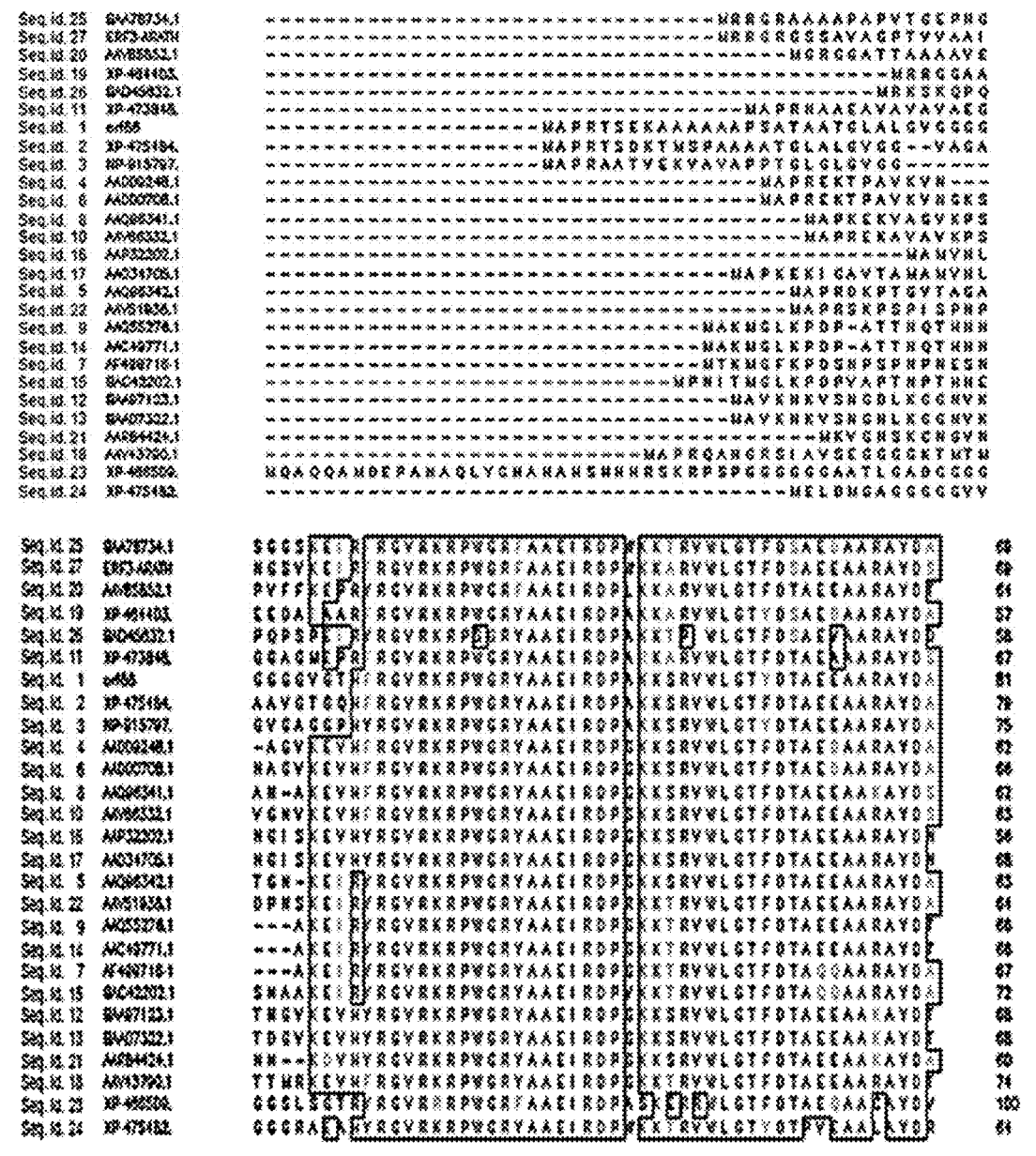
Figure 2:
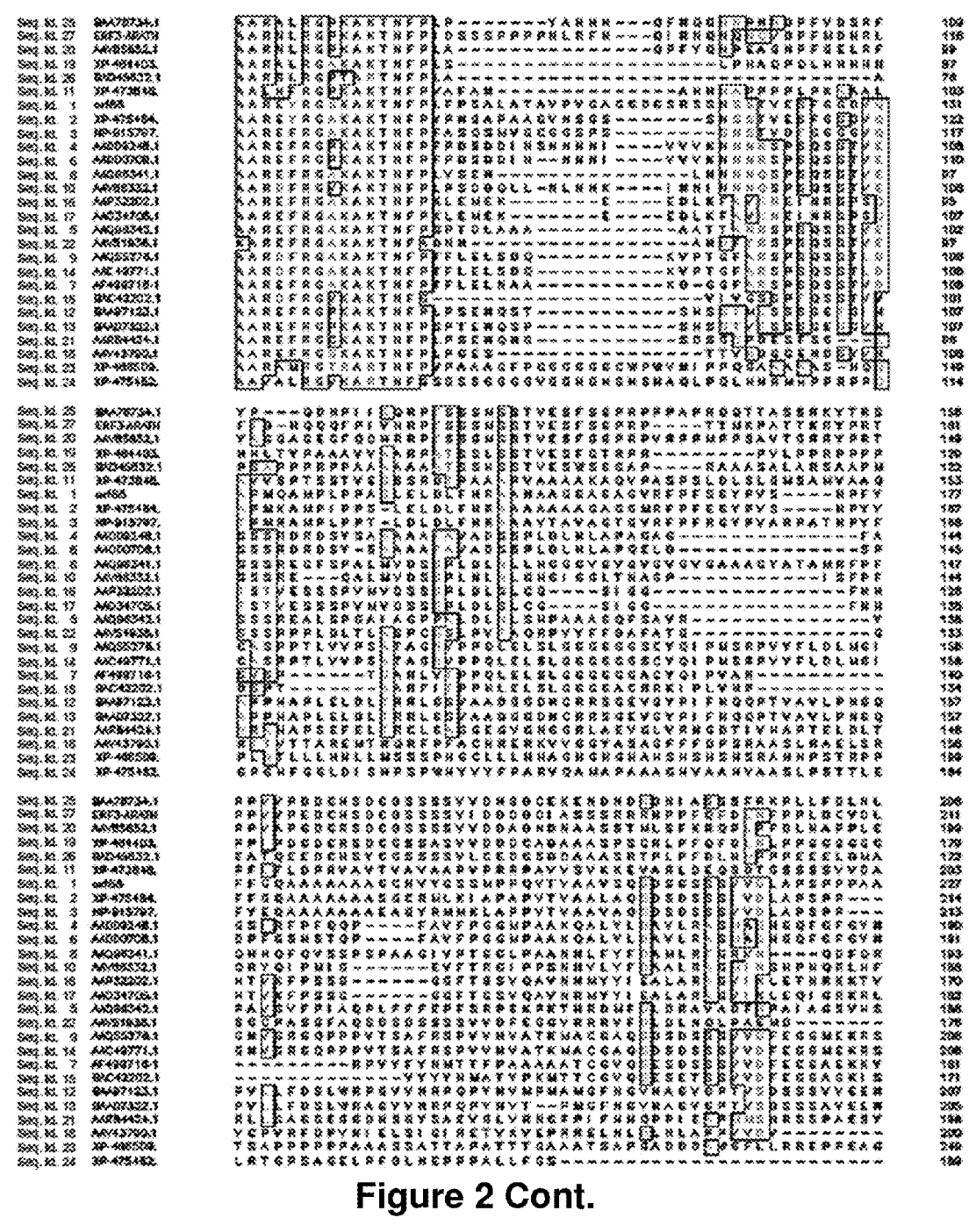
Figure 2:
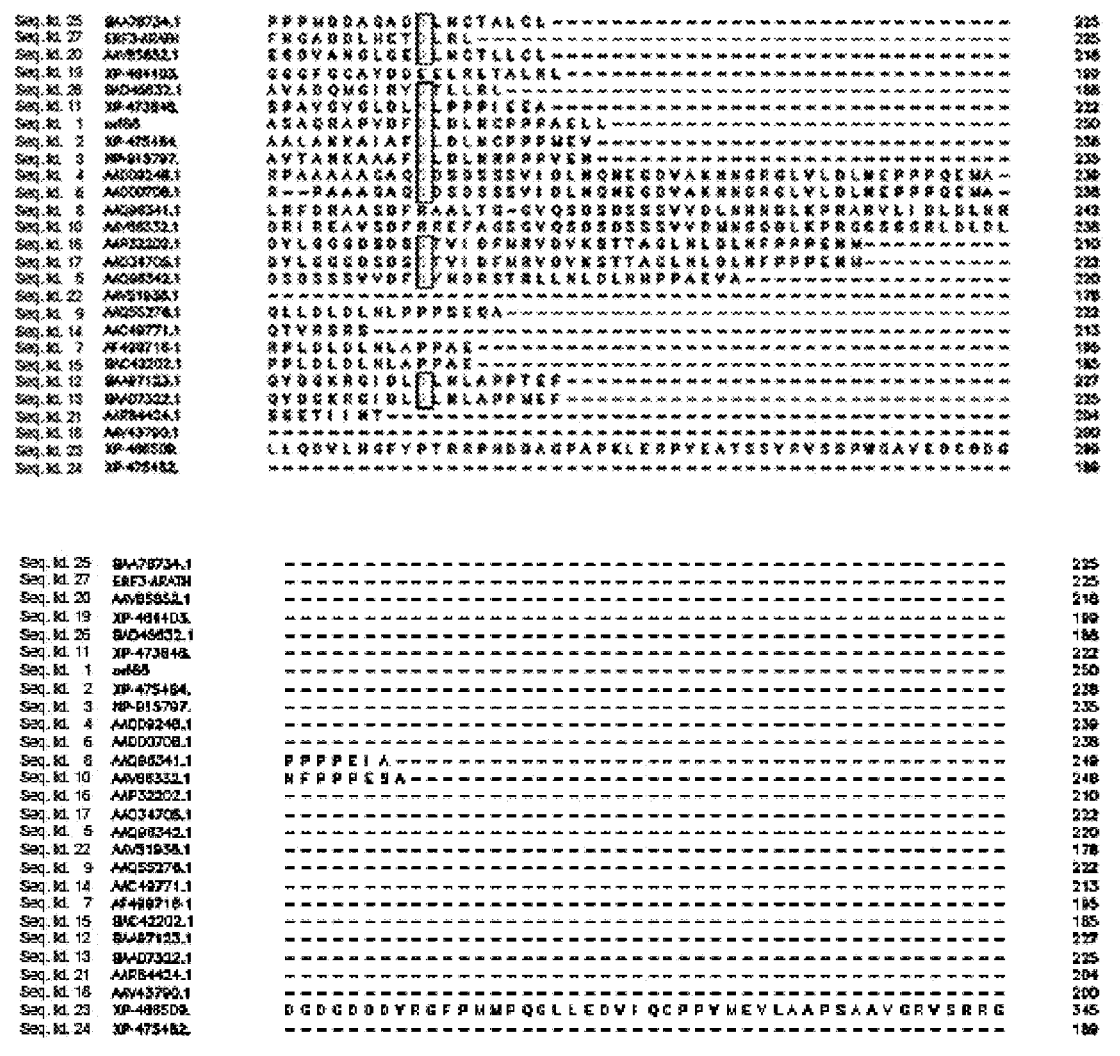

Selected variant sequences were aligned using the EMBOSS tool EMMA (Thompson, J. D., Higgins, D. G. and Gibson, T. J. 1994, CABIOS, 10, 19-29.), which is an interface to the popular multiple alignment program ClustalW. Aligned sequences were visualised using another EMBOSS tool called prettyplot, which displays aligned sequences with colouring and boxing as shown in FIG. 2.

Example 3

Preparation of Vectors Comprising Polynucleotides of the Invention for Plant Transformation Vectors Comprising ORF88

Vectors for over-expressing ORF88 were produced by standard molecular biology techniques. Maps of the vectors (Dorf 88 and Corf 88) are shown in FIG. 1. The sequence of the vectors are shown in SEQ ID NO:56 and SEQ ID NO:57 respectively.

Example 4

Transformation of Plants to Express the Polynucleotides/Polypeptides of the Invention Perennial ryegrass (*Lolium perenne* L. cv. Impact genotype 193), was transformed essentially as described in Bajaj et. al. (Plant Cell Reports, 2006, 25: 651-659). Embryogenic callus derived from mersitematic regions of the tillers of selected ryegrass lines and *Agrobacterium tumefaciens* strain EHA101 carrying a modified binary vector (FIG. 1; Dorf 88) was used for transformation experiments. Embryogenic calli were immersed with overnight-grown *Agrobacterium* cultures for 30 minutes with continuous shaking. Calli resistant to hygromycin were selected after subculturing them on co-cultivation medium for 4 weeks. After selection, the resistant calli were subcultured on regeneration medium every 2 weeks until the plants regenerated. The regenerants that continued to grow after two or three rounds of selection proved to be stable transformants. Each regenerated plant was then multiplied on maintenance medium to produce clonal plantlets and subsequently rooted on MS medium without hormones. A rooted plant from each clone was transferred into contained glasshouse conditions while retaining a clonal counterpart in tissue culture as backup. We drought-screened plants obtained from one non-transgenic control and four independent transgenic events (7AR6, 7AR7, 7AR9 and 7AR16) in a climate-controlled environmental laboratory.

Example 5

Figure 3:
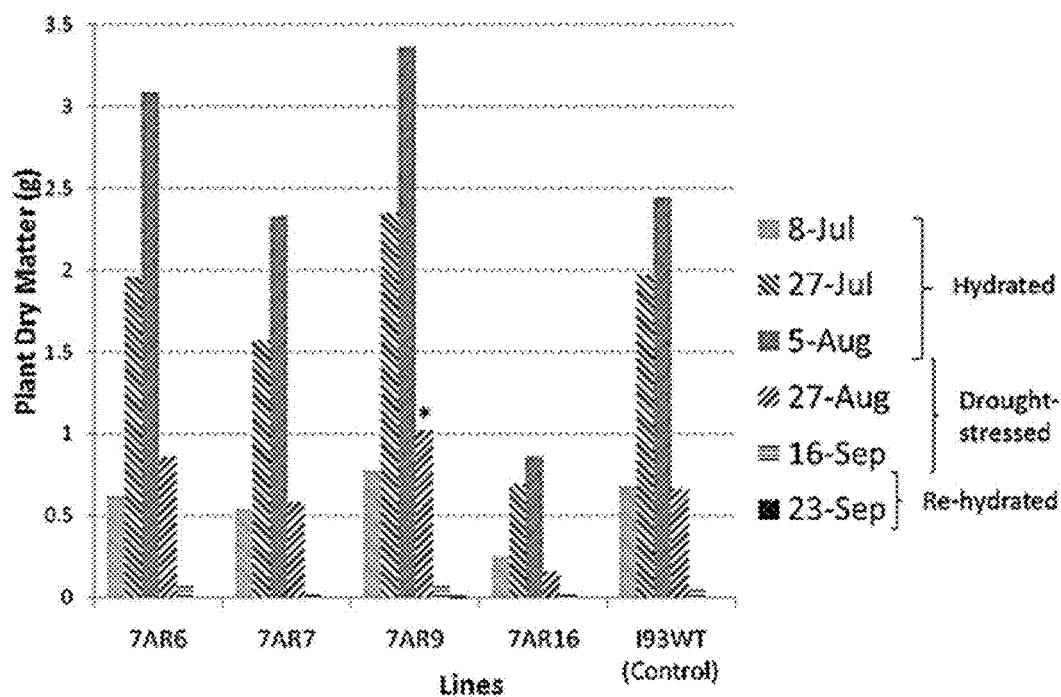
FIG. 3 shows the performance by the non-transgenic control ryegrass (193WT) and different independent transgenic ryegrass events; 7AR6 (ORF88-6), 7AR7 (ORF88-7), 7AR9 (ORF88-9), and 7AR16 (ORF88-16) as demonstrated by biomass production (measured as g dry weight) under irrigated (till 5 August), drought-stressed (5 August to 16 September) and recovery (16 September to 23 September) regimes. *=significant at 5% level (LSD); F test for treatment effect is also significant.
Figure 4:
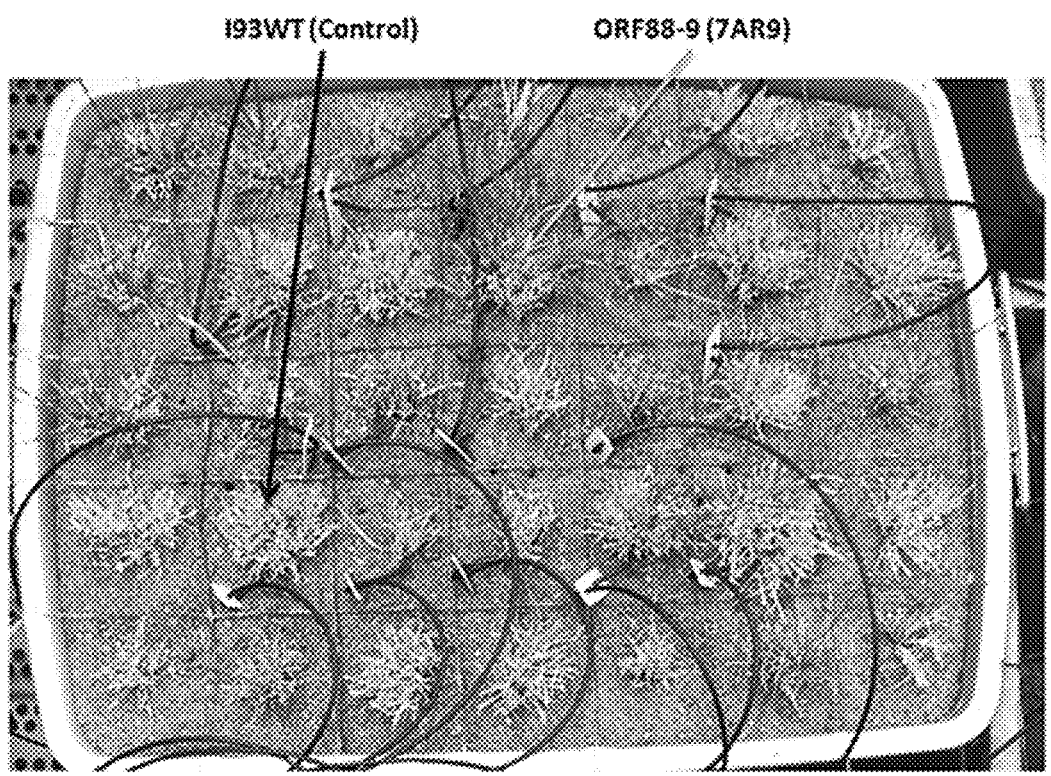
FIG. 4 shows the condition of plants after two six-week drought stress interrupted by one week of irrigated regime. Non-transgenic control (black arrow) suffered compared against the best performing transgenic event ORF88-9 (7AR9) (grey arrow).

Demonstration of Stress Tolerance of Plants Transformed to Express Polynucleotides/Polypeptides of the Invention Drought Screening in Growth Chamber The experimental system for testing drought tolerance was built of 120 Liter boxes connected to an automated drip irrigation system. The boxes were placed on a mobile tray and supported at the sides by metal frame. The boxes were plugged at the bottom with rockwool and progressively filled with washed mortar sand using water to achieve uniform packing. Each box contained 15 experimental plants bordered by 20 non-experimental plants. Each plant was started with 12 tillers and five independent events, each replicated seven times were compared against a non-transgenic parental line, also replicated seven times. The plants were arranged using a completely randomized block design, and grown at 70% relative humidity; 16/8 hours day/night cycle and under 650 $\mu mol \cdot m^{-2} \cdot s^{-1}$ light intensity. The plants were irrigated daily, once in the morning with 50 mL Hoagland's solution (Hoagland and Arnon, 1938) and again in the afternoon with 50 mL plain water. The plants were acclimated initially for two weeks and then the plants were trimmed back to 50 mm height. All plants were allowed to establish during the next six weeks and were trimmed to 50 mm height once every two weeks. Drought-stress was imposed two months after the planting date by withholding the application of Hoagland's solution and water. During the drought screening, all plants were subjected to 60% relative humidity during the first seven days and then reduced to 50% thereafter; 16/8 hours day/night cycle and 650 $\mu mol \cdot m^{-2} \cdot s^{-1}$ light intensity. The drought-stress was applied for three weeks (FIG. 7) and plants trimmed back to 50 mm height. The trimmed materials were used to measure the above ground biomass. The boxes were irrigated with water for three minutes and then the drought-regime resumed for another three weeks. At the end of the drought, plants were trimmed back to 50 mm height. All plants were re-connected to the irrigation system and also returned to 70% relative humidity; 16/8 hours day/night cycle and 650 light intensity. After one week, plants were trimmed down to 50 mm height and subjected to another round of drought lasting over six weeks. The humidity level, daylength, light intensity, etc were maintained at the same level as in the first drought period. Our analysis of above-ground biomass production indicates that transgenic lines were not different from the non-transgenic control under irrigated conditions when a pair-wise comparison (Least Significant Difference Test) was tested although the F test for treatment effect was found to be significant until the end the first drought regime. After three weeks of drought, one of the four transgenic events (ORF88-9; 7AR9) produced significantly more biomass than the non-transgenic control and was confirmed by a LSD test (FIG. 3). Another line (ORF88-6; 7AR6) although produced more biomass than the non-transgenic control, the difference was statistically significant (FIG. 3). Similarly, at the end of the drought trial, although these two transgenic events produced more biomass than the non-transgenic control, the differences did not compute to be significantly different, perhaps owing to the severity of the drought regime imposed that killed a major portion of the plants being tested for drought tolerance (FIG. 4).

Above-Ground Biomass

Leaf clipping dry weight was determined by trimming all plants to 50 mm clipping height. The leaves were dried at 80° C. for 48 h and the dry weight (DW) was measured. The improved ability to grow under drought-stress is calculated as the difference between the dry weight of transgenic plant event and the dry weight of non-transgenic control. A planned pair comparison involving the least significant difference (LSD) test was used to calculate the differences between the means of the transgenic events and non-transgenic control biomass production after performing the F test to confirm that the treatment effect is significant and the number of treatments is not too large.

The above examples illustrate practice of the invention. It will be appreciated by those skilled in the art that numerous variations and modifications may be made without departing from the spirit and scope of the invention.

SUMMARY OF SEQUENCES

| SEQ ID NO: | Type | Species | Reference |
|---|---|---|---|
| 1 | polypeptide | Lolium perenne | ORF88 |
| 2 | polypeptide | Oryza sativa | XM475484.1 (XP_475484.1) |
| 3 | polypeptide | Oryza sativa | NM 190908.1 (NP915797; EAZ13829) |
| 4 | polypeptide | Stylosanthes hamata | U91982.1 (AAD09248.1) |
| 5 | polypeptide | Vitis aestivalis | AY395745.1 (AAQ96342.1) |
| 6 | polypeptide | Stylosanthes hamata | U91857.1 (AAD00708.1) |
| 7 | polypeptide | Thellungiella halophila | AF499716.1 |
| 8 | polypeptide | Vitis aestivalis | AY395744.1 (AAQ96341.1) |
| 9 | polypeptide | Arabidopsis thaliana | BT010325.1 (AAQ55276.1) |
| 10 | polypeptide | Cucumis sativus | AY792593.1 (AAV66332.1) |
| 11 | polypeptide | Oryza sativa | XM_473848.1 (XP473848.1) |
| 12 | polypeptide | Nicotiana sylvestris | AB016265.1 (BAA97123.1) |
| 13 | polypeptide | Nicotiana tabacum | D38124.1 (BAA07322.1) |
| 14 | polypeptide | Arabidopsis thaliana | AF003098.1 (AAC49771.1) |
| 15 | polypeptide | Arabidopsis thaliana | AK117541.1 (BAC42202.1) |
| 16 | polypeptide | Lycopersicon esculentum | AY275554.1 (AAP32202.1) |
| 17 | polypeptide | Lycopersicon esculentum | AY192369.1 (AAO34705.1) |
| 18 | polypeptide | Arabidopsis thaliana | BT020188.1 (AAV43790.1) |
| 19 | polypeptide | Oryza sativa | XM_464403.1 (XP_464403.1) |
| 20 | polypeptide | Pisum sativum | AY822467.1 (AAV85852.1) |
| 21 | polypeptide | Capsicum annuum | AY491504.1 (AAR84424.1) |
| 22 | polypeptide | Gossypium hirsutum | AY779339.1 (AAV51938.1) |
| 23 | polypeptide | Oryza sativa | XM_466509.1 (XP466509.1) |
| 24 | polypeptide | Oryza sativa | XM_475482.1 (XP475482.1) |
| 25 | polypeptide | Nicotiana tabacum | AB024575.1 (BAA76734.1) |
| 26 | polypeptide | Oryza sativa | AP003935:147254-147820 (BAD45632.1) |
| 27 | polypeptide | Arabidopsis thaliana | AB008105.1 (BAA32420.1; ERF3-ARATH) |
| 28 | polypeptide | Artificial | consensus |
| 29 | polynucleotide | Lolium perenne | ORF88 |
| 30 | polynucleotide | Oryza Sativa | XM_475484.1 |
| 31 | polynucleotide | Oryza sativa | NM_190908.1 |
| 32 | polynucleotide | Stylosanthes hamata | U91982.1 SHU91982 |
| 33 | polynucleotide | Vitis aestivalis | AY395745.1 |
| 34 | polynucleotide | Stylosanthes hamata | U91857.1 SHU91857 |
| 35 | polynucleotide | Thellungiella halphila | AF499716.1 |
| 36 | polynucleotide | Vitis aestivalis | AY395744.1 |
| 37 | polynucleotide | Arabidopsis thaliana, | 33942046 BT010325.1 |
| 38 | polynucleotide | Cucumis sativus | AY792593.1 |
| 39 | polynucleotide | Oryza sativa | XM_473848.1 |
| 40 | polynucleotide | Nicotiana sylvestris | AB016265.1 |
| 41 | polynucleotide | Nicotiana tabacum | D38124.1 |
| 42 | polynucleotide | Arabidopsis thaliana | AF003098.1 AF003098 |
| 43 | polynucleotide | Arabidopsis thaliana | AK117541.1 |
| 44 | polynucleotide | Lycopersicon esculentum | AY275554.1 |
| 45 | polynucleotide | Lycopersicon esculentum | AY192369.1 |
| 46 | polynucleotide | Arabidopsis thaliana | BT020188.1 |
| 47 | polynucleotide | Oryza sativa | XM_464403.1 |
| 48 | polynucleotide | Pisum sativum | AY822467.1 |
| 49 | polynucleotide | Capsicum annuum | AY491504.1 |
| 50 | polynucleotide | Gossypium hirsutum | AY779339.1 |
| 51 | polynucleotide | Oryza sativa | XM_466509.1 |
| 52 | polynucleotide | Oryza sativa | XM_475482.1 |
| 53 | polynucleotide | Nicotiana tabacum | AB024575.1 |
| 54 | polynucleotide | Oryza sativa | AP003935:147254-147820 |
| 55 | polynucleotide | Arabidopsis thaliana | AB008105.1 |
| 56 | polynucleotide | Artificial, vector | pDorf88 |
| 57 | polynucleotide | Artificial, vector | pCorf88 |

The invention claimed is:

1. A method for producing a plant with increased tolerance drought the method comprising transformation of a plant with a genetic construct including a polynucleotide encoding of a polypeptide with the amino acid sequence of SEQ ID NO:1.

2. The method of claim 1 wherein the polynucleotide encodes a polypeptide capable of increasing tolerance to drought.

3. A method of producing a plant with increased tolerance to drought the method comprising transformation of a plant cell or plant with a genetic construct including a polynucleotide comprising nucleotides 1643-2392 of SEQ ID NO: 57.

4. The method of claim 3 wherein the polynucleotide encodes a polypeptide capable of increasing tolerance to drought.

5. A plant produced by the method of claim 1, that is genetically modified to contain a polynucleotide encoding of a polypeptide with the amino acid sequence of SEQ ID NO:1.

6. A genetic construct that comprises a polynucleotide that encodes a polypeptide comprising the amino acid sequence of SEQ ID NO: 1 operably linked to a promoter that is not normally associated with the polynucleotide in nature.

7. The genetic construct of claim 6 wherein the polynucleotide comprises nucleotides 1643-2392 of SEQ ID NO: 57.

8. The genetic construct of claim 6 wherein the genetic construct comprises the sequence of SEQ ID NO: 29 SEQ ID NO: 56 or SEQ ID NO: 57.

9. The genetic construct of claim 6 wherein the encoded polypeptide is capable of modulating in a plant, tolerance to drought.

10. A host cell, plant cell, or plant genetically modified to comprise a polypeptide comprising the amino acid sequence of SEQ ID NO: 1.

11. A host cell, plant cell, or plant genetically modified to comprise a polynucleotide that encodes a polypeptide comprising the amino acid sequence of SEQ ID NO: 1.

12. A host cell, plant cell, or plant comprising a genetic construct of claim 6.

13. The host cell, plant cell, or plant of claim 10 that is genetically modified to express the polypeptide.

14. A method for selecting a plant with increased tolerance to drought, relative to a suitable control plant, the method comprising testing of a plant for increased expression of the polypeptide defined in claim 1 relative to the control plant, wherein increased expression is indicative of increased tolerance.

* * * * *

UNITED STATES PATENT AND TRADEMARK OFFICE
CERTIFICATE OF CORRECTION

PATENT NO. : 8,901,376 B2
APPLICATION NO. : 13/132042
DATED : December 2, 2014
INVENTOR(S) : Puthigae et al.

Page 1 of 1

It is certified that error appears in the above-identified patent and that said Letters Patent is hereby corrected as shown below:

In The Claims

In Claim 1:

In the first line, please add the word --to-- between "tolerance" and "drought".

Signed and Sealed this
Twenty-third Day of February, 2016

Michelle K. Lee
*Director of the United States Patent and Trademark Office*